United States Patent
Wu et al.

(10) Patent No.: US 10,722,288 B2
(45) Date of Patent: Jul. 28, 2020

(54) DEVICES FOR THERMALLY-INDUCED RENAL NEUROMODULATION

(71) Applicant: Medtronic Ardian Luxembourg S.a.r.l., Luxembourg (LU)

(72) Inventors: Andrew Wu, Los Altos Hills, CA (US); Benjamin J. Clark, Redwood City, CA (US); Erik Thai, San Jose, CA (US); Nicolas Zadno, Fremont, CA (US); Denise Zarins, Saratoga, CA (US)

(73) Assignee: Medtronic Ardian Luxembourg S.a.r.l., Luxembourg (LU)

( * ) Notice: Subject to any disclaimer, the term of this patent is extended or adjusted under 35 U.S.C. 154(b) by 263 days.

(21) Appl. No.: 15/132,424

(22) Filed: Apr. 19, 2016

(65) Prior Publication Data
US 2017/0014177 A1 Jan. 19, 2017

Related U.S. Application Data

(63) Continuation of application No. 12/147,191, filed on Jun. 26, 2008, now Pat. No. 9,345,900, which is a
(Continued)

(51) Int. Cl.
*A61B 18/12* (2006.01)
*A61B 18/14* (2006.01)
(Continued)

(52) U.S. Cl.
CPC .......... *A61B 18/1233* (2013.01); *A61B 18/12* (2013.01); *A61B 18/1206* (2013.01);
(Continued)

(58) Field of Classification Search
CPC ............ A61B 18/1233; A61B 18/1206; A61B 18/1492; A61B 2017/00022;
(Continued)

(56) References Cited

U.S. PATENT DOCUMENTS 4,602,624 A 7/1986 Naples et al.
4,603,704 A 8/1986 Mund et al.
(Continued)

FOREIGN PATENT DOCUMENTS

DE 20 2007 019 566 U1 10/2013
EP 0879613 11/1998
(Continued)

OTHER PUBLICATIONS

U.S. Appl. No. 95/002,110, filed Aug. 29, 2012, Demarais et al.
(Continued)

*Primary Examiner* — Devin B Henson

(57) ABSTRACT

Methods and system are provided for thermally-induced renal neuromodulation. Thermally-induced renal neuromodulation may be achieved via direct and/or via indirect application of thermal energy to heat or cool neural fibers that contribute to renal function, or of vascular structures that feed or perfuse the neural fibers. In some embodiments, parameters of the neural fibers, of non-target tissue, or of the thermal energy delivery element, may be monitored via one or more sensors for controlling the thermally-induced neuromodulation. In some embodiments, protective elements may be provided to reduce a degree of thermal damage induced in the non-target tissues. In some embodiments, thermally-induced renal neuromodulation is achieved via delivery of a pulsed thermal therapy.

24 Claims, 18 Drawing Sheets

Related U.S. Application Data continuation of application No. 12/159,306, filed as application No. PCT/US2007/072396 on Jun. 28, 2007, now abandoned, which is a continuation-in-part of application No. 11/599,723, filed on Nov. 14, 2006, now abandoned, and a continuation-in-part of application No. 11/504,117, filed on Aug. 14, 2006, now Pat. No. 7,617,005.

(60) Provisional application No. 60/880,340, filed on Jan. 12, 2007, provisional application No. 60/816,999, filed on Jun. 28, 2006.

(51) Int. Cl.
  A61F 7/00        (2006.01)
  A61F 7/12        (2006.01)
  A61B 18/00       (2006.01)
  A61B 17/00       (2006.01)
  A61N 1/40        (2006.01)

(52) U.S. Cl.
  CPC .......... *A61B 18/14* (2013.01); *A61B 18/1492* (2013.01); *A61F 7/007* (2013.01); *A61F 7/12* (2013.01); *A61N 1/403* (2013.01); *A61B 2017/00084* (2013.01); *A61B 2018/00214* (2013.01); *A61B 2018/00279* (2013.01); *A61B 2018/00404* (2013.01); *A61B 2018/00577* (2013.01); *A61B 2018/00636* (2013.01); *A61B 2018/00666* (2013.01); *A61B 2018/00702* (2013.01); *A61B 2018/00714* (2013.01); *A61B 2018/00755* (2013.01); *A61B 2018/00779* (2013.01); *A61B 2018/00791* (2013.01); *A61B 2018/00875* (2013.01); *A61B 2018/1475* (2013.01); *A61F 2007/126* (2013.01)

(58) Field of Classification Search
  CPC ........... A61B 2017/00026; A61B 2017/00084; A61B 2018/00648; A61B 2018/00666; A61B 2018/00696; A61B 2018/00702; A61B 2018/00714; A61B 2018/00755; A61B 2018/00779; A61B 2018/00791; A61B 2018/00875
  See application file for complete search history.

(56) References Cited

U.S. PATENT DOCUMENTS

| | | |
|---|---|---|
| 4,649,936 A | 3/1987 | Ungar et al. |
| 4,709,698 A | 12/1987 | Johnston et al. |
| 4,738,812 A | 4/1988 | Raynal |
| 4,764,504 A | 8/1988 | Johnson et al. |
| 4,890,623 A | 1/1990 | Cook et al. |
| 4,976,711 A | 12/1990 | Parins et al. |
| 5,191,883 A | 3/1993 | Lennox et al. |
| 5,300,068 A | 4/1994 | Rosar et al. |
| 5,358,514 A | 10/1994 | Schulman et al. |
| 5,368,591 A | 11/1994 | Lennox et al. |
| 5,423,744 A | 6/1995 | Gencheff et al. |
| 5,423,808 A | 6/1995 | Edwards et al. |
| 5,423,810 A | 6/1995 | Goble et al. |
| 5,425,364 A | 6/1995 | Imran |
| 5,437,662 A | 8/1995 | Nardella |
| 5,437,664 A | 8/1995 | Cohen et al. |
| 5,472,443 A | 12/1995 | Cordis et al. |
| 5,484,400 A | 1/1996 | Edwards et al. |
| 5,496,312 A | 3/1996 | Klicek |
| 5,540,681 A | 7/1996 | Strul et al. |
| 5,540,684 A | 7/1996 | Hassler |
| 5,562,721 A | 10/1996 | Marchlinski et al. |
| 5,571,147 A | 11/1996 | Sluijter et al. |
| 5,573,533 A | 11/1996 | Strul |
| 5,584,830 A | 12/1996 | Ladd et al. |
| 5,588,964 A | 12/1996 | Imran et al. |
| 5,599,345 A | 2/1997 | Edwards et al. |
| 5,626,576 A | 5/1997 | Janssen |
| 5,658,619 A | 8/1997 | Kirschner et al. |
| 5,672,174 A | 9/1997 | Gough et al. |
| 5,688,266 A | 11/1997 | Edwards et al. |
| 5,697,882 A | 12/1997 | Eggers et al. |
| 5,697,925 A | 12/1997 | Taylor |
| 5,700,282 A | 12/1997 | Zabara |
| 5,702,386 A | 12/1997 | Stern et al. |
| 5,707,400 A | 1/1998 | Terry, Jr. et al. |
| 5,735,846 A | 4/1998 | Panescu et al. |
| 5,743,903 A | 4/1998 | Stern et al. |
| 5,755,715 A | 5/1998 | Stern et al. |
| 5,769,847 A | 6/1998 | Panescu et al. |
| 5,772,590 A | 6/1998 | Webster, Jr. |
| 5,810,802 A | 9/1998 | Panescu et al. |
| 5,817,092 A | 10/1998 | Behl |
| 5,817,093 A | 10/1998 | Williamson, IV et al. |
| 5,860,974 A | 1/1999 | Abele |
| 5,865,787 A | 2/1999 | Shapland et al. |
| 5,868,737 A | 2/1999 | Taylor et al. |
| 5,871,481 A | 2/1999 | Kannenberg et al. |
| 5,893,885 A | 4/1999 | Webster, Jr. |
| 5,906,614 A | 5/1999 | Stern et al. |
| 5,907,589 A | 5/1999 | Koifman et al. |
| 5,941,869 A | 8/1999 | Patterson et al. |
| 5,944,710 A | 8/1999 | Dev et al. |
| 5,954,719 A | 9/1999 | Chen et al. |
| 5,957,969 A | 9/1999 | Warner et al. |
| 5,976,128 A | 11/1999 | Schilling et al. |
| 5,983,141 A | 11/1999 | Sluijter et al. |
| 6,004,269 A | 12/1999 | Crowley et al. |
| 6,006,755 A | 12/1999 | Edwards |
| 6,009,877 A | 1/2000 | Edwards |
| 6,023,638 A | 2/2000 | Swanson |
| 6,024,740 A | 2/2000 | Lesh et al. |
| 6,036,687 A | 3/2000 | Laufer et al. |
| 6,039,731 A | 3/2000 | Taylor et al. |
| 6,066,134 A | 5/2000 | Eggers et al. |
| 6,080,149 A | 6/2000 | Huang et al. |
| 6,091,995 A | 7/2000 | Ingle et al. |
| 6,099,524 A | 8/2000 | Lipson et al. |
| 6,113,592 A | 9/2000 | Taylor |
| 6,117,101 A | 9/2000 | Diederich et al. |
| 6,123,702 A | 9/2000 | Swanson et al. |
| 6,135,999 A | 10/2000 | Fanton et al. |
| 6,142,993 A | 11/2000 | Whayne et al. |
| 6,149,620 A | 11/2000 | Baker et al. |
| 6,161,048 A | 12/2000 | Sluijter et al. |
| 6,183,468 B1 | 2/2001 | Swanson et al. |
| 6,197,021 B1 | 3/2001 | Panescu et al. |
| 6,210,403 B1 | 4/2001 | Klicek |
| 6,212,426 B1 | 4/2001 | Swanson |
| 6,217,573 B1 | 4/2001 | Webster |
| 6,219,577 B1 | 4/2001 | Brown, III et al. |
| 6,224,592 B1 | 5/2001 | Eggers et al. |
| 6,238,387 B1 | 5/2001 | Miller, III |
| 6,245,065 B1 | 6/2001 | Panescu et al. |
| 6,246,912 B1 | 6/2001 | Sluijter et al. |
| 6,273,886 B1 | 8/2001 | Edwards et al. |
| 6,283,951 B1 | 9/2001 | Flaherty et al. |
| 6,292,695 B1 | 9/2001 | Webster, Jr. et al. |
| 6,293,941 B1 | 9/2001 | Strul et al. |
| 6,314,325 B1 | 11/2001 | Fitz |
| 6,322,558 B1 | 11/2001 | Taylor et al. |
| 6,322,559 B1 | 11/2001 | Daulton et al. |
| 6,358,246 B1 | 3/2002 | Behl et al. |
| 6,405,732 B1 | 6/2002 | Edwards et al. |
| 6,413,255 B1 | 7/2002 | Stern |
| 6,423,057 B1 | 7/2002 | He et al. |
| 6,428,537 B1 | 8/2002 | Swanson et al. |
| 6,451,015 B1 | 9/2002 | Rittman, III et al. |
| 6,464,696 B1 | 10/2002 | Oyama et al. |
| 6,488,678 B2 | 12/2002 | Sherman |
| 6,488,679 B1 | 12/2002 | Swanson et al. |
| 6,494,880 B1 | 12/2002 | Swanson et al. |
| 6,500,172 B1 | 12/2002 | Panescu et al. |

(56) References Cited

U.S. PATENT DOCUMENTS

| | | |
|---|---|---|
| 6,506,189 B1 | 1/2003 | Rittman, III et al. |
| 6,508,815 B1 | 1/2003 | Strul et al. |
| 6,511,476 B2 | 1/2003 | Hareyama |
| 6,514,226 B1 | 2/2003 | Levin et al. |
| 6,514,248 B1 | 2/2003 | Eggers et al. |
| 6,517,811 B2 | 2/2003 | John et al. |
| 6,522,926 B1 | 2/2003 | Kieval et al. |
| 6,542,781 B1 | 4/2003 | Koblish et al. |
| 6,558,378 B2 | 5/2003 | Sherman et al. |
| 6,558,382 B2 | 5/2003 | Jahns et al. |
| 6,562,034 B2 | 5/2003 | Edwards et al. |
| 6,616,624 B1 | 9/2003 | Kieval |
| 6,622,731 B2 | 9/2003 | Daniel et al. |
| 6,635,054 B2 | 10/2003 | Fjield et al. |
| 6,635,057 B2 | 10/2003 | Harano et al. |
| 6,640,120 B1 | 10/2003 | Swanson et al. |
| 6,648,883 B2 | 11/2003 | Francischelli et al. |
| 6,666,862 B2 | 12/2003 | Jain et al. |
| 6,669,655 B1 | 12/2003 | Acker et al. |
| 6,679,269 B2 | 1/2004 | Swanson |
| 6,682,527 B2 | 1/2004 | Strul |
| 6,685,648 B2 | 2/2004 | Flaherty et al. |
| 6,685,700 B2 | 2/2004 | Behl et al. |
| 6,711,444 B2 | 3/2004 | Koblish |
| 6,730,079 B2 | 5/2004 | Lovewell |
| 6,733,498 B2 | 5/2004 | Paton et al. |
| 6,736,835 B2 | 5/2004 | Pellegrino et al. |
| 6,752,804 B2 | 6/2004 | Simpson et al. |
| 6,752,805 B2 | 6/2004 | Maguire et al. |
| 6,761,716 B2 | 7/2004 | Kadhiresan et al. |
| 6,796,981 B2 | 9/2004 | Wham et al. |
| 6,845,267 B2 | 1/2005 | Harrison et al. |
| 6,849,073 B2 | 2/2005 | Hoey et al. |
| 6,850,801 B2 | 2/2005 | Kieval et al. |
| 6,855,141 B2 | 2/2005 | Lovewell |
| 6,855,142 B2 | 2/2005 | Harano et al. |
| 6,869,431 B2 | 3/2005 | Maguire et al. |
| 6,885,888 B2 | 4/2005 | Rezai |
| 6,893,436 B2 | 5/2005 | Woodard et al. |
| 6,936,047 B2 | 8/2005 | Nasab et al. |
| 6,939,346 B2 | 9/2005 | Kannenberg et al. |
| 6,955,675 B2 | 10/2005 | Jain |
| 6,962,587 B2 | 11/2005 | Johnson et al. |
| 6,989,010 B2 | 1/2006 | Francischelli et al. |
| 7,001,379 B2 | 2/2006 | Behl et al. |
| 7,001,381 B2 | 2/2006 | Harano et al. |
| 7,004,911 B1 | 2/2006 | Tu et al. |
| 7,008,417 B2 | 3/2006 | Eick |
| 7,025,764 B2 | 4/2006 | Paton et al. |
| 7,029,470 B2 | 4/2006 | Francischelli et al. |
| 7,066,933 B2 | 6/2006 | Hagg |
| 7,076,399 B2 | 7/2006 | Godara |
| 7,104,985 B2 | 9/2006 | Martinelli |
| 7,108,694 B2 | 9/2006 | Miura et al. |
| 7,118,568 B2 | 10/2006 | Hassett et al. |
| 7,131,445 B2 | 11/2006 | Amoah |
| 7,137,980 B2 | 11/2006 | Buysse et al. |
| 7,149,574 B2 | 12/2006 | Yun et al. |
| 7,162,303 B2 | 1/2007 | Levin et al. |
| 7,169,144 B2 | 1/2007 | Hoey et al. |
| 7,221,979 B2 | 5/2007 | Zhou et al. |
| 7,226,447 B2 | 6/2007 | Uchida et al. |
| 7,247,155 B2 | 7/2007 | Hoey et al. |
| 7,250,048 B2 | 7/2007 | Francischelli et al. |
| 7,251,531 B2 | 7/2007 | Mosher et al. |
| 7,258,688 B1 | 8/2007 | Shah et al. |
| 7,364,578 B2 | 4/2008 | Francischelli et al. |
| 7,367,972 B2 | 5/2008 | Francischelli et al. |
| 7,381,200 B2 | 6/2008 | Katoh et al. |
| 7,390,894 B2 | 6/2008 | Weinshilboum et al. |
| 7,412,285 B2 | 8/2008 | Schroeppel et al. |
| 7,429,261 B2 | 9/2008 | Kunis et al. |
| 7,533,002 B2 | 5/2009 | Godara |
| 7,582,084 B2 | 9/2009 | Swanson et al. |
| 7,596,469 B2 | 9/2009 | Godara |
| 7,617,005 B2 | 11/2009 | Demarais et al. |
| 7,620,451 B2 | 11/2009 | Demarais et al. |
| 7,647,115 B2 | 1/2010 | Levin et al. |
| 7,651,492 B2 | 1/2010 | Wham |
| 7,653,438 B2 | 1/2010 | Deem et al. |
| 7,717,909 B2 | 5/2010 | Strul et al. |
| 7,717,948 B2 | 5/2010 | Demarais et al. |
| 7,778,703 B2 | 8/2010 | Gross et al. |
| 7,792,589 B2 | 9/2010 | Levy et al. |
| 7,799,020 B2 | 9/2010 | Shores et al. |
| 7,824,399 B2 | 11/2010 | Francischelli et al. |
| 7,837,679 B2 | 11/2010 | Biggs et al. |
| 7,842,076 B2 | 11/2010 | Zikorus et al. |
| 7,846,160 B2 | 12/2010 | Payne et al. |
| 7,850,685 B2 | 12/2010 | Kunis et al. |
| 7,887,534 B2 | 2/2011 | Hamel et al. |
| 7,901,400 B2 | 3/2011 | Wham et al. |
| 7,922,714 B2 | 4/2011 | Stevens-Wright |
| 7,927,328 B2 | 4/2011 | Orszulak et al. |
| 7,959,626 B2 | 6/2011 | Hong et al. |
| 7,963,962 B2 | 6/2011 | Thompson et al. |
| 7,972,328 B2 | 7/2011 | Wham et al. |
| 7,976,540 B2 | 7/2011 | Daw et al. |
| 8,007,495 B2 | 8/2011 | McDaniel et al. |
| 8,048,070 B2 | 11/2011 | O'Brien et al. |
| 8,058,771 B2 | 11/2011 | Giordano et al. |
| 8,080,008 B2 | 12/2011 | Wham et al. |
| 8,086,315 B2 | 12/2011 | Schwartz et al. |
| 8,095,212 B2 | 1/2012 | Sato |
| 8,105,323 B2 | 1/2012 | Buysse et al. |
| 8,131,371 B2 | 3/2012 | Demarals et al. |
| 8,131,372 B2 | 3/2012 | Levin et al. |
| 8,140,170 B2 | 3/2012 | Rezai et al. |
| 8,145,317 B2 | 3/2012 | Demarais et al. |
| 8,147,485 B2 | 4/2012 | Wham et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,152,801 B2 | 4/2012 | Goldberg et al. |
| 8,152,802 B2 | 4/2012 | Podhajsky et al. |
| 8,162,932 B2 | 4/2012 | Podhajsky et al. |
| 8,175,711 B2 | 5/2012 | Demarais et al. |
| 8,241,275 B2 | 8/2012 | Hong et al. |
| 8,273,084 B2 | 9/2012 | Kunis et al. |
| 8,340,763 B2 | 12/2012 | Levin et al. |
| 8,876,813 B2 | 11/2014 | Min et al. |
| 8,909,316 B2 | 12/2014 | Ng |
| 9,028,472 B2 | 5/2015 | Mathur et al. |
| 9,037,259 B2 | 5/2015 | Mathur |
| 9,155,589 B2 | 10/2015 | Jenson |
| 9,561,070 B2 | 2/2017 | Brotz et al. |
| 2001/0014802 A1 | 8/2001 | Tu |
| 2002/0058933 A1* | 5/2002 | Christopherson ...... A61B 18/14 606/34 |
| 2002/0062123 A1 | 5/2002 | McClurken et al. |
| 2002/0087208 A1 | 7/2002 | Koblish et al. |
| 2002/0091381 A1 | 7/2002 | Edwards |
| 2002/0091385 A1 | 7/2002 | Paton et al. |
| 2002/0107515 A1 | 8/2002 | Edwards et al. |
| 2002/0139379 A1 | 10/2002 | Edwards et al. |
| 2002/0143302 A1 | 10/2002 | Hinchliffe et al. |
| 2002/0165532 A1 | 11/2002 | Hill et al. |
| 2002/0183682 A1 | 12/2002 | Darvish et al. |
| 2003/0004510 A1 | 1/2003 | Wham et al. |
| 2003/0050635 A1 | 3/2003 | Truckai et al. |
| 2003/0050681 A1 | 3/2003 | Pianca et al. |
| 2003/0060858 A1 | 3/2003 | Kieval et al. |
| 2003/0065322 A1 | 4/2003 | Panescu et al. |
| 2003/0074039 A1 | 4/2003 | Puskas |
| 2003/0125790 A1 | 7/2003 | Fastovsky et al. |
| 2003/0144605 A1 | 7/2003 | Burbank et al. |
| 2003/0181897 A1 | 9/2003 | Thomas et al. |
| 2003/0195507 A1 | 10/2003 | Stewart et al. |
| 2003/0199863 A1 | 10/2003 | Swanson et al. |
| 2003/0216792 A1 | 11/2003 | Levin et al. |
| 2003/0229340 A1 | 12/2003 | Sherry et al. |
| 2003/0233099 A1 | 12/2003 | Danaek et al. |
| 2004/0010289 A1 | 1/2004 | Biggs et al. |
| 2004/0059328 A1 | 3/2004 | Daniel et al. |

(56) References Cited

U.S. PATENT DOCUMENTS

| | | |
|---|---|---|
| 2004/0068304 A1 | 4/2004 | Paton et al. |
| 2004/0122420 A1 | 6/2004 | Amoah |
| 2004/0167509 A1 | 8/2004 | Taimisto |
| 2004/0215186 A1 | 10/2004 | Cornelius et al. |
| 2005/0021020 A1 | 1/2005 | Blaha |
| 2005/0080409 A1 | 4/2005 | Young et al. |
| 2005/0090815 A1 | 4/2005 | Francischelli et al. |
| 2005/0096647 A1 | 5/2005 | Steinke et al. |
| 2005/0124977 A1 | 6/2005 | Gonzalez et al. |
| 2005/0187579 A1 | 8/2005 | Danek et al. |
| 2005/0228460 A1 | 10/2005 | Levin et al. |
| 2005/0283148 A1 | 12/2005 | Janssen et al. |
| 2005/0288662 A1 | 12/2005 | Uchida et al. |
| 2005/0288730 A1 | 12/2005 | Deem et al. |
| 2006/0025765 A1 | 2/2006 | Landman et al. |
| 2006/0058711 A1 | 3/2006 | Harhen et al. |
| 2006/0085054 A1 | 4/2006 | Zikorus et al. |
| 2006/0095029 A1 | 5/2006 | Young et al. |
| 2006/0095032 A1 | 5/2006 | Jackson et al. |
| 2006/0100618 A1 | 5/2006 | Chan et al. |
| 2006/0106375 A1 | 5/2006 | Werneth et al. |
| 2006/0142753 A1 | 6/2006 | Francischelli et al. |
| 2006/0161148 A1 | 7/2006 | Behnke |
| 2006/0206150 A1 | 9/2006 | Demarais et al. |
| 2006/0212076 A1 | 9/2006 | Demarais et al. |
| 2006/0217707 A1* | 9/2006 | Daniel ............... A61B 18/1477 606/50 |
| 2006/0271111 A1 | 11/2006 | Demarais et al. |
| 2006/0282071 A1 | 12/2006 | Utley et al. |
| 2007/0010860 A1 | 1/2007 | Gafni et al. |
| 2007/0016274 A1 | 1/2007 | Boveja et al. |
| 2007/0049999 A1 | 3/2007 | Esch et al. |
| 2007/0050001 A1* | 3/2007 | Luttich ................. A61B 18/12 607/102 |
| 2007/0083193 A1 | 4/2007 | Werneth et al. |
| 2007/0083195 A1 | 4/2007 | Werneth et al. |
| 2007/0112342 A1 | 5/2007 | Pearson et al. |
| 2007/0129720 A1 | 6/2007 | Demarais et al. |
| 2007/0135875 A1 | 6/2007 | Demarais et al. |
| 2007/0167943 A1 | 7/2007 | Janssen et al. |
| 2007/0173805 A1 | 7/2007 | Weinberg et al. |
| 2007/0203481 A1 | 8/2007 | Gregg et al. |
| 2007/0208333 A1 | 9/2007 | Uchida et al. |
| 2007/0265687 A1 | 11/2007 | Deem et al. |
| 2007/0270688 A1 | 11/2007 | Gelbart et al. |
| 2007/0270795 A1 | 11/2007 | Francischelli et al. |
| 2008/0015562 A1 | 1/2008 | Hong et al. |
| 2008/0071257 A1 | 3/2008 | Kotmel et al. |
| 2008/0077126 A1 | 3/2008 | Rashidi |
| 2008/0101356 A1 | 5/2008 | Babbar et al. |
| 2008/0125775 A1 | 5/2008 | Morris |
| 2008/0147057 A1 | 6/2008 | Eisele |
| 2008/0188912 A1 | 8/2008 | Stone et al. |
| 2008/0188913 A1 | 8/2008 | Stone et al. |
| 2008/0228181 A1 | 9/2008 | Godara et al. |
| 2008/0255642 A1 | 10/2008 | Zarins et al. |
| 2008/0262489 A1 | 10/2008 | Steinke |
| 2008/0281312 A1 | 11/2008 | Werneth et al. |
| 2008/0281322 A1 | 11/2008 | Werneth et al. |
| 2008/0300589 A1 | 12/2008 | Paul et al. |
| 2008/0319513 A1 | 12/2008 | Pu et al. |
| 2009/0030477 A1 | 1/2009 | Jarrard |
| 2009/0036948 A1 | 2/2009 | Levin et al. |
| 2009/0062873 A1 | 3/2009 | Wu et al. |
| 2009/0076409 A1 | 3/2009 | Wu et al. |
| 2009/0182323 A1 | 7/2009 | Eder et al. |
| 2009/0182325 A1 | 7/2009 | Werneth et al. |
| 2009/0299365 A1 | 12/2009 | Stewart et al. |
| 2010/0137860 A1 | 6/2010 | Demarais et al. |
| 2010/0137952 A1 | 6/2010 | Demarais et al. |
| 2010/0179533 A1 | 7/2010 | Podhajsky |
| 2010/0179538 A1 | 7/2010 | Podhajsky |
| 2010/0191112 A1 | 7/2010 | Demarais et al. |
| 2010/0211063 A1 | 8/2010 | Wham et al. |
| 2010/0222851 A1 | 9/2010 | Deem et al. |
| 2010/0222854 A1 | 9/2010 | Demarais et al. |
| 2010/0228247 A1 | 9/2010 | Paul et al. |
| 2010/0324548 A1 | 12/2010 | Godara et al. |
| 2011/0077641 A1 | 3/2011 | Dunning |
| 2011/0087214 A1 | 4/2011 | Giordano et al. |
| 2011/0087217 A1 | 4/2011 | Yates et al. |
| 2011/0112400 A1 | 5/2011 | Emery et al. |
| 2011/0130755 A1 | 6/2011 | Bhushan et al. |
| 2011/0190755 A1 | 8/2011 | Mathur et al. |
| 2011/0230876 A1 | 9/2011 | Hong et al. |
| 2011/0270120 A1 | 11/2011 | McFarlin et al. |
| 2011/0270237 A1 | 11/2011 | Werneth et al. |
| 2011/0270247 A1 | 11/2011 | Sherman |
| 2012/0041502 A1 | 2/2012 | Schwartz et al. |
| 2012/0095461 A1 | 4/2012 | Herscher et al. |
| 2012/0101538 A1 | 4/2012 | Ballakur et al. |
| 2012/0130289 A1 | 5/2012 | Demarais et al. |
| 2012/0130345 A1 | 5/2012 | Levin et al. |
| 2012/0136346 A1 | 5/2012 | Condie et al. |
| 2012/0136348 A1 | 5/2012 | Condie et al. |
| 2012/0143097 A1 | 6/2012 | Pike |
| 2012/0150169 A1 | 6/2012 | Zielinksi et al. |
| 2012/0172837 A1 | 7/2012 | Demarais et al. |
| 2012/0197243 A1 | 8/2012 | Sherman et al. |
| 2012/0310241 A1 | 12/2012 | Orszulak |
| 2013/0006228 A1 | 1/2013 | Johnson et al. |
| 2013/0006235 A1 | 1/2013 | Podhajsky et al. |
| 2013/0123778 A1 | 5/2013 | Richardson et al. |
| 2013/0165764 A1 | 6/2013 | Scheuermann et al. |
| 2013/0172878 A1 | 7/2013 | Smith |
| 2014/0128865 A1 | 5/2014 | Gross |
| 2014/0194866 A1 | 7/2014 | Wang |
| 2014/0213873 A1 | 7/2014 | Wang |
| 2014/0221805 A1 | 8/2014 | Wang |
| 2014/0228614 A1 | 8/2014 | Stopek |
| 2014/0228829 A1 | 8/2014 | Schmitt et al. |
| 2014/0228858 A1 | 8/2014 | Stopek |
| 2014/0236137 A1 | 8/2014 | Tran et al. |
| 2014/0236138 A1 | 8/2014 | Tran et al. |
| 2014/0246465 A1 | 9/2014 | Peterson et al. |
| 2014/0249524 A1 | 9/2014 | Kocur |
| 2014/0257266 A1 | 9/2014 | Kasprzyk et al. |
| 2014/0266235 A1 | 9/2014 | Mathur |
| 2014/0275924 A1 | 9/2014 | Min et al. |
| 2014/0276124 A1 | 9/2014 | Cholette et al. |
| 2014/0276733 A1 | 9/2014 | VanScoy et al. |
| 2014/0276742 A1 | 9/2014 | Nabutovsky |
| 2014/0276746 A1 | 9/2014 | Nabutovsky et al. |
| 2014/0276755 A1 | 9/2014 | Cao et al. |
| 2014/0276762 A1 | 9/2014 | Parsonage |
| 2014/0276766 A1 | 9/2014 | Brotz et al. |
| 2014/0276767 A1 | 9/2014 | Brotz et al. |
| 2014/0276773 A1 | 9/2014 | Brotz et al. |
| 2014/0316400 A1 | 10/2014 | Blix et al. |
| 2014/0316496 A1 | 10/2014 | Masson et al. |
| 2014/0330266 A1 | 11/2014 | Thompson et al. |
| 2014/0336637 A1 | 11/2014 | Agrawal et al. |
| 2015/0005764 A1 | 1/2015 | Hanson et al. |
| 2015/0025524 A1 | 1/2015 | Nabutovsky |
| 2015/0245867 A1 | 9/2015 | Gross |
| 2016/0310201 A1 | 10/2016 | Brotz et al. |
| 2017/0007157 A1 | 1/2017 | Gross et al. |
| 2017/0007158 A1 | 1/2017 | Gross et al. |

FOREIGN PATENT DOCUMENTS

| | | |
|---|---|---|
| EP | 1169976 | 1/2002 |
| EP | 768841 | 3/2003 |
| EP | 1366724 | 1/2006 |
| EP | 2037840 | 3/2009 |
| EP | 2460486 | 6/2012 |
| EP | 2747691 | 7/2014 |
| EP | 2797535 | 11/2014 |
| EP | 2914192 | 9/2015 |
| EP | 2967702 | 1/2016 |
| EP | 2967703 | 1/2016 |
| EP | 2967728 | 1/2016 |
| EP | 2967729 | 1/2016 |

(56) References Cited

FOREIGN PATENT DOCUMENTS

| | | |
|---|---|---|
| EP | 2967733 | 1/2016 |
| EP | 2968931 | 1/2016 |
| EP | 2991575 | 3/2016 |
| EP | 3158961 | 4/2017 |
| JP | H08504531 | 5/1996 |
| JP | H1071037 | 3/1998 |
| JP | 2011505929 | 3/2011 |
| JP | 6122206 | 4/2017 |
| WO | WO1993008757 | 5/1993 |
| WO | WO-1994007446 | 4/1994 |
| WO | WO1994010922 | 5/1994 |
| WO | WO-1995025472 | 9/1995 |
| WO | WO-1995031142 | 11/1995 |
| WO | WO-1995031243 | 11/1995 |
| WO | WO1996000036 | 1/1996 |
| WO | WO1996039086 | 12/1996 |
| WO | WO1997004702 | 2/1997 |
| WO | WO-1997018853 | 5/1997 |
| WO | WO-1997036548 | 10/1997 |
| WO | WO1997040882 | 11/1997 |
| WO | WO-1998042403 | 10/1998 |
| WO | WO1998042403 | 10/1998 |
| WO | WO-1999000060 | 1/1999 |
| WO | WO1999000060 | 1/1999 |
| WO | WO-1999002096 | 1/1999 |
| WO | WO1999060923 | 12/1999 |
| WO | WO2000015130 | 3/2000 |
| WO | WO-2000056237 | 9/2000 |
| WO | WO2000122897 | 4/2001 |
| WO | WO-2001022897 | 4/2001 |
| WO | WO-2001070114 | 9/2001 |
| WO | WO-2003022167 | 3/2003 |
| WO | WO-2003082080 | 10/2003 |
| WO | WO-2005030072 | 4/2005 |
| WO | WO-2005041748 | 5/2005 |
| WO | WO2005051215 | 6/2005 |
| WO | WO-2005110528 | 11/2005 |
| WO | WO-2006041881 | 4/2006 |
| WO | WO2006041881 | 4/2006 |
| WO | WO2006080982 | 8/2006 |
| WO | WO-2006105121 | 10/2006 |
| WO | WO-2007008954 | 1/2007 |
| WO | WO2007067941 | 6/2007 |
| WO | WO-2007078997 | 7/2007 |
| WO | WO-2008003058 | 1/2008 |
| WO | WO-2008049084 | 4/2008 |
| WO | WO2008101356 | 8/2008 |
| WO | WO2010078175 | 7/2010 |
| WO | WO2011017168 | 2/2011 |
| WO | WO2011126580 | 10/2011 |
| WO | WO2011144911 | 11/2011 |
| WO | WO2012024631 | 2/2012 |
| WO | WO2012054762 | 4/2012 |
| WO | WO2013030743 | 3/2013 |
| WO | WO2013101485 | 7/2013 |
| WO | WO2014029355 | 2/2014 |
| WO | WO2014059165 | 4/2014 |
| WO | WO2014068577 | 5/2014 |
| WO | WO2014124241 | 8/2014 |
| WO | WO2014149550 | 9/2014 |
| WO | WO2014149552 | 9/2014 |
| WO | WO2014149553 | 9/2014 |
| WO | WO2014149690 | 9/2014 |
| WO | WO2014150425 | 9/2014 |
| WO | WO2014150432 | 9/2014 |
| WO | WO2014150441 | 9/2014 |
| WO | WO2014150455 | 9/2014 |
| WO | WO2014158713 | 10/2014 |
| WO | WO2014163990 | 10/2014 |
| WO | WO2014179110 | 11/2014 |
| WO | WO2014182946 | 11/2014 |

OTHER PUBLICATIONS

Bhandari, et al. "Loin Pain Hematuria Syndrome: Pain Control with RFA to the Splanchanic Plexus," The Pain Clinc, 2000, vol. 12, No. 4, pp. 323-327.
Search Report dated Jul. 23, 2009 for European Application No. 07799148.7.
Search Report dated Oct. 17, 2013 for European Application No. 13159256.
Ahmed, Humera et al., Renal Sympathetic Denervation Using an Irrigated Radiofrequency Ablation Catheter for the Management of Drug-Resistant Hypertension, JACC Cardiovascular Interventions, vol. 5, No. 7, 2012, pp. 758-765.
Avitall et al., "The creation of linear contiguous lesions in the atria with an expandable loop catheter," Journal of the American College of Cardiology, 1999; 33; pp. 972-984.
Beale et al., "Minimally Invasive Treatment for Varicose Veins: A Review of Endovenous Laser Treatment and Radiofrequency Ablation". Lower Extremity Wounds 3(4), 2004, 10 pages.
Blessing, Erwin et al., Cardiac Ablation and Renal Denervation Systems Have Distinct Purposes and Different Technical Requirements, JACC Cardiovascular Interventions, vol. 6, No. 3, 2013, 1 page.
ClinicalTrials.gov, Renal Denervation in Patients with uncontrolled Hypertension in Chinese (2011), 6pages. www.clinicaltrials.gov/ct2/show/NCT01390831.
Dodge, et al., "Lumen Diameter of Normal Human Coronary Arteries Influence of Age, Sex, Anatomic Variation, and Left Ventricular Hypertrophy or Dilation", Circulation, 1992, vol. 86 (1), 232-246 pp.
Excerpt of Operator's Manual of Boston Scientific's EPT-1000 XP Cardiac Ablation Controller & Accessories, Version of Apr. 2003, (6 pages).
Excerpt of Operator's Manual of Boston Scientific's Maestro 30000 Cardiac Ablation System, Version of Oct. 17, 2005 , (4 pages).
Holmes et al., Pulmonary Vein Stenosis Complicating Ablation for Atrial Fibrillation: Clinical Spectrum and Interventional Considerations, JACC: Cardiovascular Interventions, 2: 4, 2009, 10 pages.
Kandarpa, Krishna et al., "Handbook of Interventional Radiologic Procedures", Third Edition, pp. 194-210 (2002).
Mount Sinai School of Medicine clinical trial for Impact of Renal Sympathetic Denervation of Chronic Hypertension, Mar. 2013, 11 pages. http://clinicaltrials.gov/ct2/show/NCT01628198.
Oppositin to European U.S. Pat. No. 2465470, Granted Oct. 28, 2015, Date of Opposition Jul. 27, 2016, 34 pp.
Opposition to European Patent No. EP1802370, Granted Jan. 5, 2011, Date of Opposition Oct. 5, 2011, 20 pages.
Opposition to European Patent No. EP2037840, Granted Dec. 7, 2011, Date of Opposition Sep. 7, 2012, 25 pages.
Opposition to European Patent No. EP2092957, Granted Jan. 5, 2011, Date of Opposition Oct. 5, 2011, 26 pages.
Oz, Mehmet, Pressure Relief, TIME, Jan. 9, 2012, 2 pages. <www.time.come/time/printout/0,8816,2103278,00.html>.
Papademetriou, Vasilios, Renal Sympathetic Denervation for the Treatment of Difficult-to-Control or Resistant Hypertension, Int. Journal of Hypertension, 2011, 8 pages.
Pieper et al., "Design and Implementation of a New Computerized System for Intraoperative Cardiac Mapping" Journal of Applied Physiology, 1991, vol. 71 (4), pp. 1529-1539.
Prochnau, Dirk et al., Catheter-based renal denervation for drug-resistant hypertension by using a standard electrophysiology catheter; Euro Intervention 2012, vol. 7, pp. 1077-1080.
Purerfellner, Helmut et al., Incidence, Management, and Outcome in Significant Pulmonary Vein Stenosis Complicating Ablation for Atrial Fibrillation, Am. J. Cardiol , 93, Jun. 1, 2004, 4 pages.
Purerfellner, Helmut et al., Pulmonary Vein Stenosis Following Catheter Ablation of Atrial Fibrillation, Curr. Opin. Cardio. 20 :484-490, 2005.
Remo, et al., "Safety and Efficacy of Renal Denervation as a Novel Treatment of Ventricular Tachycardia Storm in Patients with Cardiomyopathy" Heart Rhythm, 2014, 11(4), pp. 541-546.

(56) References Cited

OTHER PUBLICATIONS

Schneider, Peter A., "Endovascular Skills—Guidewire and Catheter Skills for Endovascular Surgery," Second Edition Revised and Expanded, 10 pages, (2003).
ThermoCool Irrigated Catheter and Integrated Ablation System, Biosense Webster (2006), 6 pages.
Tsao, Hsuan-Ming, Evaluation of Pulmonary Vein Stenosis after Catheter Ablation of Atrial Fibrillation, Cardiac Electrophysiology Review, 6, 2002, 4 pages.
U.S. Appl. No. 11/363,867, filed Feb. 27, 2006, 70 pp.
U.S. Appl. No. 60/813,589, filed Dec. 29, 2005, 62 pp.
U.S. Appl. No. 60/852,787, filed Oct. 18, 2006, 112 pp.
Ureter, https://en.wikipedia.org/wiki/Ureter, Jun. 2016, 6 pp.
Wittkampf et al., "Control of radiofrequency lesion size by power regulation," Journal of the American Heart Associate, 1989, 80: pp. 962-968.
Zheng et al., "Comparison of the temperature profile and pathological effect at unipolar, bipolar and phased radiofrequency current configurations," Journal of Interventional Cardiac Electrophysiology, 2001, pp. 401-410.
"2011 Edison Award Winners." Edison Awards: Honoring Innovations & Innovators, 2011, 6 pages, <http://www.edisonawards.com/BestNewProduct_2011.php>.
"2012 top 10 advances in heart disease and stroke research: American Heart Association/America Stroke Association Top 10 Research Report." American Heart Association, Dec. 17, 2012, 5 pages, <http://newsroom.heart.org/news/2012-top-10-advances-in-heart-241901>.
"Ardian(R) Receives 2010 EuroPCR Innovation Award and Demonstrates Further Durability of Renal Denervation Treatment for Hypertension." PR Newswire, Jun. 3, 2010, 2 pages, <http://www.prnewswire.com/news-releases/ardianr-receives-2010-europcr-innovation-award-and-demonstrates-further-durability-of-renal-denervation-treatment-for-hypertension-95545014.html>.
"Boston Scientific to Acquire Vessix Vascular, Inc.: Company to Strengthen Hypertension Program with Acquisition of Renal Denervation Technology." Boston Scientific: Advancing science for life-Investor Relations, Nov. 8, 2012, 2 pages, <http://phx.corporate-ir.net/phoenix.zhtml?c=62272&p=irol-newsArticle&id=1756108>.
"Cleveland Clinic Unveils Top 10 Medical Innovations for 2012: Experts Predict Ten Emerging Technologies that will Shape Health Care Next Year." Cleveland Clinic, Oct. 6, 2011, 2 pages. <http://my.clevelandclinic.org/media_relations/library/2011/2011-10-6-cleveland-clinic-unveils-top-10-medical-innovations-for-2012.aspx>.
"Does renal denervation represent a new treatment option for resistant hypertension?" Interventional News, Aug. 3, 2010, 2 pages. <http://www.cxvascular.com/in-latest-news/interventional-news---latest-news/does-renal-denervation-represent-a-new-treatment-option-for-resistant-hypertension>.
"Iberis—Renal Sympathetic Denervation System: Turning innovation into quality care." [Brochure], Terumo Europe N.V., 2013, Europe, 3 pages.
"Neurotech Reports Announces Winners of Gold Electrode Awards." Neurotech business report, 2009. 1 page. <http://www.neurotechreports.com/pages/goldelectrodes09.html>.
"Quick. Consistent. Controlled. OneShot renal Denervation System" [Brochure], Covidien: positive results for life, 2013, (n.l.), 4 pages.
"Renal Denervation Technology of Vessix Vascular, Inc. been acquired by Boston Scientific Corporation (BSX) to pay up to $425 Million." Vessix Vascular Pharmaceutical Intelligence: A blog specializing in Pharmaceutical Intelligence and Analytics, Nov. 8, 2012, 21 pages, <http://pharmaceuticalintelligence.com/tag/vessix-vascular/>.
"The Edison AwardsTM" Edison Awards: Honoring Innovations & Innovators, 2013, 2 pages, <http://www.edisonawards.com/Awards.php>.
"The Future of Renal denervation for the Treatment of Resistant Hypertension." St. Jude Medical, Inc., 2012, 12 pages.

"Vessix Renal Denervation System: So Advanced It's Simple." [Brochure], Boston Scientific: Advancing science for life, 2013, 6 pages.
Asbell, Penny, "Conductive Keratoplasty for the Correction of Hyperopia." Tr Am Ophth Soc, 2001, vol. 99, 10 pages.
Badoer, Emilio, "Cardiac afferents play the dominant role in renal nerve inhibition elicited by volume expansion in the rabbit." Am J Physiol Regul Integr Comp Physiol, vol. 274, 1998, 7 pages.
Bengel, Frank, "Serial Assessment of Sympathetic Reinnervation After Orthotopic Heart Transplantation: A longitudinal Study Using PET and C-11 Hydroxyephedrine." Circulation, vol. 99, 1999, 7 pages.
Benito, F., et al. "Radiofrequency catheter ablation of accessory pathways in infants." Heart, 78:160-162 (1997).
Bettmann, Michael, Carotid Stenting and Angioplasty: A Statement for Healthcare Professionals From the Councils on Cardiovascular Radiology, Stroke, Cardio-Thoracic and Vascular Surgery, Epidemiology and Prevention, and Clinical Cardiology, American Heart Association, Circulation, vol. 97, 1998, 4 pages.
Bohm, Michael et al., "Rationale and design of a large registry on renal denervation: the Global SYMPLICITY registry." EuroIntervention, vol. 9, 2013, 9 pages.
Brosky, John, "EuroPCR 2013: CE-approved devices line up for renal denervation approval." Medical Device Daily, May 28, 2013, 3 pages, <http://www.medicaldevicedaily.com/servlet/com.accumedia.web.Dispatcher?next=bioWorldHeadlines_article&forceid=83002>.
Curtis, J.J., et al., "Surgical therapy for persistent hypertension after renal transplantation." Transplantation, 1981, 31: 125-128.
Davis, Mark et al., "Effectiveness of Renal Denervation Therapy for Resistant Hypertension." Journal of the American College of Cardiology, vol. 62, No. 3, 2013, 11 pages.
Dibona, G.F. "Sympathetic nervous system and kidney in hypertension." Nephrol and Hypertension, 11: 197-200 (2002).
Dibona, G.F., et al. "Neural control of renal function." Physiol Rev, 77:75-197 (1997).
Dubuc, M., et al., "Feasibility of cardiac cryoablation using a transvenous steerable electrode catheter." J Interv Cardiac Electrophysiol, 2:285-292 (1998).
Final Office Action; U.S. Appl. No. 12/827,700; dated Feb. 5, 2013, 61 pages.
Geisler, Benjamin et al., "Cost-Effectiveness and Clinical Effectiveness of Catheter-Based Renal Denervation for Resistant Hypertension." Journal of the American College of Cardiology, col. 60, No. 14, 2012, 7 pages.
Gelfand, M., et al., "Treatment of renal failure and hypertension." U.S. Appl. No. 60/442,970, filed Jan. 29, 2003, 23 pages.
Gertner, Jon, "Meet the Tech Duo That's Revitalizing the Medical Device Industry." Fast Company, Apr. 15, 2013, 6:00 AM, 17 pages, <http://www.fastcompany.com/3007845/meet-tech-duo-thats-revitalizing-medical-device-industry>.
Golwyn, D. H., Jr., et al. "Percutaneous Transcatheter Renal Ablation with Absolute Ethanol for Uncontrolled Hypertension or Nephrotic Syndrome: Results in 11 Patients with End-Stage Renal Disease." JVIR, 8: 527-533 (1997).
Hall, W. H., et al. "Combined embolization and percutaneous radiofrequency ablation of a solid renal tumor." *Am. J. Roentgenol*,174: 1592-1594 (2000).
Han, Y.-M, et al., "Renal artery embolization with diluted hot contrast medium: An experimental study." J Vasc Interv Radiol, 12: 862-868 (2001).
Hansen, J. M., et al. "The transplanted human kidney does not achieve functional reinnervation." *Clin. Sci*, 87: 13-19 (1994).
Hendee, W. R. et al. "Use of Animals in Biomedical Research: The Challenge and Response." *American Medical Association White Paper* (1988) 39 pages.
Hering, Dagmara et al., "Chronic kidney disease: role of sympathetic nervous system activation and potential benefits of renal denervation." EuroIntervention, vol. 9, 2013, 9 pages.
Huang et al., "Renal denervation prevents and reverses hyperinsulinemia-induced hypertension in rats." Hypertension 32 (1998) pp. 249-254.
Imimdtanz, "Medtronic awarded industry's highest honour for renal denervation system." The official blog of Medtronic Australasia,

(56) References Cited

OTHER PUBLICATIONS

Nov. 12, 2012, 2 pages, <http://97waterlooroad.wordpress.com/2012/11/12/medtronic-awarded-industrys-highest-honour-for-renal-denervation-system/>.
Kaiser, Chris, AHA Lists Year's Big Advances in CV Research, medpage Today, Dec. 18, 2012, 4 pages, <http://www.medpagetoday.com/Cardiology/PCI/36509>.
Kompanowska, E., et al., "Early Effects of renal denervation in the anaesthetised rat: Natriuresis and increased cortical blood flow." J Physiol, 531. 2:527-534 (2001).
Lee, S.J., et al. "Ultrasonic energy in endoscopic surgery." Yonsei Med J, 40:545-549 (1999).
Linz, Dominik et al., "Renal denervation suppresses ventricular arrhythmias during acute ventricular ischemia in pigs." Heart Rhythm, vol. 0, No. 0, 2013, 6 pages.
Lustgarten, D.L.,et al., "Cryothermal ablation: Mechanism of tissue injury and current experience in the treatment of tachyarrhythmias." Progr Cardiovasc Dis, 41:481-498 (1999).
Mabin, Tom et al., "First experience with endovascular ultrasound renal denervation for the treatment of resistant hypertension." EuroIntervention, vol. 8, 2012, 5 pages.
Mahfoud, Felix et al., "Ambulatory Blood Pressure Changes after Renal Sympathetic Denervation in Patients with Resistant Hypertension." Circulation, 2013, 25 pages.
Mahfoud, Felix et al., "Expert consensus document from the European Society of Cardiology on catheter-based renal denervation." European Heart Journal, 2013, 9 pages.
Mahfoud, Felix et al., "Renal Hemodynamics and Renal Function After Catheter-Based Renal Sympathetic Denervation in Patients With Resistant Hypertension." Hypertension, 2012, 6 pages.
Medical-Dictionary.com, Definition of "Animal Model," http://medical-dictionary.com (search "Animal Model"), 2005, 1 page.
Medtronic, Inc., Annual Report (Form 10-K) (Jun. 28, 2011) 44 pages.
Millard, F. C., et al, "Renal Embolization for ablation of function in renal failure and hypertension." Postgraduate Medical Journal, 65, 729-734, (1989).
Oliveira, V., et al., "Renal denervation normalizes pressure and baroreceptor reflex in high renin hypertension in conscious rats." Hypertension, 19:II-17-II-21 (1992).
Ong, K. L., et al. "Prevalence, Awareness, Treatment, and Control of Hypertension Among United States Adults 1999-2004." Hypertension, 49: 69-75 (2007) (originally published online Dec. 11, 2006).
Ormiston, John et al., "First-in-human use of the OneShotTM renal denervation system from Covidien." EuroIntervention, vol. 8, 2013, 4 pages.
Ormiston, John et al., "Renal denervation for resistant hypertension using an irrigated radiofrequency balloon: 12-month results from the Renal Hypertension Ablation System (RHAS) trial." EuroIntervention, vol. 9, 2013, 5 pages.
Pedersen, Amanda, "TCT 2012: Renal denervation device makers play show and tell." Medical Device Daily, Oct. 26, 2012, 2 pages, <http://www.medicaldevicedaily.com/servlet/com.accumedia.web.Dispatcher?next=bioWorldHeadlines_article&forceid=80880>.
Peet, M., "Hypertension and its Surgical Treatment by bilateral supradiaphragmatic splanchnicectomy" Am J Surgery (1948) pp. 48-68.
Renal Denervation (RDN), Symplicity RDN System Common Q&A (2011), 4 pages, http://www.medtronic.com/rdn/mediakit/RDN%20FAQ.pdf.
Schauerte, P., et al."Catheter Ablation of Cardiac Autonomic Nerves for Prevention of Vagal Atrial Fibrillation." Circulation, 102:2774-2780 (2000).
Schlaich, Markus et al., "Renal Denervation in Human Hypertension: Mechanisms, Current Findings, and Future Prospects." Curr Hypertens Rep, vol. 14, 2012, 7 pages.
Schmid, Axel et al., "Does Renal Artery Supply Indicate Treatment Success of Renal Denervation." Cardiovasc Intervent Radiol, vol. 36, 2013, 5 pages.
Schmieder, Roland E. et al., "Updated ESH position paper on interventional therapy of resistant hypertension." EuroIntervention, vol. 9, 2013, 9 pages.
Sievert, Horst, "Novelty Award EuroPCR 2010." Euro PCR, 2010, 15 pages.
Smithwick et al., "Splanchnicectomy for essential hypertension." J. Am. Med. Assn. 152:16 (1953), pp. 1501-1504.
Solis-Herruzo et al., "Effects of lumbar sympathetic block on kidney function in cirrhotic patients with hepatorenal syndrome," J. Hepatol. 5 (1987), pp. 167-173.
Stella, A., et al., "Effects of reversable renal denervation on haemodynamic and excretory functions on the ipsilateral and contralateral kidney in the cat." Hypertension, 4: 181-188 (1986).
Stouffer, G. A. et al., "Catheter-based renal denervation in the treatment of resistant hypertension." Journal of Molecular and Cellular Cardiology, vol. 62, 2013, 6 pages.
Swartz, J.F., et al., "Radiofrequency endocardial catheter ablation of accessory atrioventricular pathway atrial insertion sites." Circulation, 87: 487-499 (1993).
Uchida, F., et al., "Effect of radiofrequency catheter ablation on parasympathetic denervation: A comparison of three different ablation sites." PACE, 21:2517-2521 (1998).
Valente, J.F. "Laparoscopic renal denervation for intractable ADPKD-related pain." Nephrol Dial Transplant, 16: 160 (2001).
Verloop, W. L. et al., "Renal denervation: a new treatment option in resistant arterial hypertension." Neth Heart J., Nov. 30, 2012, 6 pages, <http://www.ncbi.nlm.nih.gov/pmc/articles/PMC3547427/>.
Weinstock, M., et al., "Renal denervation prevents sodium retention and hypertension in salt sensitive rabbits with genetic baroreflex impairment." Clinical Science, 90:287-293 (1996).
Doumas, Michael et al., "Renal Nerve Ablation for Resistant Hypertension: The Dust Has Not Yet Settled." The Journal of Clinical Hypertension. 2014; vol. 16, No. 6, 2 pages.
Messerli, Franz H. et al. "Renal Denervation for Resistant Hypertension: Dead or Alive?" Healio: Cardiology today's Intervention, May/Jun. 2014, 2 pages.
Miller, Reed, "Finding a Future for Renal Denervation With Better Controlled Trials." Pharma & Medtech Business Intelligence, Article # 01141006003, Oct. 6, 2014, 4 pages.
Papademetriou, Vasilios et al., "Catheter-Based Renal Denervation for Resistant Hypertension: 12-Month Results of the EnligHTN I First-in-Human Study Using a Multielectrode Ablation System." Hypertension. 2014; 64: 565-572.
Papademetriou, Vasilios et al., "Renal Nerve Ablation for Resistant Hypertension: How Did We Get Here, Present Status, and Future Directions." Circulation. 2014; 129: 1440-1450.
Papademetriou, Vasilios, "Renal Denervation and Symplicity HTN-3: "Dubium Sapientiae Initium" (Doubt Is the Beginning of Wisdom)", Circulation Research, 2014; 115: 211-214.
Wilcox, Josiah N., Scientific Basis Behind Renal Denervation for the Control of Hypertension, ICI 2012, Dec. 5-6, 2012. 38 pages.
Worthley, Stephen et al., "Safety and efficacy of a multi-electrode renal sympathetic denervation system in resistant hypertension: the EnligHTN I trial." European Heart Journal, vol. 34, 2013, 9 pages.
Worthley, Stephen, "The St. Jude Renal Denervation System Technology and Clinical Review." The University of Adelaide Australia, 2012, 24 pages.
Zuern, Christine S., "Impaired Cardiac Baroflex Sensitivity Predicts Response to Renal Sympathetic Denervation in Patients with Resistant Hypertension." Journal of the American College of Cardiology, 2013, doi: 10.1016/j.jacc.2013.07.046, 24 pages.
Demarais et al., Reexamination Application 95/002,253 U.S. Pat. No. 8,131,371 filed Sep. 13, 2012.
Demarais et al., Reexamination Application 95/002,255 U.S. Pat. No. 7,617,005 filed Sep. 13, 2012.
Demarais et al., Reexamination Application 95/002,292 U.S. Pat. No. 8,175,711 filed Sep. 14, 2012.
Demarais et al., Reexamination Application 95/002,335 U.S. Pat. No. 8,150,520 filed Sep. 14, 2012.
Demarais et al., Reexamination Application 95/002,356 U.S. Pat. No. 8,150,519 filed Sep. 14, 2012.
Demarias et al., Reexamination Application 95/002,327 U.S. Pat. No. 8,145,317 filed Sep. 14, 2012.

(56) References Cited

OTHER PUBLICATIONS

Levin et al. Reexamination Application 95/002,209 U.S. Pat. No. 8,150,518 filed Sep. 13, 2012.
Levin et al., Reexamination Application 95/002,233 U.S. Pat. No. 8,131,372 filed Sep. 13, 2012.
Levin et al., Reexamination Application 95/002,243 U.S. Pat. No. 7,162,303 filed Sep. 13, 2012.
Levin et al., Reexamination Application 95/002,336 U.S. Pat. No. 7,647,115 filed Sep. 14, 2012.
European Search Report dated Jul. 23, 2009; Application No. 09156661.2; Applicant: Ardian, Inc; 6 pages.
European Search Report dated May 22, 2012; Application No. 11191392.7; Applicant: Medtronic Ardain Luxembourg S.a.r.l.; 8 pages.
European Search Report dated May 22, 2012; Application No. 11191394.3; Applicant: Medtronic Ardain Luxembourg S.a.r.l.; 6 pages.
European Search Report dated May 6, 2013; Application No. 10159584.1: Applicant: Medtronic Ardian Luxembourg S.a.r.l.; 9 pages.
International Search Report and Written Opinion dated Aug. 27, 2008; International Application No. PCT/US2007/072396; Applicant: Ardian, Inc.; 5 pages.
U.S. Appl. No. 60/816,999, filed Jun. 28, 2006, 32 pages.
U.S. Appl. No. 60/880,340, filed Jan. 12, 2007, 38 pages.
Allen, E.V., Sympathectomy for essential hypertension, Circulation, 1952, 6:131-140.
Bello-Reuss, E. et al., "Effects of Acute Unilateral Renal Denervation in the Rat," Journal of Clinical Investigation, vol. 56, Jul. 1975, pp. 208-217.
Bello-Reuss, E. et al., "Effects of Renal Sympathetic Nerve Stimulation on Proximal Water and Sodium Reabsorption," Journal of Clinical Investigation, vol. 57, Apr. 1976, pp. 1104-1107.
Curtis, John J. et al., "Surgical Therapy for Persistent Hypertension After Renal Transplantation" Transplantation, 31:125-128 (1981).
Dibona, Gerald F. et al., "Neural Control of Renal Function," Physiological Reviews, vol. 77, No. 1, Jan. 1997, The American Physiological Society 1997, pp. 75-197.
Dibona, Gerald F., "Neural Control of the Kidney—Past, Present and Future," Nov. 4, 2002, Novartis Lecture, Hypertension 2003, 41 part 2, 2002 American Heart Association, Inc., pp. 621-624.
Janssen, Ben J.A. et al., "Effects of Complete Renal Denervation and Selective Afferent Renal Denervation on the Hypertension Induced by Intrarenal Norepinephrine Infusion in Conscious Rats", Journal of Hypertension 1989, 7: 447-455.
Katholi, Richard E., "Renal Nerves in the Pathogenesis of Hypertension in Experimental Animals and Humans," Am J. Physiol. vol. 245, 1983, the American Physiological Society 1983, pp. F1-F14.

Krum, Henry et al., "Catheter-Based Renal Sympathetic Denervation for Resistant Hypertension: A Mulitcentre Safety and Proof-of Principle Cohort Study," Lancet 2009; 373:1275-81.
Krum, et al., "Renal Sympathetic-Nerve Ablation for Uncontrolled Hypertension." New England Journal of Med, Aug. 2009, 361; 9, 3 pages.
Luippold, Gerd et al., "Chronic Renal Denervation Prevents Glomerular Hyperfiltration in Diabetic Rats", Nephrol Dial Transplant, vol. 19, No. 2, 2004, pp. 342-347.
Mahfoud et al. "Treatment strategies for resistant arterial hypertension" Dtsch Arztebl Int. 2011;108:725-731.
Osborn, et al., "Effect of Renal Nerve Stimulation on Renal Blood Flow Autoregulation and Antinatriuresis During Reductions in Renal Perfusion Pressure," Proceedings of the Society for Experimental Biology and Medicine, vol. 168, 77-81, 1981.
Page, I.H. et al., "The Effect of Renal Denervation on Patients Suffering From Nephritis," Feb. 27, 1935;443-458.
Page, I.H. et al., "The Effect of Renal Denervation on the Level of Arterial Blood Pressure and Renal Function in Essential Hypertension," J. Clin Invest. 1934;14:27-30.
Rocha-Singh, "Catheter-Based Sympathetic Renal Denervation," Endovascular Today, Aug. 2009, 4 pages.
Schlaich, M.P. et al., "Renal Denervation as a Therapeutic Approach for Hypertension: Novel Implications for an Old Concept," Hypertension, 2009; 54:1195-1201.
Schlaich, M.P. et al., "Renal Sympathetic-Nerve Ablation for Uncontrolled Hypertension," N Engl J Med 2009; 361(9): 932-934.
Smithwick, R.H. et al., "Splanchnicectomy for Essential Hypertension," Journal Am Med Assn, 1953; 152:1501-1504.
Symplicity HTN-1 Investigators; Krum H, Barman N, Schlaich M, et al. Catheter-based renal sympathetic denervation for resistant hypertension: durability of blood pressure reduction out to 24 months. Hypertension. 2011;57(5):911-917.
Symplicity HTN-2 Investigators, "Renal Sympathetic Denervation in Patients with Treatment-Resistant Hypertension (The Symplicity HTN-2 Trial): A Randomised Controlled Trial"; Lancet, Dec. 4, 2010, vol. 376, pp. 1903-1909.
United States Renal Data System, USRDS 2003 Annual Data Report: Atlas of End-Stage Renal Disease in the United States, National Institutes of Health, National Institute of Diabetes and Digestive and Kidney Diseases, 2003, 593 pages.
Valente, John F. et al., "Laparoscopic Renal Denervation for Intractable ADPKD-Related Pain", Nephrol Dial Transplant (2001) 16: 1 page.
Wagner, C.D. et al., "Very Low Frequency Oscillations in Arterial Blood Pressure After Autonomic Blockade in Conscious Dogs," Feb. 5, 1997, Am J Physiol Regul Integr Comp Physiol 1997, vol. 272, 1997 the American Physiological Society, pp. 2034-2039.
Extended European Search Report for European Application No. 18171535.0, dated Sep. 28, 2018, 17 pages.

\* cited by examiner

DEVICES FOR THERMALLY-INDUCED RENAL NEUROMODULATION

REFERENCE TO RELATED APPLICATIONS

The present application is a continuation of U.S. patent application Ser. No. 12/147,191, filed Jun. 26, 2008, now U.S. Pat. No. 9,345,900 which is a continuation of U.S. patent application Ser. No. 12/159,306, filed Jun. 26, 2008, now abandoned, which is a U.S. National Phase application under 35 U.S.C. § 371 of International Application No. PCT/US2007/072396, filed Jun. 28, 2007, which claims the benefit of the following United States patent applications:
 (a) U.S. Provisional Patent Application No. 60/880,340, filed on Jan. 12, 2007; and
 (b) U.S. Provisional Patent Application No. 60/816,999, filed on Jun. 29, 2006.

International Application No. PCT/US2007/072396 is also a continuation-in-part of the following United States patent applications:
 (c) U.S. patent application Ser. No. 11/599,723, filed on Nov. 14, 2006, now abandoned; and
 (d) U.S. patent application Ser. No. 11/504,117, filed on Aug. 14, 2006, now U.S. Pat. No. 7,617,005.

The present application is also related to each of the following United States patent applications:
 (a) U.S. patent application Ser. No. 11/189,563, filed on Jul. 25, 2005, now U.S. Pat. No. 8,145,316, which is a continuation-in-part of U.S. Patent Application Nos. (a) Ser. No. 11/129,765, filed on May 13, 2005, now U.S. Pat. No. 7,653,438, and which claims the benefit of U.S. Provisional Patent Application No. 60/616,254, filed on Oct. 5, 2004, and 60/624,793, filed on Nov. 2, 2004; (b) Ser. No. 10/900,199 filed on Jul. 28, 2004, now U.S. Pat. No. 6,978,174, and (c) Ser. No. 10/408,665, filed on Apr. 8, 2003, now U.S. Pat. No. 7,162,303.

All of these applications are incorporated herein by reference in their entireties.

INCORPORATION BY REFERENCE

All publications and patent applications mentioned in this specification are herein incorporated by reference to the same extent as if each individual publication or patent application was specifically and individually indicated to be incorporated by reference.

TECHNICAL FIELD

The present invention relates to methods and systems for neuromodulation. More particularly, the present invention relates to methods and systems for achieving renal neuromodulation via thermal heating and/or cooling.

BACKGROUND

Congestive heart failure ("CHF") is a condition typically caused by a structural or functional disorder of the heart and can impair the ability of the heart to fill itself or pump a sufficient amount of blood throughout a body (e.g., kidneys). It has been established in animal models that a heart failure condition can cause abnormally high sympathetic activation of the kidneys, which leads to decreased removal of water from the body, decreased removal of sodium, and increased secretion of renin. Increased renin secretion leads to vasoconstriction of blood vessels supplying the kidneys, which causes decreased renal blood flow. As a result, the reaction of the kidneys to heart failure can perpetuate a downward spiral of the heart failure condition. In addition, the kidneys also play a significant role in the progression of Chronic Renal Failure ("CRF"), End-Stage Renal Disease ("ESRD"), hypertension (pathologically high blood pressure), and other renal or cardio-renal diseases.

Reduction of sympathetic renal nerve activity (e.g., via denervation), can reverse these processes. Ardian, Inc. has developed methods and systems for treating renal disorders by applying an electric field to neural fibers that contribute to renal function. See, for example, Ardian, Inc.'s co-owned and co-pending U.S. patent application (a) Ser. No. 11/129,765, filed on May 13, 2005, (b) Ser. No. 11/189,563, filed on Jul. 25, 2005, and (c) Ser. No. 11/363,867, filed Feb. 27, 2006, all of which are incorporated herein by reference in their entireties. An electric field can initiate renal neuromodulation via denervation caused by irreversible electroporation, electrofusion, apoptosis, necrosis, ablation, thermal alteration, alteration of gene expression or another suitable modality. The electric field can be delivered from an apparatus positioned intravascularly, extravascularly, intra-to-extravascularly, or a combination thereof. Additional methods and apparatus for achieving renal neuromodulation via localized drug delivery (e.g., by a drug pump or infusion catheter), the use of a stimulation electric field, and other modalities are described, for example, in co-owned U.S. Pat. Nos. 7,162,303 and 6,978,174, both of which are incorporated herein by reference in their entireties.

Although these applications provide promising methods and systems, several improvements for enhancing the implementation of these methods and systems would be desirable.

DETAILED DESCRIPTION

A. Overview

Figure 1:
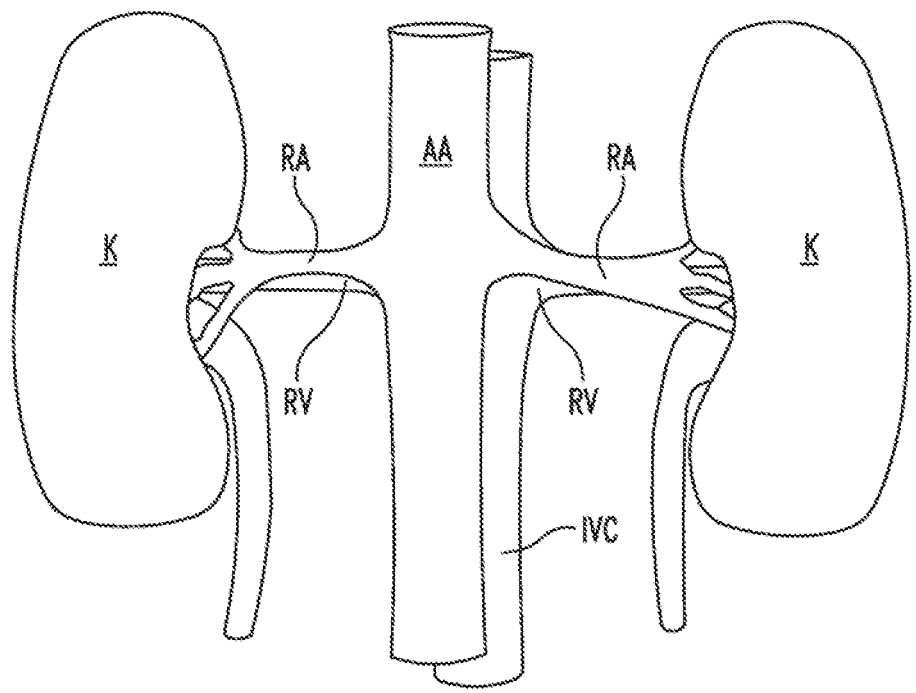
FIG. 1 is a schematic view illustrating human renal anatomy.

The present disclosure provides methods and systems for controlling renal neuromodulation via thermal heating and/or thermal cooling mechanisms. Many embodiments of such methods and systems may reduce renal sympathetic nerve activity. Thermally-induced neuromodulation may be achieved by heating or cooling structures associated with renal neural activity via an apparatus positioned proximate to target neural fibers. For example, such an apparatus can be positioned (a) within renal vasculature (i.e., positioned intravascularly), (b) extravascularly, (c) intra-to-extravascularly, or (d) a combination thereof. Thermally-induced neuromodulation can be achieved by applying thermal stress to neural structures through either heating or cooling for influencing or altering these structures. Additionally or alternatively, the thermal neuromodulation can be due to, at least in part, alteration of vascular structures such as arteries, arterioles, capillaries, or veins that perfuse the target neural fibers or surrounding tissue.

As used herein, thermal heating mechanisms for neuromodulation include both thermal ablation and non-ablative thermal alteration or damage (e.g., via sustained heating or resistive heating). Thermal heating mechanisms may include raising the temperature of target neural fibers above a desired threshold to achieve non-ablative thermal alteration, or above a higher temperature to achieve ablative thermal alteration. For example, the target temperature can be above body temperature (e.g., approximately 37° C.) but less than about 45° C. for non-ablative thermal alteration, or the target temperature can be about 45° C. or higher for the ablative thermal alteration.

As used herein, thermal cooling mechanisms for neuromodulation include non-freezing thermal slowing of nerve conduction and/or non-freezing thermal nerve alteration, as well as freezing thermal nerve alteration. Thermal cooling mechanisms may include reducing the temperature of target neural fibers below a desired threshold, for example, below the body temperature of about 37° C. (e.g., below about 20° C.) to achieve non-freezing thermal alteration. Thermal cooling mechanisms also may include reducing the temperature of the target neural fibers below about 0° C., e.g., to achieve freezing thermal alteration.

In addition to monitoring or controlling the temperature during thermal neuromodulation, the length of exposure to thermal stimuli may be specified to affect an extent or degree of efficacy of the thermal neuromodulation. In many embodiments, the length of exposure to thermal stimuli is longer than instantaneous exposure. For example, the duration of exposure can be as short as about 5 seconds, or could be longer, such as about 30 seconds, or even longer than 2 minutes. In certain specific embodiments, the length of exposure can be less than 10 minutes, but this should in no way be construed as the upper limit of the exposure period. In other embodiments, the exposure can be intermittent or continuous to achieve the desired result. Exposure times measured in hours, days, or longer may be utilized to achieve desired thermal neuromodulation.

When conducting neuromodulation via thermal mechanisms, the temperature thresholds discussed previously may be determined as a function of the duration of exposure to thermal stimuli. Additionally or alternatively, the length of exposure may be determined as a function of the desired temperature threshold. These and other parameters may be specified or calculated to achieve and control desired thermal neuromodulation.

In some embodiments, thermally-induced renal neuromodulation may be achieved by directly and/or indirectly applying thermal cooling or heating energy to the target neural fibers. For example, a chilled or heated fluid can be applied at least proximate to the target neural fiber, or heated or cooled elements (e.g., a thermoelectric element or a resistive heating element) can be placed in the vicinity of the neural fibers. In other embodiments, thermally-induced renal neuromodulation may be achieved via generation and/or application of the thermal energy to the target neural fibers, such as through application of a "thermal" energy field, including, electromagnetic energy, radiofrequency, ultrasound (including high-intensity focused ultrasound), microwave, light energy (including laser, infrared and near-infrared) etc., to the target neural fibers. For example, thermally-induced renal neuromodulation may be achieved via delivery of a pulsed or continuous thermal energy field to the target neural fibers. The energy field can be sufficient magnitude and/or duration to thermally induce the neuromodulation in the target fibers (e.g., to heat or thermally ablate or necrose the fibers). As described herein, additional and/or alternative methods and systems can also be used for thermally-induced renal neuromodulation.

When utilizing thermal heating mechanisms for thermal neuromodulation, protective cooling elements, such as conductive or convective cooling elements, optionally may be utilized to protect smooth muscle cells or other non-target tissue from undesired thermal effects during the thermally-induced renal neuromodulation. Likewise, when utilizing thermal cooling mechanisms, protective heating elements, such as conductive or convective heating elements, may be utilized to protect the non-target tissue. Non-target tissue additionally or alternatively may be protected by focusing the thermal heating or cooling energy on the target neural fibers so that the intensity of the thermal energy outside of the target zone is insufficient to induce undesired thermal effects in the non-target tissue. When thermal neuromodulation is achieved via thermal energy delivered intravascularly, the non-target tissue may be protected by utilizing blood flow as a conductive and/or convective heat sink that carries away excess thermal energy (hot or cold). For example, when blood flow is not blocked, the circulating blood may remove excess thermal energy from the non-target tissue during the procedure. The intravascularly-delivered thermal energy may heat or cool target neural fibers located proximate to the vessel to modulate the target neural fibers while blood flow within the vessel protects non-target tissue of the vessel wall from the thermal energy. For example, the thermal energy can target neural fibers within the adventitia to necrose or ablate the target fibers, and the blood flow can protect tissue in the vessel wall.

One drawback of using a continuous, intravascularly-delivered thermal energy therapy in the presence of blood flow to achieve desired intravascularly-induced neuromodulation is that the feasible thermal magnitude (e.g., power) and/or duration of the therapy may be limited or insufficient. This can be caused by the limited heat capacity of the blood flowing through the blood vessel to remove excess thermal energy from the vessel wall to mitigate damage or necrosis to the non-target tissue. Pulsed RF electric fields or other types of pulsed thermal energy may facilitate greater thermal magnitude (e.g., higher power), longer total duration and/or better controlled intravascular renal neuromodulation therapy compared to a continuous thermal energy therapy. For example, a pulsed thermal therapy may allow for monitoring of effects of the therapy on target or non-target tissue during the interval between the pulses. This monitoring data optionally may be used in a feedback loop to better control therapy, e.g., to determine whether to continue or stop treatment, and it may facilitate controlled delivery of a higher power or longer duration therapy.

Furthermore, the time interval between delivery of thermal energy pulses may facilitate additional convective or other cooling of the non-target tissue of the vessel wall compared to applying an equivalent magnitude or duration of continuous thermal energy. This may occur because blood flow through the blood vessel may convectively cool (heat) the non-target tissue of the vessel wall.

When providing a pulsed thermal therapy, this difference in the heat transfer rate between the tissue of the blood vessel wall and the relatively remote target neural fibers may be utilized to ablate, necrose, or otherwise modulate the target neural fibers without undesirably affecting the non-target tissue. The pulsed thermal energy therapy may be applied with greater thermal magnitude and/or of longer total duration (i.e., the cumulative duration of all thermal energy pulses within the therapy) than a continuous thermal therapy. Heat transfer from the vessel wall to the blood (or vice versa) during the off-time or low-energy interval between the thermal energy pulses facilitates the greater magnitude with moderated damage to the non-target tissue. For example, increasing thermal magnitude (e.g., higher power) may result in an increased rate of heating and, accordingly, a more effective thermal neuromodulation (e.g., ability to affect nerves further away from the lumen wall).

In addition, or as an alternative, to utilizing the patient's blood as a heat sink to establish the difference in heat transfer rate, a thermal fluid (hot or cold) may be injected, infused, or otherwise delivered into the vessel to remove excess thermal energy and protect the non-target tissues. The thermal fluid may, for example, comprise a saline or other biocompatible fluid that is heated, chilled, or at a room temperature. The thermal fluid may, for example, be injected through the device or through a guide catheter at a location upstream from an energy delivery element, or at other locations relative to the tissue for which protection is sought. The thermal fluid may be injected in the presence of blood flow or with the flow temporarily occluded.

Occlusion of flow in combination with thermal fluid delivery may facilitate improved control over the heat transfer kinetics in the non-target tissues. For example, the normal variability in blood flow rate between patients, which would vary the heat transfer capacity of the blood flow, may be controlled for by transferring thermal energy between the vessel wall and a thermal fluid that is delivered at a controlled rate. Use of injected thermal fluids to remove excess thermal energy from non-target tissues to relatively protect the non-target tissues during therapeutic treatment of target tissues may be utilized in body lumens other than blood vessels.

In some embodiments, methods and apparatuses for real-time monitoring of an extent or degree of neuromodulation or denervation (e.g., an extent or degree of thermal alteration) in tissue innervated by the target neural fibers and/or of thermal damage in the non-target tissue may be provided. Likewise, real-time monitoring of the thermal energy delivery element may be provided. Such methods and apparatuses may, for example, comprise a thermocouple or other temperature sensor for measuring the temperature of the monitored tissue or of the thermal energy delivery element. Other parameters that can be measured include the power, total energy delivered, nerve activity or impedance. Monitoring data may be used for feedback control of the thermal therapy. For example, intravascularly-delivered thermal therapy may be monitored and controlled by acquiring temperature or impedance measurements along the wall of the vessel in the vicinity of the treatment zone, and/or by limiting the power or duration of the therapy.

To better understand the structures of several embodiments of devices described below, as well as the methods of using such devices for thermally-induced renal neuromodulation, a description of the renal anatomy in humans is provided.

B. Renal Anatomy Summary

As shown in FIG. 1, the human renal anatomy includes the kidneys K, which are supplied with oxygenated blood by the renal arteries RA. The renal arteries are connected to the heart via the abdominal aorta AA. Deoxygenated blood flows from the kidneys to the heart via the renal veins RV and the inferior vena cava IVC.

Figure 2:
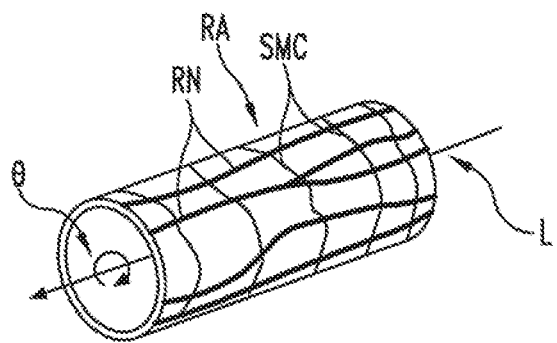
FIG. 2 is a schematic, isometric detail view illustrating the location of the renal nerves relative to the renal artery.

FIG. 2 illustrates a portion of the renal anatomy in greater detail. More specifically, the renal anatomy also includes renal nerves RN extending longitudinally along the lengthwise dimension L of renal artery RA. The renal nerves RN, for example, are generally within the adventitia of the artery. The renal artery RA has smooth muscle cells SMC that surround the arterial circumference and spiral around the angular axis θ of the artery. The smooth muscle cells of the renal artery accordingly have a lengthwise or longer dimension extending transverse (i.e., non-parallel) to the lengthwise dimension of the renal artery. The misalignment of the lengthwise dimensions of the renal nerves and the smooth muscle cells is defined as "cellular misalignment."

Figure 3A:
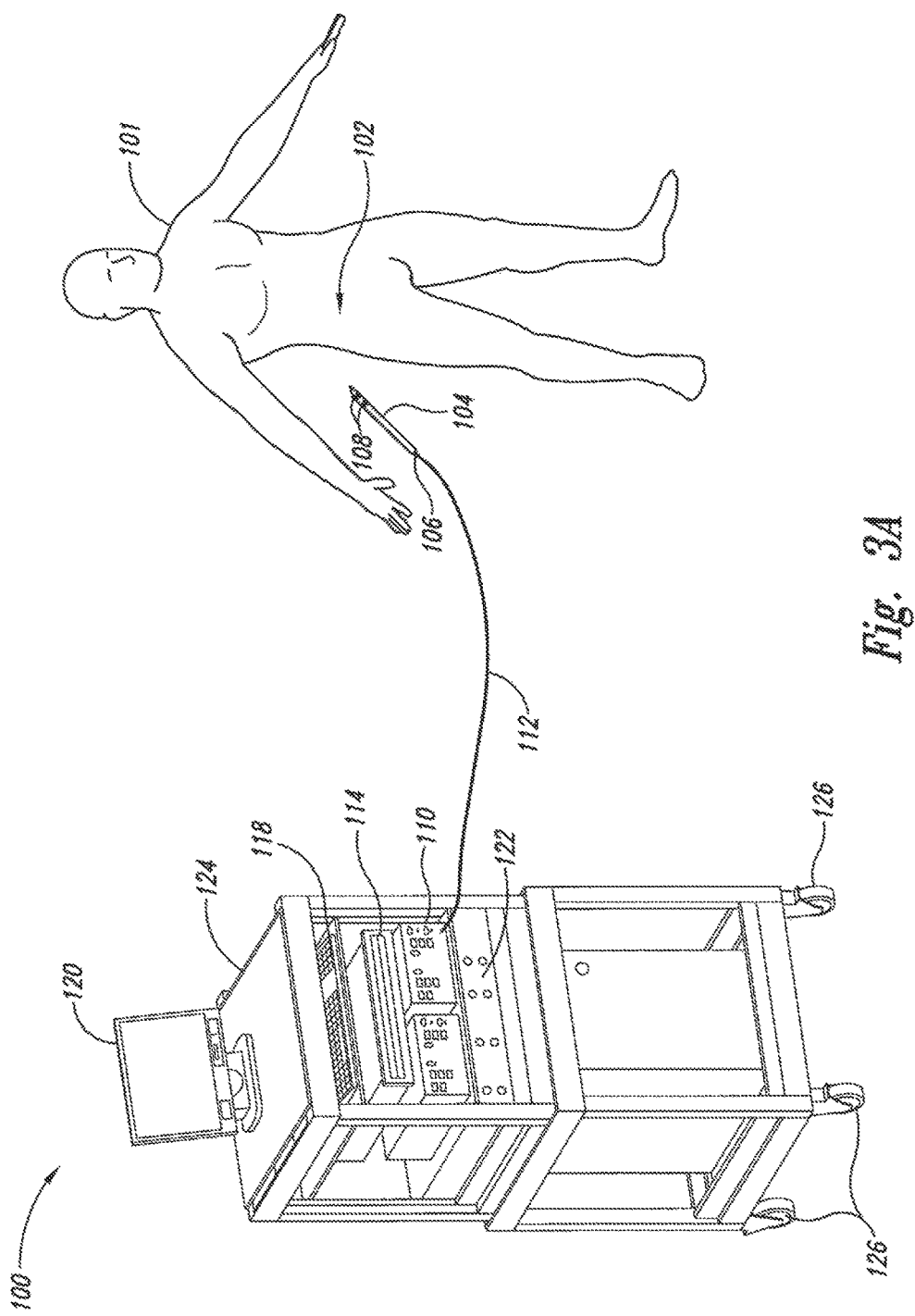
FIG. 3A is an isometric view of a system for controlling thermally-induced renal neuromodulation configured in accordance with one embodiment of the disclosure.

C. Embodiments of Systems and Methods for Thermally-Induced Renal Neuromodulation FIGS. 3A-19 illustrate examples of systems and methods for thermally-induced renal neuromodulation. FIG. 3A, for example, is an isometric view of a system 100 for controlling thermally-induced renal neuromodulation of a patient 101 configured in accordance with an embodiment of the disclosure. The system 100 can include a processor 114, a field generator 110 electrically connected to the processor 114, and a probe 104 operatively coupled to the field generator 110. In the illustrated embodiment, a cable 112 electrically connects the probe 104 to the field generator 110. In other embodiments, the processor 114, the probe 104, and/or the field generator 110 can be connected wirelessly via, for example, radio frequency signals.

The processor 114 can be any general purpose, programmable digital computing device including, for example, a personal computer, a Programmable Logic Controller, a Distributed Control System, or other computing device. The processor 114 can include a central processing unit (CPU), random access memory (RAM), non-volatile secondary storage (e.g., a hard drive, a floppy drive, and a CD-ROM drive), and network interfaces (e.g., a wired or wireless Ethernet card and a digital and/or analog input/output card). Program code and data can be loaded into the RAM from the non-volatile secondary storage and provided to the CPU for execution. The CPU can generate results for display, output, transmit, or storage.

The field generator 110 can generate electrical, radiofrequency, ultrasonic (including high intensity focused ultrasound), microwave, laser or other types of signals with desired parameters sufficient to thermally or otherwise induce renal neuromodulation in target neural fibers. For example, the field generator 110 can generate an electrical signal having a desired frequency, amplitude, and power level, and the cable 112 can transmit the generated signal to the probe 104. The processor 114 is in communication with the field generator 110 to control the power output of the field generator 110 for providing the desired amount of energy to the target neural structures. In the illustrated embodiment, the field generator 110 is located external to the patient 101. In other embodiments, however, the field generator 110 may be positioned internally within the patient.

The probe 104 can be a laparoscopic probe, a percutaneous probe, an intravascular catheter, or another suitable device configured for insertion in proximity to a track of a renal neural supply along and/or in the renal artery, renal vein, hilum, and/or Gerota's fascia under CT, radiographic, or another suitable guidance modality. The probe 104 can include at least one electrode 108 for delivery of a thermal energy field therapy and an electrical connector 106 coupled to the field generator 110 via the cable 112 for delivering a thermal energy field to the electrode 108. In some embodiments, the probe 104 can include an integrated cable (not shown) for delivering a thermal energy field to the electrode 108, and the electrical connector 106 can be omitted. In the illustrated embodiment, the probe 104 is a percutaneous probe configured to be percutaneously advanced into proximity of, for example, an anatomical target 102 (e.g., a renal artery or renal vein) of the patient 101 as described in more detail below with reference to FIG. 3B. In other embodiments, the probe 104 can be an implantable device.

The electrode(s) 108 can be individual electrodes that are electrically independent of each other, a segmented electrode with commonly connected contacts, or a continuous electrode. A segmented electrode can, for example, be formed by providing a slotted tube fitted onto the electrode, or by electrically connecting a series of individual electrodes. Individual electrodes or groups of electrodes 108 can be configured to provide a bipolar signal. The electrodes 108 can be dynamically assignable to facilitate monopolar and/or bipolar energy delivery between any of the electrodes and/or between any of the electrodes and a remote electrode. The remote electrode may, for example, be attached externally to the patient's skin (e.g., to the patient's leg or flank).

The probe 104 can also include at least one sensor (not shown) for measuring a physiological parameter of the patient 101. For example, the probe 104 can include a temperature sensor, an impedance sensor, an ultrasound sensor, and/or other types of sensors. The sensor can measure the physiological parameter (e.g., a temperature) and transmit the measured physiological parameter to the processor 114 for processing.

Optionally, the system 100 can also include an input device 118, an output device 120, and/or a control panel 122 operatively coupled to the processor 114. The input device 118 can include a keyboard, a mouse, a touch screen, a push button, a switch, a potentiometer, and any other devices suitable for accepting user input. The output device 120 can include a display screen, a printer, a medium reader, an audio device, and any other devices suitable for providing user feedback. The control panel 122 can include indicator lights, numerical displays, and audio devices. In the embodiment shown in FIG. 3A, a rack 124 with wheels 126 carries the processor 114, the field generator 110, the input device 118, and the output device 120 for portability. In another embodiment, the various components can be incorporated into a single enclosure (e.g., the field generator 110) for portably mounting on, for example, an IV stand, an IV pole, an instrument stand, an infusion stand, and/or other supporting structures. In further embodiments, the various components can be fixedly installed.

Figure 4A:
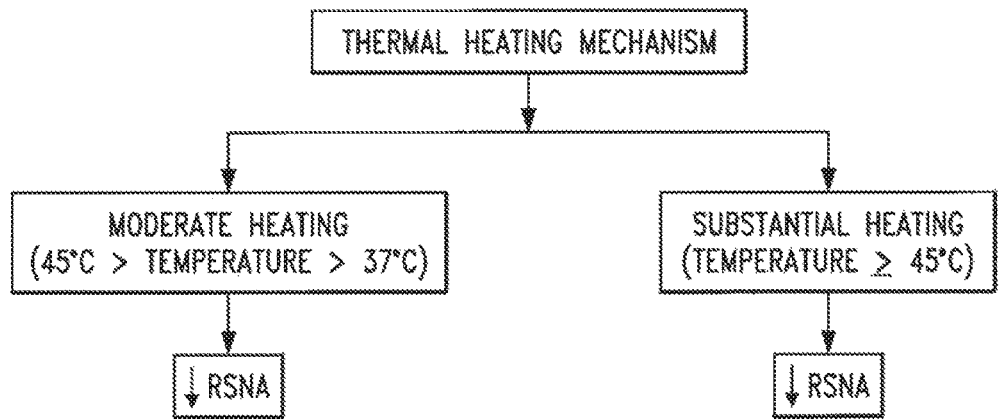
FIGS. 4A and 4B are schematic diagrams illustrating several types of thermally-induced renal neuromodulation that may be achieved with the systems and methods described herein.
Figure 4B:
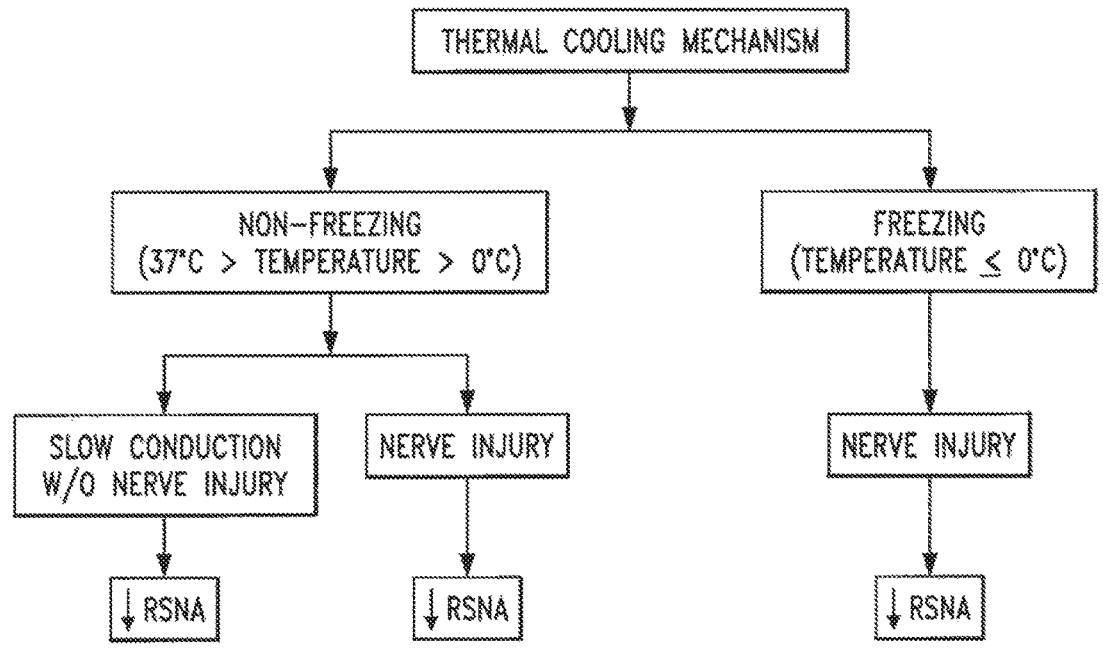

In operation, an operator can place the probe 104 at least proximate to a wall of a body lumen of the patient 101, for example, the renal artery or renal vein, and then deliver energy to the probe 104 to achieve thermal renal neuromodulation as described in more detail below. FIGS. 4A and 4B, for example, illustrate the various types of thermal neuromodulation that may be achieved with the systems and methods described herein. FIGS. 4A and 4B are provided only for the sake of illustration and should in no way be construed as limiting.

FIG. 4A illustrates thermal neuromodulation due to heat exposure. As shown, exposure to heat in excess of a body temperature of about 37° C., but below a temperature of about 45° C., may induce thermal alteration via moderate heating of the target neural fibers or of vascular structures that perfuse the target fibers. In cases where vascular structures are affected, the target neural fibers are denied perfusion resulting in necrosis of the neural tissue. For example, this may induce non-ablative thermal alteration in the fibers or structures. Exposure to heat above a temperature of about 45° C., or above about 60° C., may induce thermal alteration via substantial heating of the fibers or structures. For example, such higher temperatures may thermally ablate the target neural fibers or the vascular structures. In some patients, it may be desirable to achieve temperatures that thermally ablate the target neural fibers or the vascular structures, but that are less than about 90° C., or less than about 85° C., or less than about 80° C., and/or less than about 75° C. Regardless of the type of heat exposure utilized to induce the thermal neuromodulation, a reduction in renal sympathetic nerve activity ("RSNA") is expected.

Referring to FIG. 4B, thermal cooling for neuromodulation includes non-freezing thermal slowing of nerve conduction and/or nerve alteration, as well as freezing thermal nerve alteration. Non-freezing thermal cooling may include reducing the temperature of the target neural fibers or of the vascular structures that feed the fibers to temperatures below the body temperature of about 37° C., or below about 20° C., but above the freezing temperature of about 0° C. This non-freezing thermal cooling may either slow nerve conduction or may cause neural alteration. Slowed nerve conduction may use continuous or intermittent cooling of the target neural fibers to sustain the desired thermal neuromodulation, while neural alteration may require only a discrete treatment to achieve sustained thermal neuromodulation. Thermal cooling for neuromodulation also may include freezing thermal nerve alteration by reducing the temperature of the target neural fibers or of the vascular structures that feed the fibers to temperatures below the freezing point of about 0° C. Regardless of the type of cold exposure utilized to induce the thermal neuromodulation (freezing or non-freezing), a reduction in RSNA is expected.

Referring back to FIG. 3A, the operator and/or the processor 114 can monitor and control the energy delivery process. As described above, the probe 104 can include sensors that measure physiological parameters of the patient 101. The probe 104 can transmit the measured parameters to the processor 114 via the cable 112 or wirelessly. The processor 114 can process and analyze the received parameters and display the parameters in appropriate units on the output device 120. The processor 114 can cause the system to sound an alarm if the received parameters exceed preset thresholds and signal any alarms using either the output device 120 and/or the control panel 122. The processor 114 can also analyze and process parameter measurement data, for either a single parameter or multiple parameters in combination, and can compare the data against stored, non-empirical data to identify any patterns that may warrant closer attention. The processor 114 can also store the received parameters and data patterns in a database for later retrieval. In addition, the processor 114 can modulate the power output of the field generator 110 based on the received parameters and/or input received from the operator via the input device 118 as described in more detail below with reference to FIGS. 16-19.

Figure 3B:
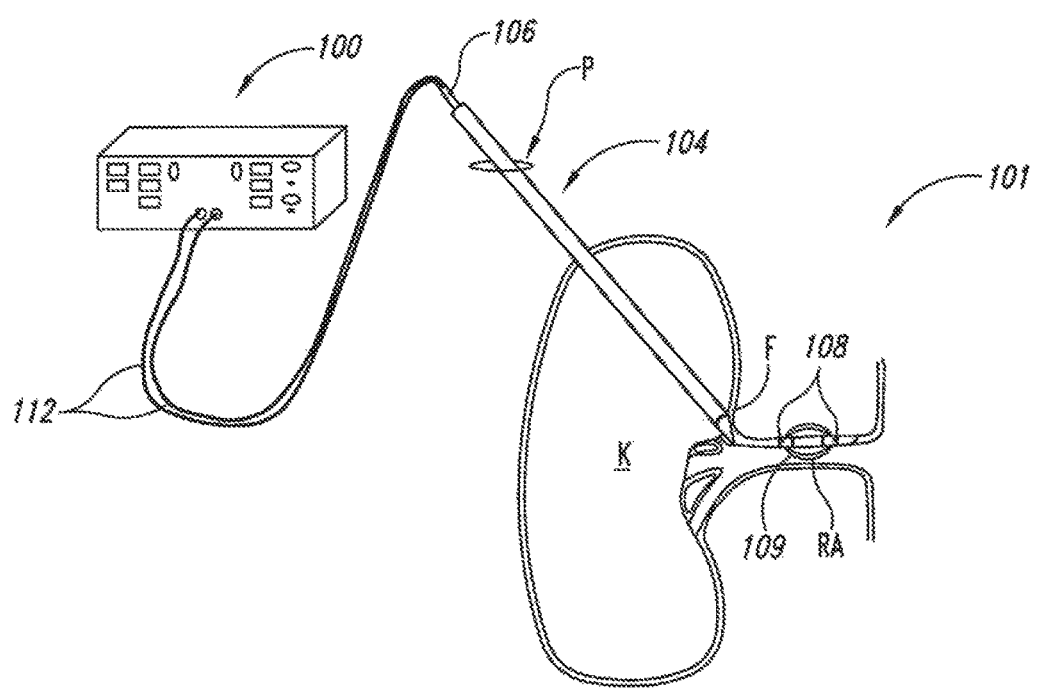
FIG. 3B is a schematic side view, partially in section, illustrating an embodiment of an extravascular system for thermally-induced renal neuromodulation.

In FIG. 3B, the probe 104 has been advanced through a percutaneous access site P into proximity with the renal artery RA. The probe 104 pierces the Gerota's fascia F of the patient 101, and the electrodes 108 are advanced into position through the probe 104 and along the annular space between the artery and fascia. Once properly positioned, the target neural fibers can be heated via a pulsed or continuous electric field delivered across the electrode(s) 108. In FIG. 3B, for example, the electrode(s) 108 comprise a bipolar electrode pair that can generate thermal energy field 109. Such heating can ablate or cause non-ablative thermal alteration to the target neural fibers to at least partially denervate the kidney innervated by the target neural fibers. The energy field also can induce reversible or irreversible electroporation in the target neural fibers which can compliment the thermal alteration induced in the neural fibers.

After treatment, the probe 104 can be removed from the patient to conclude the procedure.

FIGS. 5A-9, 14, and 15 illustrate several embodiments of intravascular systems and associated methods for thermally-induced renal neuromodulation. It will be appreciated that the electrode(s) in each of the following embodiments can be connected to a generator (e.g., the field generator 110) even through the generator is not explicitly shown or described below.

Figure 5A:
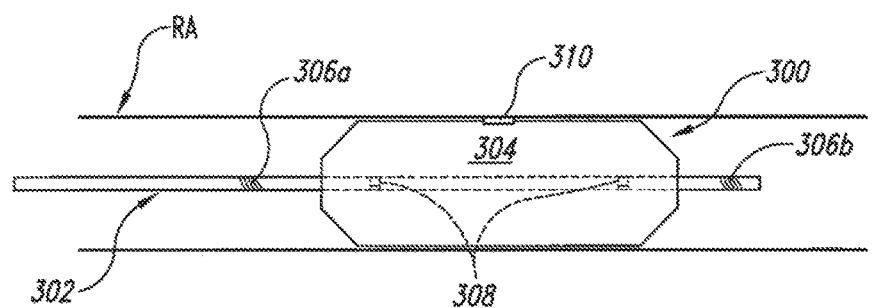
FIGS. 5A-5C are schematic side views, partially in section, illustrating an intravascular apparatus for thermally-induced renal neuromodulation configured in accordance with an embodiment of the disclosure.
Figure 5B:
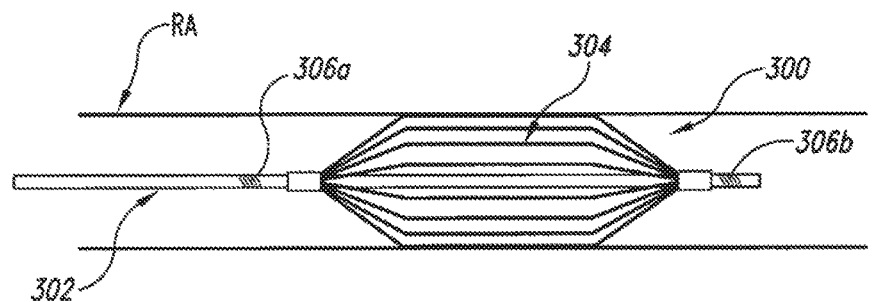

FIGS. 5A and 5B, for example, are schematic side views illustrating an intravascular apparatus 300 for thermally-induced renal neuromodulation. The apparatus 300 can include a catheter 302 having an optional positioning element 304, shaft electrodes 306a and 306b disposed along the shaft of the catheter 302, and optional radiopaque markers 308 disposed along the shaft of the catheter 302 in the region of the positioning element 304. The positioning element 304 can be a balloon, an expandable wire basket, other mechanical expanders, or another suitable device for holding the electrodes 306a-b relative to the vessel and/or the nerves. The electrodes 306a-b can be arranged such that the electrode 306a is near a proximal end of the positioning element 304 and the electrode 306b is near the distal end of the positioning element 304. The electrodes 306a-b are electrically coupled to the field generator 110 (FIG. 3A) for delivering energy to the target neural fibers. In other embodiments, one or more of the electrodes 306a-b can comprise Peltier electrodes for heating or cooling the target neural fibers to modulate the fibers.

The positioning element 304 optionally can position or otherwise drive the electrodes 306a-b into contact with the lumen wall. For example, when the positioning element 304 is an inflatable balloon as shown in FIG. 5A, the balloon can serve as both a centering and/or expansion element for the expandable electrode element(s) 306a-b, and as an impedance-altering electrical insulator for directing an energy field delivered via the electrodes 306a-b into or across the vessel wall for modulation of target neural fibers. The electrical insulation provided by the positioning element 304 can reduce the magnitude of applied energy or other parameters of the energy field necessary to achieve the desired modulation of the target fibers, which can include partial or full denervation of tissue containing the target fibers. Applicants have previously described use of a suitable impedance-altering element in co-pending U.S. patent application Ser. No. 11/266,993, filed Nov. 4, 2005, which is incorporated herein by reference in its entirety.

Furthermore, the positioning element 304 optionally may be utilized as a cooling element and/or a heating element. For example, the positioning element 304 may be inflated with a chilled fluid that serves as a heat sink for removing heat from tissue that contacts the element. Conversely, the positioning element 304 optionally may be a heating element by inflating it with a warmed fluid that heats tissue in contact with the element. The thermal fluid optionally may be circulated and/or exchanged within the positioning element 304 to facilitate more efficient conductive and/or convective heat transfer. Thermal fluids also may be used to achieve thermal neuromodulation via thermal cooling or heating mechanisms, as described in greater detail herein below.

The positioning element 304 (or any other portion of the apparatus 300) additionally or alternatively may comprise one or more sensors for monitoring the process. In one embodiment, the positioning element 304 has a wall-contact thermocouple 310 (FIG. 5A) for monitoring the temperature or other parameters of the target tissue, the non-target tissue, the electrodes, the positioning element and/or any other portion of the apparatus 300. Alternatively, electrodes 306a and/or 306b can have one or more thermocouples built into them.

Figure 5C:
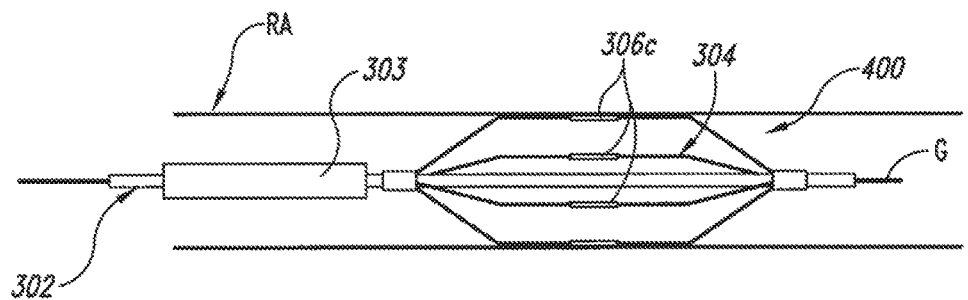

The electrodes 306a-b of the intravascular embodiment shown in FIGS. 5A and 5B can be individual electrodes (i.e., independent contacts), a segmented electrode with commonly connected contacts, or a single continuous electrode. Furthermore, the electrodes 306a-b can also be configured to provide a bipolar signal, or the electrodes 306a-b can be used together or individually in conjunction with a separate patient ground pad for monopolar use. The electrodes 306a-b can be attached to the positioning element 304 such that they contact the wall of the artery upon expansion of the positioning elements 304. The electrodes 306a-b can, for example, be affixed to the inside surface, outside surface, or at least partially embedded within the wall of the positioning element 304. FIG. 5C, described hereinafter, illustrates one example of wall-contact electrodes, while FIGS. 6-9 illustrate alternative wall-contact electrodes.

As shown in FIG. 5A, the catheter 302 can be delivered to a treatment site within the renal artery RA as shown, or it may be delivered to a renal vein or to any other vessel in proximity to neural tissue contributing to renal function, in a low profile delivery configuration through a guide catheter or other device. Alternatively, catheters may be positioned in multiple vessels for thermal renal neuromodulation, e.g., within both the renal artery and the renal vein. Techniques for pulsed electric field renal neuromodulation in multiple vessels have been described previously, for example, in co-pending U.S. patent application Ser. No. 11/451,728, filed Jul. 12, 2006, which is incorporated herein by reference in its entirety.

Once the positioning element 304 is at a desired location within the renal vasculature, it can be expanded into contact with an interior wall of the vessel. A thermal energy field then may be delivered via the electrodes 306a-b across the wall of the artery. The field thermally modulates the activity along neural fibers that contribute to renal function via heating. In several embodiments, the thermal modulation at least partially denervates the kidney innervated by the neural fibers via heating. This may be achieved, for example, via thermal ablation or non-ablative alteration of the target neural fibers.

In the embodiment shown in FIG. 5A, the positioning element 304 is an inflatable balloon that can preferentially direct the energy field as discussed above. In the embodiment illustrated in FIG. 5B, the positioning element 304 comprises an expandable wire basket that substantially centers the electrodes 306a-b within the vessel without blocking blood flow through the vessel. During delivery of the thermal energy field (or of other thermal energy), the blood can act as a heat sink for conductive and/or convective heat transfer to remove excess thermal energy from the non-target tissue. This protects the non-target tissue from undesired thermal effects. This effect may be enhanced when blood flow is not blocked during energy delivery, such as in the embodiment shown in FIG. 5B.

Using the patient's blood as a heat sink is expected to facilitate delivery of longer or greater magnitude thermal treatments with reduced risk of undesired effects to the non-target tissue, which may enhance the efficacy of the treatment at the target neural fibers. Although the embodiment shown in FIG. 5B includes a positioning element 304 for centering the electrodes 306a-b without blocking flow, it should be understood that the positioning element 304 may be eliminated and/or that the electrodes 306a-b may be attached to the positioning element 304 such that they are not centered in the vessel upon expansion of the centering element. In such embodiments, the patient's blood may still mitigate excess thermal heating or cooling to protect non-target tissues.

One drawback of using a continuous, intravascularly-delivered thermal energy therapy in the presence of blood flow to achieve desired intravascularly-induced neuromodulation is that the feasible thermal magnitude (e.g., power) and/or duration of the therapy may be limited or insufficient. This can occur because the capacity of the blood to remove heat is limited, and thus the blood flowing through the blood vessel may not remove enough excess thermal energy from the vessel wall to mitigate or avoid undesirable effect in the non-target tissue. Use of a pulsed thermal energy therapy, such as a pulsed thermal RF electric field, may facilitate greater thermal magnitude (e.g., higher power), longer total duration, and/or better controlled intravascular renal neuromodulation therapy compared to a continuous thermal energy therapy. For example, the effects of the therapy on target or non-target tissue may be monitored during the intervals between the pulses. This monitoring data optionally may be used in a feedback loop to better control the therapy, e.g., to determine whether to continue or stop treatment, and it may facilitate controlled delivery of a higher power or longer duration therapy.

Furthermore, the off-time or low-energy intervals between thermal energy pulses may facilitate additional convective or other cooling of the non-target tissue of the vessel wall compared to use of a continuous thermal therapy of equivalent magnitude or duration. This can occur because blood flow through the blood vessel can convectively cool (heat) the non-target tissue of the vessel wall faster than the target neural fibers positioned outside of the vessel wall.

When providing a pulsed thermal therapy, the difference in heat transfer rates between tissue of the blood vessel wall and the relatively remote target neural fibers may be utilized to ablate, necrose, or otherwise modulate the target neural fibers without producing undesirable effects in the non-target tissue. As a result, the pulsed thermal energy therapy may be applied with greater thermal magnitude and/or of longer total duration (i.e., the cumulative duration of all thermal energy pulses) compared to a continuous thermal therapy. The higher heat transfer rate at the vessel wall during the intervals between the thermal energy pulses facilitates the greater magnitude/longer duration delivery.

In addition or as an alternative to utilizing the patient's blood as a heat sink to create a difference in the heat transfer rate, a thermal fluid (hot or cold) may be injected, infused or otherwise delivered into the vessel to remove excess thermal energy and protect the non-target tissues. The thermal fluid may, for example, comprise saline or another biocompatible fluid that is heated, chilled or at room temperature. The thermal fluid may, for example, be injected through the device or through a guide catheter at a location upstream from an energy delivery element, or at other locations relative to the tissue for which protection is sought. The thermal fluid may be injected in the presence of blood flow or with the blood flow temporarily occluded.

In several embodiments, the occlusion of the blood flow in combination with thermal fluid delivery may facilitate good control over the heat transfer kinetics. For example, the normal variability in blood flow rate between patients, which would vary the heat transfer capacity of the blood flow, may be controlled for by transferring thermal energy between the vessel wall and a thermal fluid that is delivered at a controlled rate. Furthermore, this method of using an injected thermal fluid to remove excess thermal energy from non-target tissues in order to protect the non-target tissues during therapeutic treatment of target tissues may be utilized in body lumens other than blood vessels.

One or more sensors, such as the thermocouple 310 of FIG. 5A, can be used to monitor the temperature(s) or other parameter(s) at the electrodes 306a-b, the wall of the vessel and/or at other desired locations along the apparatus or the patient's anatomy. The thermal neuromodulation may be controlled using the measured parameter(s) as feedback. This feedback may be used, for example, to maintain the parameter(s) below a desired threshold. For example, the parameter(s) may be maintained below a threshold that may cause undesired effects in the non-target tissues. With blood flowing through the vessel, more thermal energy may be carried away, which may allow for higher energy treatments than when blood flow is blocked in the vessel.

As discussed previously, when utilizing intravascular apparatus to achieve thermal neuromodulation, in addition or as an alternative to central positioning of the electrode(s) within a blood vessel, the electrode(s) optionally may be configured to contact an internal wall of the blood vessel. Wall-contact electrode(s) may facilitate more efficient transfer of a thermal energy field across the vessel wall to target neural fibers, as compared to centrally-positioned electrode(s). In some embodiments, the wall-contact electrode(s) may be delivered to the vessel treatment site in a reduced profile configuration, then expanded in vivo to a deployed configuration wherein the electrode(s) contact the vessel wall. In some embodiments, expansion of the electrode(s) is at least partially reversible to facilitate retrieval of the electrode(s) from the patient's vessel.

FIG. 5C, for example, is a schematic side view illustrating an embodiment of an apparatus 400 having one or more wall-contact electrodes 306c. One or more struts of the expandable basket positioning element 304 can include a conductive material that is insulated in regions other than along segments that contact the vessel wall and form electrode(s) 306c. The electrode(s) 306c can be used in either a bipolar or a monopolar configuration. Furthermore, the electrode(s) 306c can include one or more sensors (not shown) for monitoring and/or controlling the effects of the thermal energy delivery. The sensors, for example, can be thermocouples, impedance sensors, temperature sensors, etc.

Figure 6A:
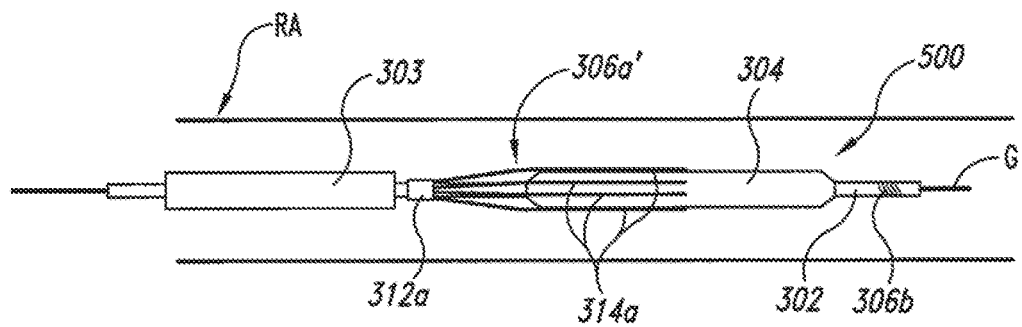
FIGS. 6A and 6B are schematic side views, partially in section, illustrating another embodiment of an intravascular apparatus having one or more wall-contact electrodes.
Figure 6B:
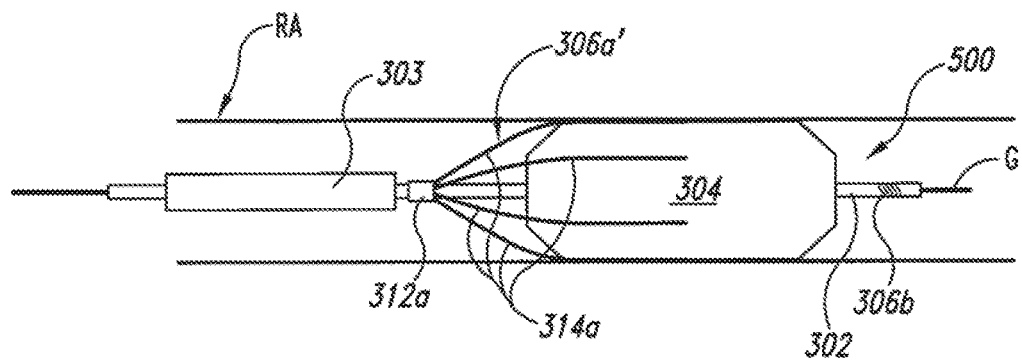

FIGS. 6A and 6B are schematic side views illustrating another embodiment of an intravascular apparatus 500 having electrodes configured to contact the interior wall of a vessel. The apparatus 500 of FIGS. 6A and 6B differs from the apparatus 300 of FIGS. 5A and 5B in that the proximal electrode 306a of FIGS. 5A and 5B has been replaced with a wall-contact electrode 306a'. The wall-contact electrode 306a' includes a proximal connector 312a that connects the electrode 306a' to the shaft of the catheter 302 and is electrically coupled to the field generator (not shown). The apparatus 500 also has a plurality of extensions 314a that extend from the proximal connector 312a and at least partially extend over a surface of the positioning element 304. The extensions 314a optionally may be selectively insulated such that only a selective portion of the extensions 314a (e.g., the distal tips of the extensions) are electrically active. The electrode 306a' and or the connector 312a optionally may be fabricated from a slotted tube, such as a stainless steel or shape-memory (e.g., NiTi) slotted tube. Furthermore, all or a portion of the electrode may be gold-plated to improve radiopacity and/or conductivity.

As shown in FIG. 6A, the catheter 302 may be delivered over a guidewire G to a treatment site within the patient's vessel with the electrode 306a' positioned in a reduced profile configuration. The catheter 302 optionally may be delivered through a guide catheter 303 to facilitate such reduced profile delivery of the wall-contact electrode 306a'. When positioned as desired at a treatment site, the electrode 306a' may be expanded into contact with the vessel wall by expanding the positioning element 304 (as shown in FIG. 6B). A thermal bipolar electric field then may be delivered across the vessel wall and between the electrodes 306a' and 306b to induce thermal neuromodulation, as discussed previously. Alternatively 306a' or 306b could comprise a monopolar electrode, wherein the return electrode (not shown) is placed on an external surface of the patient. The optional positioning element 304 may alter impedance within the blood vessel and more efficiently route the electrical energy across the vessel wall to the target neural fibers.

After terminating the electric field, the electrode 306a' may be returned to a reduced profile and the apparatus 500 may be removed from the patient or repositioned in the vessel. For example, the positioning element 304 may be collapsed (e.g., deflated), and the electrode 306a' may be contracted by withdrawing the catheter 302 within the guide catheter 303. Alternatively, the electrode 306a' may be fabricated from a shape-memory material biased to the collapsed configuration, such that the electrode self-collapses upon collapse of the positioning element 304.

Although the electrode 306a' shown in FIGS. 6A and 6B is expanded into contact with the vessel wall, it should be understood that the electrode 306a' alternatively may be fabricated from a self-expanding material biased such that the electrode 306a' self-expands into contact with the vessel wall upon positioning of the electrode 306a' distal of the guide catheter 303. A self-expanding embodiment of the electrode 306a' may obviate a need for the positioning element 304 and/or may facilitate maintenance of blood flow through the blood vessel during delivery of an electric field via the electrode. After delivery of the electric field, the self-expanding electrode 306a' may be returned to a reduced profile to facilitate removal of the apparatus 300 from the patient by withdrawing the catheter 302 within the guide catheter 303.

Figure 7A:
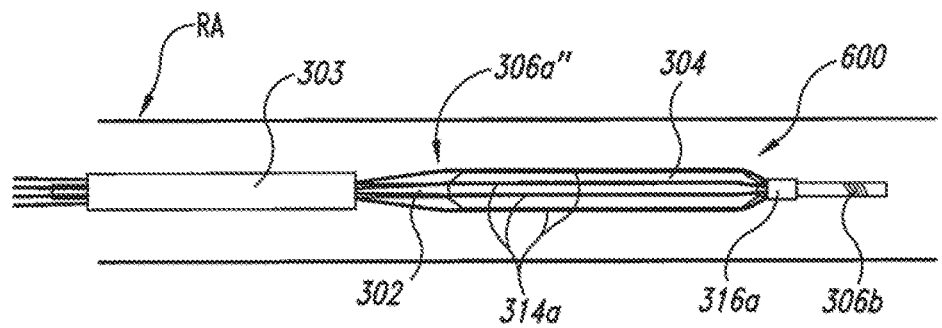
FIGS. 7A and 7B are schematic side views, partially in section, illustrating still another embodiment of an intravascular apparatus having wall-contact electrodes.
Figure 7B:
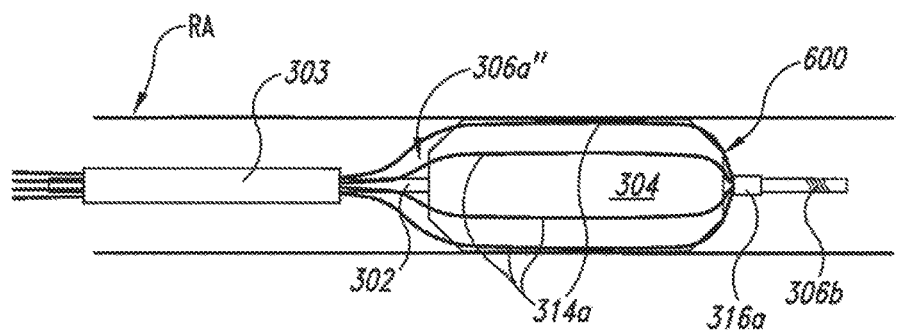

FIGS. 7A and 7B are schematic side views illustrating still another embodiment of an apparatus 600 for delivering a field using a wall-contact electrode 306a". FIG. 7A shows the electrode 306a" in a reduced profile configuration, and FIG. 7B shows the electrode 306a" in an expanded configuration in which the conductive portions of the electrode 306a" contact the vessel wall. As an alternative to the proximal connector 312a of the electrode 306a' of FIGS. 6A and 6B, the electrode 306a" of FIGS. 7A and 7B includes a distal connector 316a for coupling the electrode 306a" to the shaft of the catheter 302 on the distal side of the positioning element 304. The distal connector 316a enables the electrode 306a" to extend over the entirety of the positioning element 304 and can facilitate contraction of the electrode 306a" after thermal neuromodulation. For example, the electrode 306a" can be contracted by proximally retracting the guide catheter 303 relative to the catheter 302 during or after contraction of the positioning element 304. Alternatively, the wires at the proximal end of the apparatus can be proximally retracted to contract the electrode 306a".

Figure 8A:
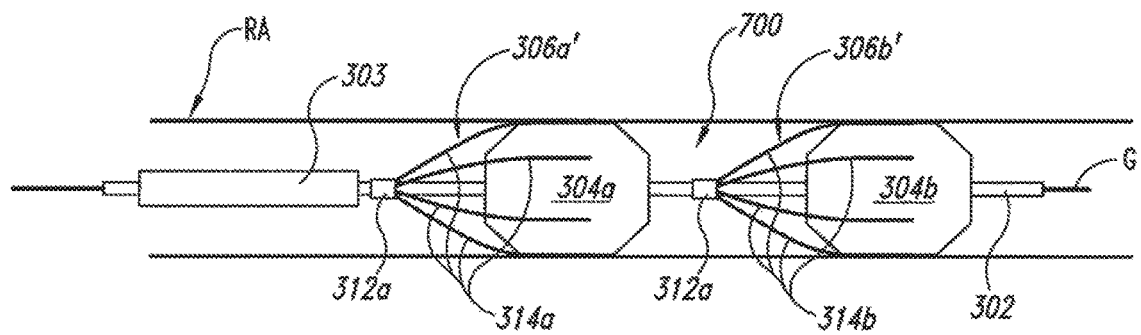
FIGS. 8A and 8B are schematic side views, partially in section, illustrating yet another embodiment of an intravascular apparatus having multiple wall-contact electrodes.
Figure 8B:
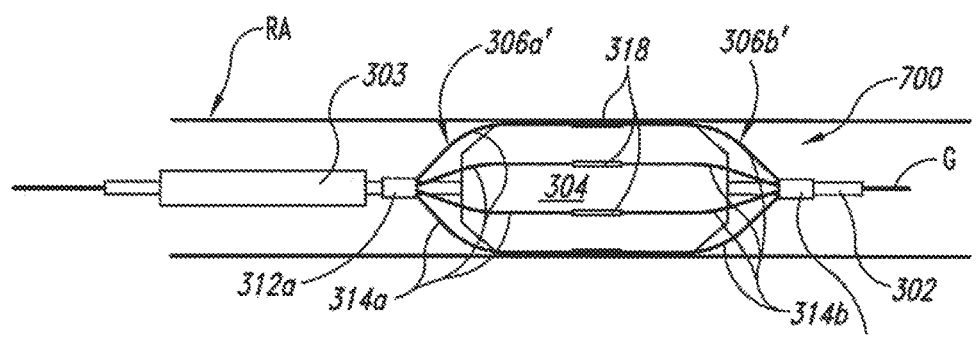

FIGS. 8A and 8B are schematic side views illustrating yet another embodiment of an apparatus 700 for thermally-induced neuromodulation. The apparatus 700 of FIGS. 8A and 8B includes the proximal electrode 306a' of FIGS. 6A and 6B, and a distal wall-contact electrode 306b'. The apparatus 700 also includes proximal and distal positioning elements 304a and 304b, respectively, for expanding the proximal and distal wall-contact electrodes 306a' and 306b', respectively, into contact with the vessel wall. The embodiment shown in FIG. 8B includes only a single positioning element 304, but the distal wall-contact electrode 306b' is proximal facing and positioned over the distal portion of the positioning element 304 to facilitate expansion of the distal electrode 306b'. In the embodiment illustrated in FIG. 8B, the extensions of the proximal 306a' and distal electrodes 306b' optionally may be connected along non-conductive connectors 318 to facilitate collapse and retrieval of the electrodes post-treatment.

A bipolar electric field may be delivered between the proximal and distal wall-contact electrodes 306a' and 306b', or a monopolar electric field may be delivered between the proximal electrode 306a' and/or distal electrode 306b' and an external ground. Having both the proximal and distal electrodes 306a' and 306b' in contact with the wall of the vessel may facilitate more efficient energy transfer across the wall during delivery of a thermal energy field, as compared to having one or both of the proximal and distal electrodes 306a' and 306b' centered within the vessel.

Figure 9A:
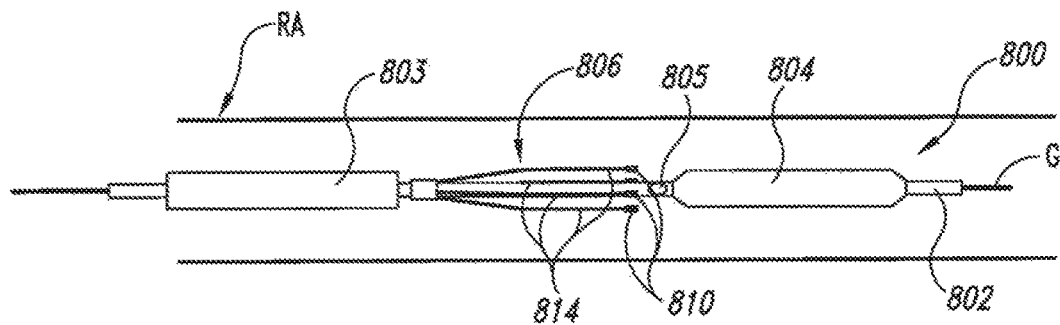
FIGS. 9A-9F are schematic side views, partially in section, illustrating still further embodiments of intravascular systems including one or more wall-contact electrodes, as well as optional blood flow occlusion features and/or thermal fluid injection functions.
Figure 9B:
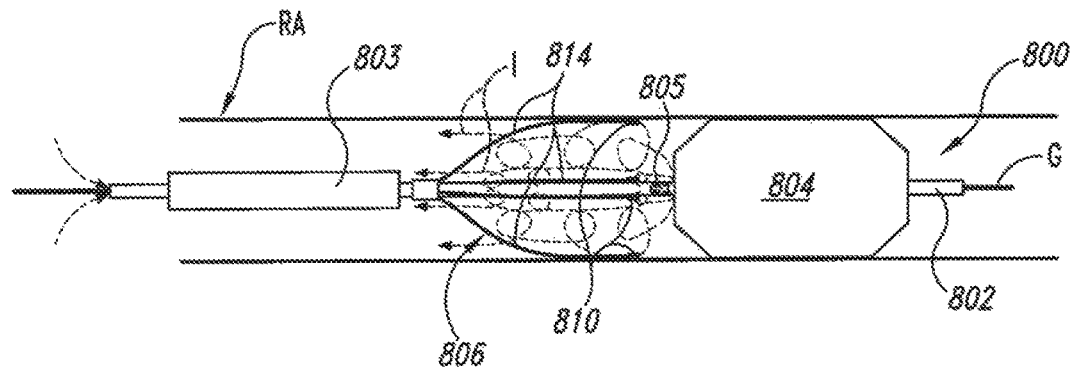
Figure 9C:
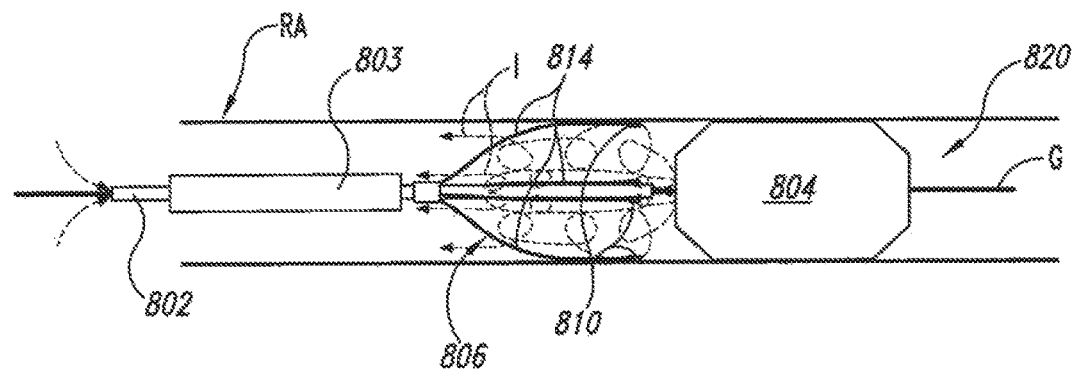
Figure 9D:
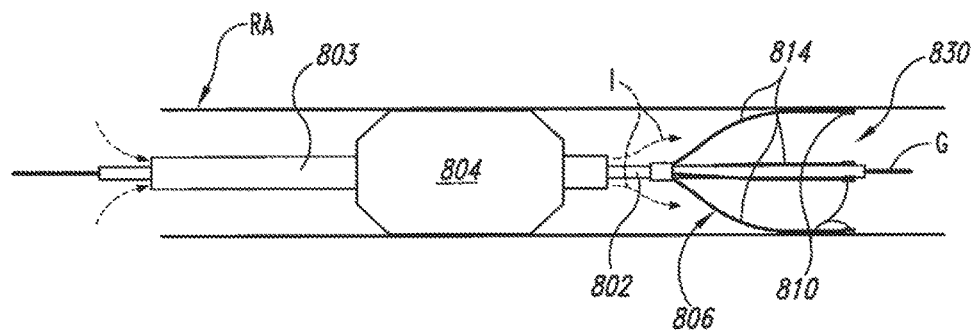
Figure 9E:
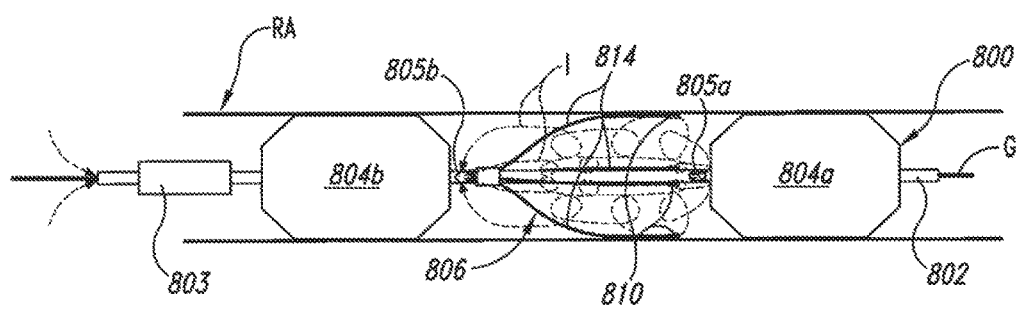
Figure 9F:
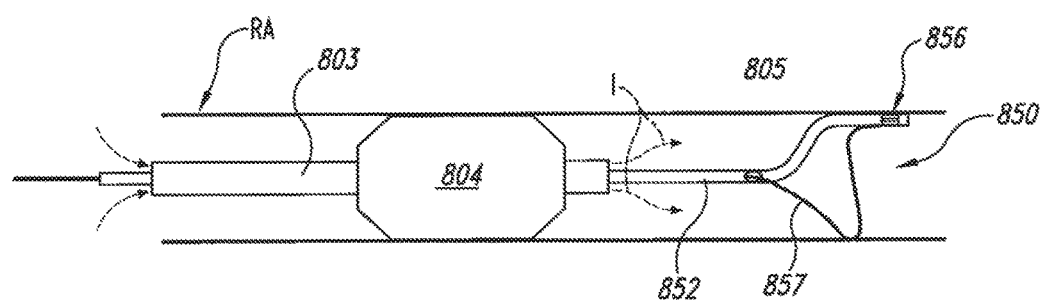
Figure 9G:
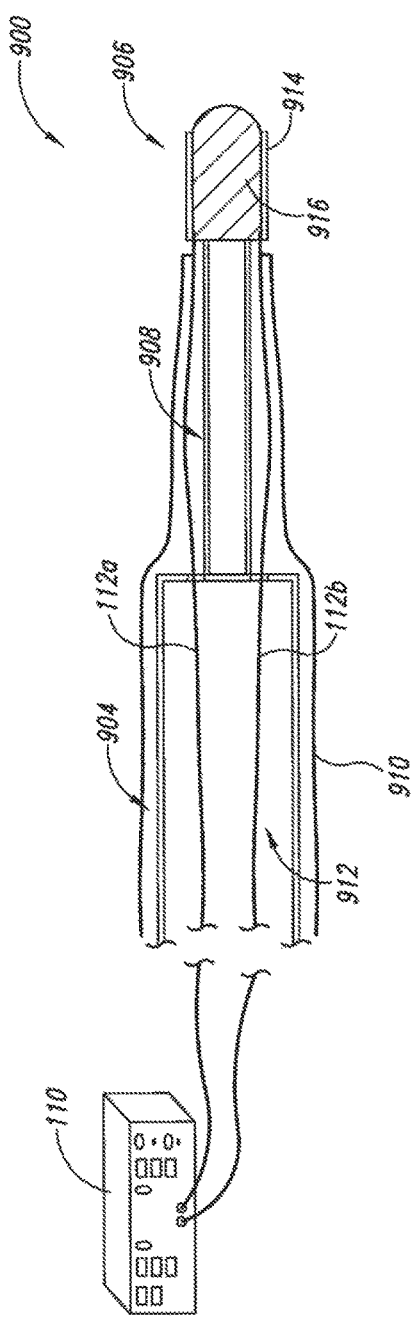
FIGS. 9G-9N are schematic side views, partially in section, illustrating embodiments of probes for thermally-induced renal neuromodulation.
Figure 9H:
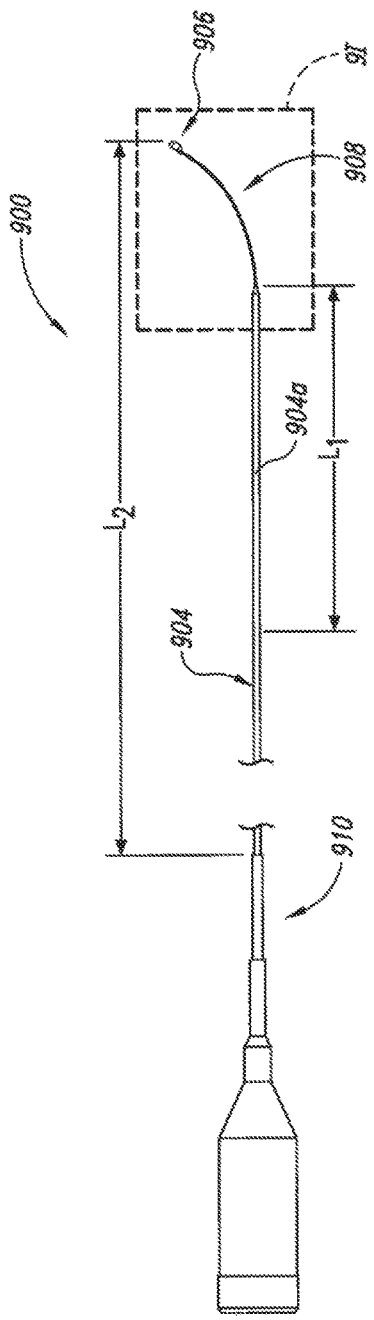
Figure 9I:
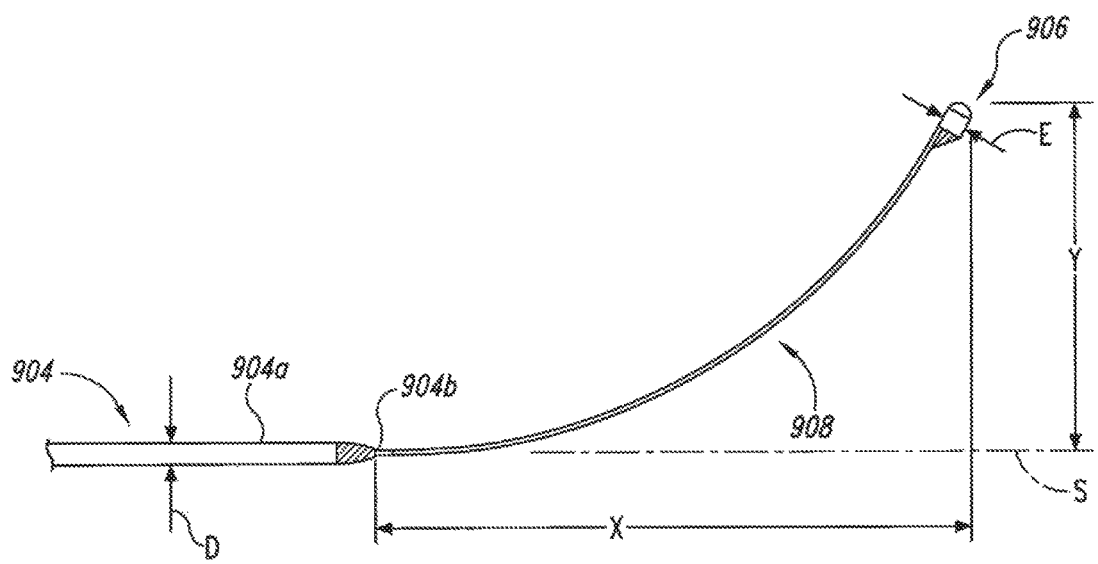
Figure 9J:
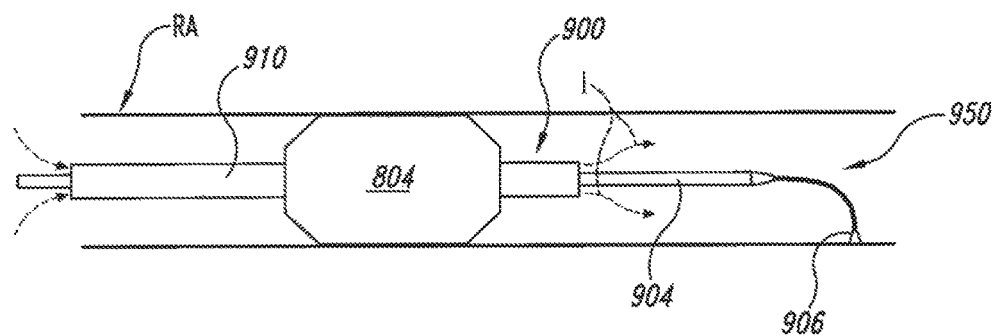
Figure 9K:
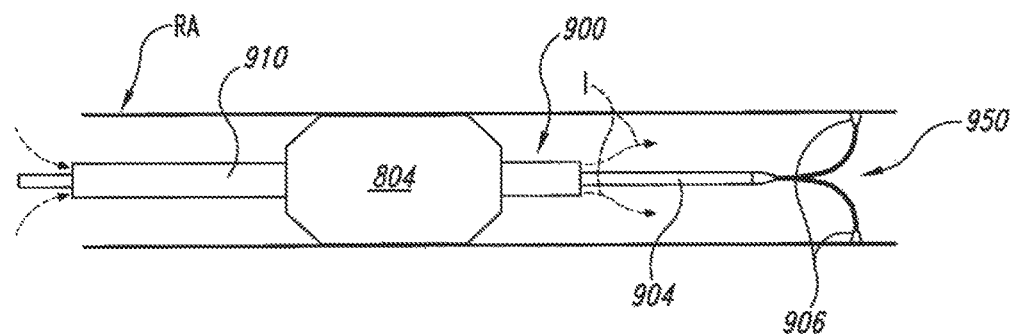
Figure 9L:
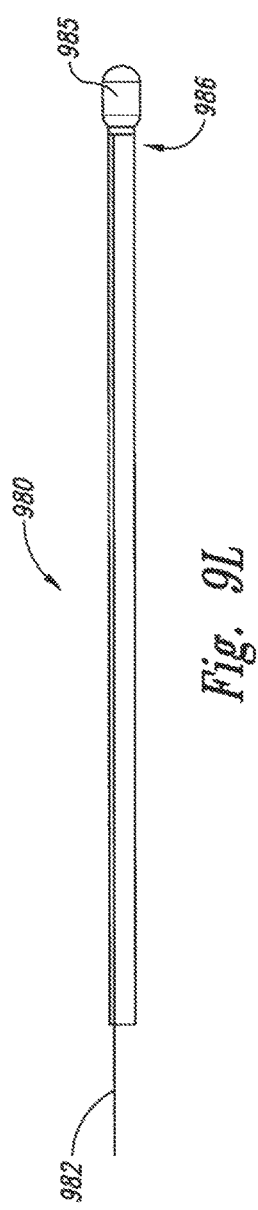
Figure 9M:
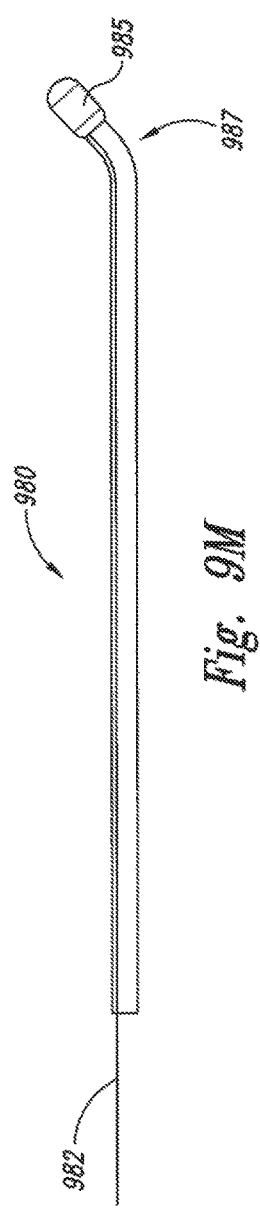
Figure 9N:
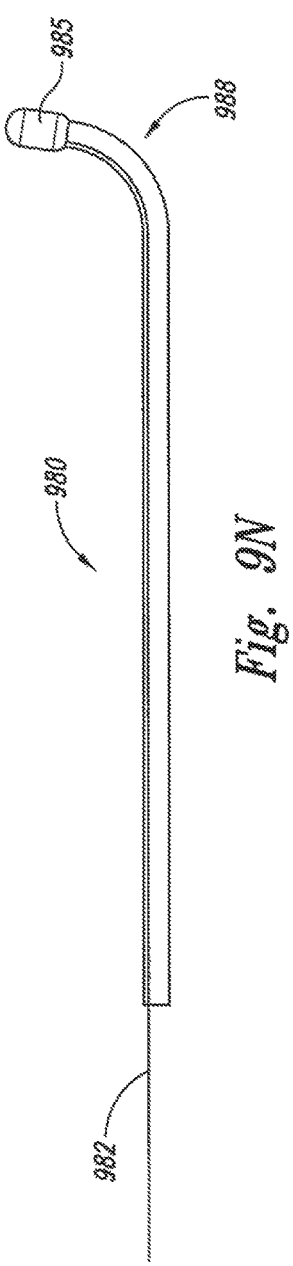

FIGS. 9A-9N are schematic side views illustrating additional embodiments of intravascular systems including one or more wall-contact electrodes, blood flow occlusion features, and/or thermal fluid injection functions. The embodiments described below with reference to FIGS. 9A-9N are described as monopolar devices, but it should be understood that any (or all) of the embodiments may be configured or operated as bipolar devices. Furthermore, although blood flow occlusion and thermal fluid injection are described in combination with wall-contact electrode(s), it should be understood that such occlusion and injection features may be provided in combination with electrode(s) that do not contact the vessel wall.

As discussed previously, in addition or as an alternative to utilizing the patient's blood as a heat sink to create different heat transfer rates between target neural fibers and non-target tissue of the wall of the vessel within which thermal energy is delivered, a thermal fluid (hot or cold) may be injected, infused or otherwise delivered into the vessel. The thermal fluid may further remove excess thermal energy and protect the non-target tissues. When delivering thermal therapy via heating, the thermal fluid may, for example, comprise chilled or room temperature saline (e.g., saline at a temperature lower than the temperature of the vessel wall during the therapy delivery). The thermal fluid may be injected through the device catheter or through a guide catheter at a location upstream from an energy delivery element, or at other locations relative to the tissue for which protection is sought. The thermal fluid may be injected in the presence of blood flow or with blood flow temporarily occluded. The occlusion of blood flow in combination with thermal fluid delivery may facilitate good control over the heat transfer kinetics along the non-target tissues, as well as injection of fluid from a downstream location.

FIGS. 9A and 9B illustrate an apparatus 800 including a catheter 802 having a positioning element 804 that can be used to position the apparatus within the vessel and/or to occlude blood flow. The positioning element 804, for example, can be an inflatable balloon. The apparatus 800 can further include one or more active monopolar electrodes 810 located proximally from the positioning element 804 such that inflation of the positioning element 804 blocks blood flow downstream of the electrode assembly 806. The electrode assembly 806 includes multiple extensions 814, and it should be understood that any desired number of extensions may be provided, including a single extension. The monopolar electrode(s) 810 are utilized in combination with a remote electrode, such as a ground pad, positioned external to the patient. The apparatus 800 can also include an infusion port 805 between the positioning element 804 and the electrode assembly 806.

As shown in FIG. 9A, the catheter 802 can be advanced within the renal artery RA in a reduced profile delivery configuration. Referring to FIG. 9B, once properly positioned at the treatment site, the electrode assembly 806 can be actively expanded, or it may self-expand by removing a sheath, the guide catheter 803, or another type of restraint from the electrode(s) 810. The expanded electrode assembly 806 contacts the vessel wall. The positioning element 804 can be expanded (before, during, or after expansion of the electrode assembly 806) to properly position the electrode assembly 806 within the vessel and/or to occlude blood flow within the renal artery RA downstream of the electrode assembly 806. A monopolar electric field may be delivered between the active electrode(s) 810 and the external ground. Alternatively, a biopolar electric field can be generated between any two electrodes 810. The electric field may, for example, comprise a pulsed or continuous RF electric field that thermally induces neuromodulation (e.g., necrosis or ablation) in the target neural fibers. The thermal therapy may be monitored and controlled, for example, via data collected with thermocouples, impedance sensors, or other sensors, which may be incorporated into electrode(s) 810.

To increase the power that may be delivered or the duration of the thermal treatment without undesirably affecting non-target tissue, a thermal fluid infusate I can be injected through injection port 805 of the catheter 802 to cool the non-target tissue. This is expected to mitigate undesired effects in the non-target tissue. The infusate I, for example, can include chilled saline that removes excess thermal energy from the wall of the vessel during thermal therapy.

Convective or other heat transfer between the non-target vessel wall tissue and the infusate I may facilitate cooling (or heating) of the vessel wall at a faster rate than cooling (or heating) occurs at the target neural fibers. This difference in the heat transfer rates between the wall of the vessel and the target neural fibers may be utilized to modulate the neural fibers. Furthermore, when utilizing a pulsed thermal therapy, the accelerated heat transfer at the wall relative to the neural fibers may allow for relatively higher energy or longer duration therapies (as compared to continuous thermal therapies). Also, the interval between pulses may be used to monitor and/or control effects of the therapy.

FIG. 9C is a schematic side view illustrating another embodiment of an apparatus 820 including wall-contact electrodes 810, flow occlusion, and thermal fluid injection. In the embodiment shown in FIG. 9C, an occlusion element 804 is coupled to the guide wire G, which may comprise an inflation lumen, and the infusate I is delivered through a distal outlet of the catheter 802. The occlusion element 804 alternatively may be coupled to a separate catheter or sheath (not shown) rather than to the guide wire G. Also, the infusate I may, for example, be delivered through the guide wire lumen or through an additional lumen or annulus of the catheter 802. FIG. 9D illustrates another embodiment of an apparatus 830 where occlusion element 804 is positioned proximal or upstream of the electrode assembly 806, and the infusate I is delivered at a position distal of the occlusion element 804 but proximal of the electrode assembly 806.

FIG. 9E is a schematic side view illustrating yet another embodiment of an apparatus 840 with occlusion elements 804 (two are shown as occlusion elements 804a and 804b) positioned both proximal and distal of the electrode assembly 806. In addition to having a first injection port 805a, the catheter 803 includes an aspiration port 805b. Separate lumens can extend through the catheter for injection and aspiration of the infusate I via the injection ports 805a and 805b. Providing both injection and aspiration of the infusate facilitates good control over the flow dynamics of the infusate, and thereby the heat transfer kinetics of the infusate I. For example, providing aspiration and injection at the same rate can provide consistent heat transfer kinetics between the vessel and the electrode(s) 806.

FIG. 9F illustrates still yet another embodiment of an apparatus 850 having a catheter 852 including a wall-contact electrode 856 that can be moved into contact with the vessel wall via an elongated member 857. In this embodiment, the elongated member 857 is distally connected to the catheter 852 in the vicinity of the electrode 856. The elongated member 857 may be configured for self or mechanical expansion, or it may extend through a port 805 of the catheter 852 and through a lumen of the catheter to a proximal location for manipulation by a medical practitioner. The proximal section of the elongated member 857 may be advanced relative to the catheter 852 by the medical practitioner such that the member assumes the illustrated curved profile.

Upon expansion of the elongated member, the catheter 852 is deflected such that the electrode 856 coupled to the catheter shaft contacts the vessel wall. Optionally, the positioning element 804 may be expanded to facilitate positioning of the electrode 856 via the elongated member 857 and/or to block flow through the vessel. The positioning element 804 can be coupled to the guide or delivery catheter 803. Infusate I optionally may be delivered through the catheter 852 as shown.

FIGS. 9G-9N are partially schematic side views illustrating an embodiment of a probe or catheter 900 including a shaped or self-expanding or mechanically-activated electrode suitable for use in the system 100 of FIGS. 3A and 3B. FIG. 9G, for example, illustrates the probe or catheter 900 in a reduced profile configuration for delivery to the treatment site, and FIG. 9H illustrates a portion of the probe 900 in an expanded or uncompressed state. Referring to FIGS. 9G and 9H together, the probe 900 can include a shaft 904, an electrode 906, an intermediate portion or section 908 between the shaft 904 and the electrode 906, and a guide catheter or sheath 910 (e.g., a 5 French guide catheter) covering and releasably carrying the shaft 904 and the intermediate portion 908. The intermediate portion 908 can rest within the sheath 910 in a compressed state (i.e., the curved or shaped region is substantially flattened or otherwise straightened by the inner wall of the sheath 910) during delivery to the treatment site (FIG. 9G). When the sheath 910 is retracted, the intermediate portion 908 will expand to its unconstrained arched or curved shape (FIG. 9H). The curved or shaped profile of the intermediate portion 908 facilitates contact between the electrode 906 and the corresponding vessel wall. This process is described in greater detail below with reference to FIG. 9J.

As best seen in the reduced profiled configuration of FIG. 9G, the shaft 904 and the intermediate portion 908 can optionally have an internal space 912 (not shown), and the probe 900 can further include wires 112 (identified individually as 112a and 112b) coupled to the intermediate portion 908. The wires 112a-b electrically couple the electrode 906 to the field generator 110 and may be comprised of thermocouple wires. As discussed in more detail below, the electrode 906 can deliver an electric field supplied by the field generator 110 via the wires 112 to the wall of the corresponding body lumen.

Referring back to FIGS. 9G and 9H together, the shaft 904 can be a generally cylindrical tube constructed from one or more biocompatible materials (e.g., plastic, metals, alloys, and ceramics). The shaft 904 can also include a more flexible region or section 904a at a distal portion of the shaft 904 and configured to allow the probe 900 to flex or contort during use. For example, the flexible region 904a can allow the probe 900 to make the relatively sharp turn from the aorta to the renal artery during delivery of the electrode 906 to the treatment site. In one embodiment, the flexible region 904a can include a braided shaft without the support of a hypotube or other support structure which may be incorporated into the shaft 904. As shown in FIG. 9H, the flexible region 904a has a length $L_1$ of about 7 cm. In other embodiments, however, flexible region 904a can have a length $L_1$ of from about 2 cm to about 140 cm (the entire working length of the shaft 904 could be generally flexible). In still other embodiments, the shaft 904 and/or the flexible region 904a can have a different arrangement and/or configuration.

The probe 900 can have a working or effective length $L_2$ of from about 55 cm to about 140 cm. As used herein, "working length" and "effective length" are defined as the length of the probe 900 (e.g., the shaft 904, the intermediate portion 908, and the electrode 906) that will fit inside a patient's body. In configurations where a 55 cm guide catheter is used to facilitate delivery of the probe 900, the working or effective length may be from about 60 cm to about 80 cm. In configurations where a 90 cm guide catheter is used to facilitate delivery of the probe 900, the working or effective length may be from about 95 cm to about 120 cm. In the illustrated embodiment, for example, the probe 900 has a working or effective length $L_2$ of about 108 cm and is configured for use with a sheath 910 having a length of about 90 cm. In other embodiments, however, the probe 900 can have a different working length $L_2$ and/or be configured for use with a sheath having a different dimension and/or configuration.

The electrode 906 includes a band 914 constructed from a first metal (e.g., platinum or iridium) and a second metal 916 disposed inside the band 914. The band 914 can be generally cylindrical or have another suitable shape. The second metal 916 can be the same as the first metal, or the second metal 916 can be a different metal or metal alloy. The wires are electrically coupled to one another. For example, the wires can be electrically connected directly or connected via the first and/or second metal. Thus, the electrode 906 can deliver an electric field supplied from the field generator 110 via the wires 112a-b to the wall of the body lumen. In an alternative embodiment, a single wire is used instead of a pair of wires.

The electrode 906 can also measure temperature (via a thermocouple or thermistor, or other temperature sensing elements), impedance or another parameter while delivering the electric field to the tissue. For example, voltage and current of the supplied electric field can be measured, and a resistance or impedance can be calculated according to Ohm's law.

One expected advantage of an embodiment where only impedance is measured is that only one wire is needed for the probe 900. If the probe 900 includes a temperature sensor electrically connected to the electrode, then at least one more wire must be used. In this case, a total of two wires can be used to deliver energy, measure impedance and measure temperature. If the probe 900 includes a temperature sensor electrically independent from the electrode then at least one more wire must be used. Additionally, more than one temperature sensors may be used to make additional temperature measurements. The additional wires can add to the size and complexity of the probe 900 and increase the potential for a malfunction.

Although the illustrated electrode 906 includes the band 914, the electrode 906 can have other configurations. For example, the electrode 906 can include a coil constructed from a first metal wrapped around a core constructed from a second metal. One expected advantage of having a coil is that the coil can reduce stress due to heat expansion when measuring temperature. In another embodiment, the electrode can be formed from a single metal or other conductor without the band.

FIG. 9I is an exploded view of a portion of the probe 900 taken from the area 9I of FIG. 9H. The intermediate portion 908 may be comprised of a solid wire, ribbon, cylindrical tube, or coil constructed from stainless steel, nitinol, plastic or another suitable material (or combinations thereof) that can bend or otherwise flex or be actively directed to facilitate contact between the electrode 906 and the corresponding vessel wall. In the illustrated embodiment, the intermediate portion 908 flexes or bends to locate the electrode 906 at a dimension Y from a longitudinal axis S of the shaft 904. The dimension Y can vary from about 2 mm to about 20 mm. In some configurations, the Y dimension can be from about 10 mm to about 20 mm. In the illustrated embodiment, for example, the dimension Y is about 16 mm. By way of example, the average diameter of a human renal artery is from about 3 mm to about 8 mm. Accordingly, if the shaft 904 was positioned adjacent to a wall of an artery having an 8 mm diameter, the intermediate section 908 would have enough flexure or arch for the electrode 906 to contact the opposite wall of the artery. In other embodiments, however, the dimension Y can have a different value and maybe oversized to facilitate contact in a straight or curved vessel.

The intermediate portion 908 is also configured to locate the electrode 906 at a dimension X from a distal portion 904b of the shaft 904. The dimension X can vary based, at least in part, on the material of which the intermediate portion 908 is composed (e.g., stainless steel or nitinol) and the desired working or effective length for the probe 900. For example, the dimension X of the intermediate portion 908 should be configured and sized to provide sufficient wall contact pressure such that the electrode 906 can create the desired treatment effect.

In alternative embodiments, a pull or push wire can be used to actively flex the intermediate portion to facilitate placement of the electrode. For example, as illustrated in FIGS. 9L to 9N, an electrode tip 985 of a probe 980 can be deflected or steered using an actuator wire 982. The actuator wire 982 can be pulled from a first position or position of no deflection 986, as shown in FIG. 9L, to a second position of slight deflection 987, as shown in FIG. 9M, to a third position of substantial deflection 988, as shown in FIG. 9N. The variable deflection of the probe 980 can be particularly helpful, for example, when attempting to achieve wall contact in a curved vessel.

Referring back to FIG. 9I, the shaft 904 has an outer diameter D of from approximately 0.014 inches to approximately 0.085 inches. The outer diameter D of the shaft 904 can vary based, at least in part, on the outer diameter of the electrode 906. In the illustrated embodiment, for example, the shaft 904 has an outer diameter D of about 0.040 inches, which corresponds to one particular configuration of the electrode 906.

The electrode 906 has an outer diameter E of from about 0.020 inches to about 0.085 inches. In the illustrated embodiment, for example, the electrode 906 has an outer diameter E of about 0.049 inches. These dimensions can vary, however, from a practical standpoint, the outer diameter E of the electrode 906 can be no bigger than the inner diameter of the sheath or guide catheter (e.g., the sheath 910) through which the electrode 906 is delivered. In one particular example, an 8 French guide catheter (which has an inner diameter of 0.091 inches) would likely be the largest catheter used to access the renal artery. Thus, an electrode used in this situation would have an outer diameter E at least approximately less than 0.085 inches.

In an alternative embodiment, the catheter can be configured such that the sheath does not cover the entire electrode, but is rather used only to substantially straighten the intermediate portion of the catheter to facilitate delivery to the treatment location. In such configurations, the distal end of the sheath will abut the proximal end of the electrode. Accordingly, it would not be necessary for the electrode size to be limited by the inner diameter of the sheath.

FIG. 9J is a schematic side view of an embodiment of an intravascular apparatus 950 including the probe 900 with the shaped or self-expanding electrode 906. The electrode 906 can be delivered to a treatment site within the sheath 910, and then it can move to a preselected shape after it has been removed from the lumen of the sheath 910. For example, the electrode 906 can be removed from the sheath 910 by advancing the shaft 904 and/or retracting the shaft 904. The electrode 906 contacts the vessel wall for delivery of therapy. Optionally, the shaft 904 may be rotated to rotate the electrode 906 relative to the vessel wall and angularly reposition the electrode 906. The therapy can be delivered at a singular angular position or at multiple angular positions. Infusate I optionally may be delivered through the sheath 910 as shown.

It should be understood that in any of the embodiments disclosed herein, a guide wire can be optionally employed to facilitate delivery and/or removal of the probe. In such embodiments, the probe may be additionally configured with structural enhancements (e.g., guide wire lumen) for accommodating the use of a guide wire.

Additionally or alternatively, the apparatus 950 can include multiple angularly spaced electrodes 906 positioned within the vasculature, as shown in FIG. 9K. In addition to angular spacing, the electrodes 906 may be longitudinally spaced to facilitate treatment over a longitudinal segment of the vessel (e.g., to achieve a circumferential treatment along the longitudinal segment rather than along a cross-section).

In addition to extravascular and intravascular systems for thermally-induced renal neuromodulation, intra-to-extravascular systems may be provided. The intra-to-extravascular systems may, for example, have electrode(s) that are delivered to an intravascular position, and then at least partially passed through/across the vessel wall to an extravascular position prior to delivery of a thermal energy field. Intra-to-extravascular positioning of the electrode(s) may place the electrode(s) in closer proximity to target neural fibers for delivery of a thermal energy field, as compared to fully intravascular positioning of the electrode(s). Applicants have previously described intra-to-extravascular pulsed electric field systems, for example, in co-pending U.S.

patent application Ser. No. 11/324,188, filed Dec. 29, 2005, which is incorporated herein by reference in its entirety.

Figure 10:
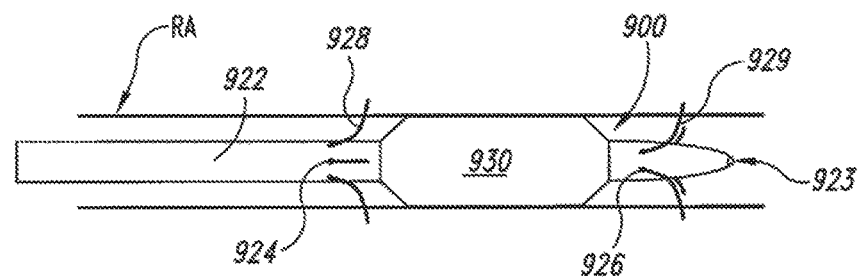
FIG. 10 is a schematic side view, partially in section, illustrating an example of an intra-to-extravascular system for thermally-induced renal neuromodulation configured in accordance with an embodiment of the disclosure.

FIG. 10 is a schematic side view illustrating an embodiment of an intra-to-extravascular ("ITEV") system 900 for thermally-induced renal neuromodulation. The ITEV system 900 includes a catheter 922 having (a) a plurality of proximal electrode lumens terminating at proximal side ports 924, (b) a plurality of distal electrode lumens terminating at distal side ports 926, and (c) a guidewire lumen 923. The catheter 922 preferably includes an equal number of proximal and distal electrode lumens and side ports. The ITEV system 900 also includes proximal needle electrodes 928 that can be advanced through the proximal electrode lumens and the proximal side ports 924, as well as distal needle electrodes 929 that may be advanced through the distal electrode lumens and the distal side ports 926. Alternatively, the embodiment illustrated in FIG. 10 can be configured with a single needle electrode configured for monopolar energy delivery.

The catheter 922 includes an optional expandable positioning element 930. The positioning element 930 can include, for example, an inflatable balloon or an expandable basket or cage. In use, the positioning element 930 may be expanded prior to deployment of the needle electrodes 928 and 929 to position or center the catheter 922 within the patient's vessel (e.g., within renal artery RA). Centering the catheter 922 is expected to facilitate delivery of all needle electrodes 928 and 929 to desired depths within/external to the patient's vessel (e.g., to deliver all of the needle electrodes 928 and 929 to approximately the same depth). In the embodiment illustrated in FIG. 10, the positioning element 930 is between the proximal side ports 924 and the distal side ports 926 and, accordingly, the positioning element 930 is between the delivery positions of the proximal and distal electrodes. However, it should be understood that the positioning element 930 additionally or alternatively can be positioned at a different location or at multiple locations along the length of the catheter 922 (e.g., at a location proximal of the side ports 924 and/or at a location distal of the side ports 926).

As shown in FIG. 10, the catheter 922 may be advanced to a treatment site within the patient's vasculature over a guidewire (not shown) via the lumen 923. During intravascular delivery, the needle electrodes 928 and 929 may be positioned such that their non-insulated and sharpened distal regions are positioned within the proximal and distal lumens, respectively. Once at a treatment site, a medical practitioner may advance the electrodes 928 and 929 via their proximal regions that are located external to the patient. Such advancement causes the distal regions of the electrodes 928 and 929 to exit side ports 924 and 926, respectively, and pierce the wall of the patient's vasculature such that the electrodes are positioned extravascularly via an ITEV approach.

The proximal electrodes 928 can be connected to a field generator (not shown) as active electrodes, and the distal electrodes 929 can serve as return electrodes. In this manner, the proximal and distal electrodes 928 and 929 form bipolar electrode pairs that align the thermal energy field with a longitudinal axis or direction of the patient's vasculature. The distal electrodes 929 alternatively may comprise the active electrodes and the proximal electrodes 928 may comprise the return electrodes. Furthermore, the proximal electrodes 928 and/or the distal electrodes 929 may both comprise active and return electrodes. Further still, the proximal electrodes 928 and/or the distal electrodes 929 may be utilized in combination with an external ground for delivery of a monopolar thermal energy field. Any combination of active and distal electrodes may be utilized.

When the electrodes 928 and 929 are connected to a field generator and positioned extravascularly (and with the positioning element 930 optionally expanded) delivery of the thermal energy field can provide the desired renal neuromodulation via heating. After achievement of the desired thermally-induced renal neuromodulation, the electrodes 928 and 929 can be retracted within the proximal and distal lumens, and the positioning element 930 can be collapsed for retrieval. The ITEV system 900 can then be removed from the patient to complete the procedure. Additionally or alternatively, the system 900, or any system disclosed herein, may be repositioned to provide therapy at another treatment site, such as to provide bilateral renal neuromodulation.

Cooling elements, such as convective cooling elements, may be utilized to protect non-target tissues like smooth muscle cells from thermal alteration during thermally-induced renal neuromodulation via heat generation. Non-target tissues may be protected by focusing the thermal energy on the target neural fibers such that an intensity of the thermal energy is insufficient to induce thermal alteration in non-target tissues distant from the target neural fibers.

Although FIGS. 3A-8B and 10 illustrate bipolar systems, it should be understood that monopolar systems alternatively may be utilized as shown in FIGS. 9A-9N. For example, an active monopolar electrode may be positioned intravascularly, extravascularly, or intra-to-extravascularly in proximity to target neural fibers that contribute to renal function. A return electrode may be attached to the exterior of the patient or positioned in the patient apart from the active electrodes. Finally, a thermal energy field may be delivered between the in vivo monopolar electrode and the remote electrode to effectuate desired thermally-induced renal neuromodulation. Monopolar apparatus additionally may be utilized for bilateral renal neuromodulation.

The embodiments described above with reference to FIGS. 3A-10 are directed generally to methods and systems for thermally-induced renal neuromodulation via delivery of thermal energy fields that modulate the target neural fibers. However, it should be understood that alternative methods and systems for thermally-induced (via both heating and cooling) renal neuromodulation may be provided. For example, electric fields may be used to cool and modulate the neural fibers with thermoelectric or Peltier elements. Also, thermally-induced renal neuromodulation optionally may be achieved via resistive heating, via delivery of a heated or chilled fluid (see FIGS. 11 and 13), via a Peltier element (see FIG. 12), etc. Thermally-induced renal neuromodulation additionally or alternatively may be achieved via application of high-intensity focused ultrasound to the target neural fibers (see FIGS. 14A, 14B, and 15). Additional and alternative methods and systems for thermally-induced renal neuromodulation may be used in accordance with the present disclosure.

Figure 11:
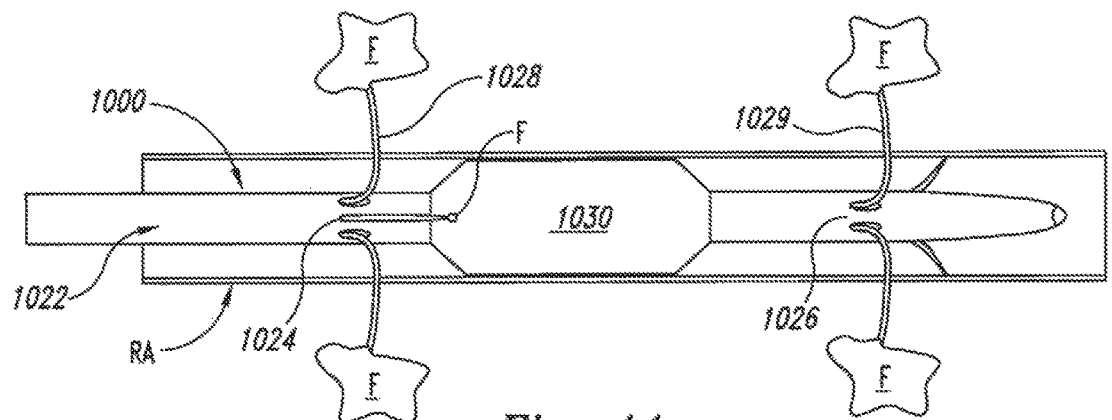
FIG. 11 is a schematic side view, partially in section, illustrating an embodiment of an apparatus configured for thermally-induced renal neuromodulation via application of thermal energy.

FIG. 11, for example, is a schematic side view of an alternative embodiment of an apparatus 1000 for thermally-induced neuromodulation via application of thermal energy. In this embodiment, the electrodes 328 and 329 of FIG. 10 have been replaced with infusion needles 1028 and 1029, respectively. A thermal fluid F may be delivered through the infusion needles 1028 and 1029 to the target neural fibers. The thermal fluid F may be heated in order to raise the temperature of the target neural fibers above a desired threshold. For example, the temperature of the neural fibers can be raised above a body temperature of about 37° C., or above a temperature of about 45° C. Alternatively, the thermal fluid F may be chilled to reduce the temperature of the target neural fibers below a desired threshold. For example, the neural fibers can be cooled to below the body temperature of about 37° C., or further cooled below about 20° C., or still further cooled below a freezing temperature of about 0° C. As will be apparent, in addition to intra-to-extravascular delivery of a thermal fluid, the thermal fluid F may be delivered intravascularly (e.g., may inflate and/or be circulated through a balloon member), extravascularly (e.g., may be circulated through a vascular cuff), or a combination thereof.

In addition or as alternative to injection of a thermal fluid to the target neural fibers through infusion needles 1028 and 1029, an alternative neuromodulatory agent, such as a drug or medicament, may be injected to modulate, necrose or otherwise block or reduce transmission along the target neural fibers. Examples of alternative neuromodulatory agents include, but are not limited to, phenol and neurotoxins, such as botulinum toxin. Additional neuromodulatory agents, per se known, will be apparent to those of skill in the art.

Figure 12:
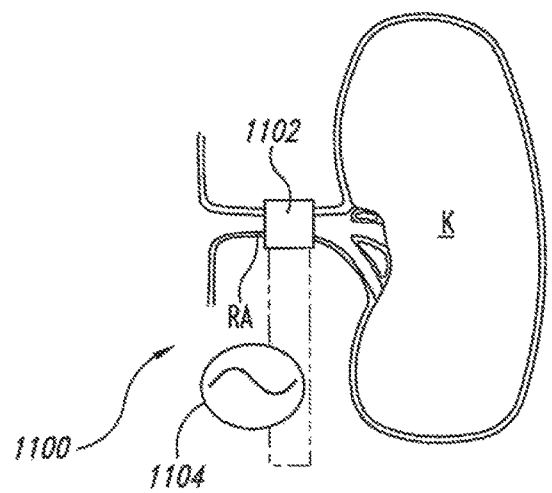
FIG. 12 is a schematic side view, partially in section, illustrating an embodiment of an apparatus for thermally-induced renal neuromodulation comprising a thermoelectric element suitable for application of thermal energy to target neural fibers.

FIG. 12 is a schematic side view illustrating still another embodiment of an apparatus 1100 for thermal renal neuromodulation via application of thermal energy to the target neural fibers. The apparatus 1100 includes a renal artery cuff 1102 having one or more integrated thermoelectric elements that are electrically coupled to an internal or external power supply 1104. The thermoelectric element(s) utilize the well-known Peltier effect (i.e., the establishment of a thermal gradient induced by an electric voltage) to achieve thermal renal neuromodulation.

An electric current is passed from the power supply 1104 to the thermoelectric element of the cuff 1102. The thermoelectric element can include two different metals (e.g., a p-type and an n-type semiconductor) that are connected to each other at two junctions. The current induces a thermal gradient between the two junctions, such that one junction cools while the other is heated. Reversal of the polarity of the voltage applied across the two junctions reverses the direction of the thermal gradient. Either the hot side or the cold side of the thermoelectric element faces radially inward in order to heat or cool, respectively, the target neural fibers that travel along the renal artery to achieve thermal renal neuromodulation. Optionally, the radially outward surface of the thermoelectric element may be insulated to reduce a risk of thermal alteration to the non-target tissues. The cuff 1102 may include one or more temperature sensors, such as thermocouples, for monitoring the temperature of the target neural fibers and/or of the non-target tissues, wherein the monitored data may be used as feedback to control the delivery of therapy.

Figure 13:
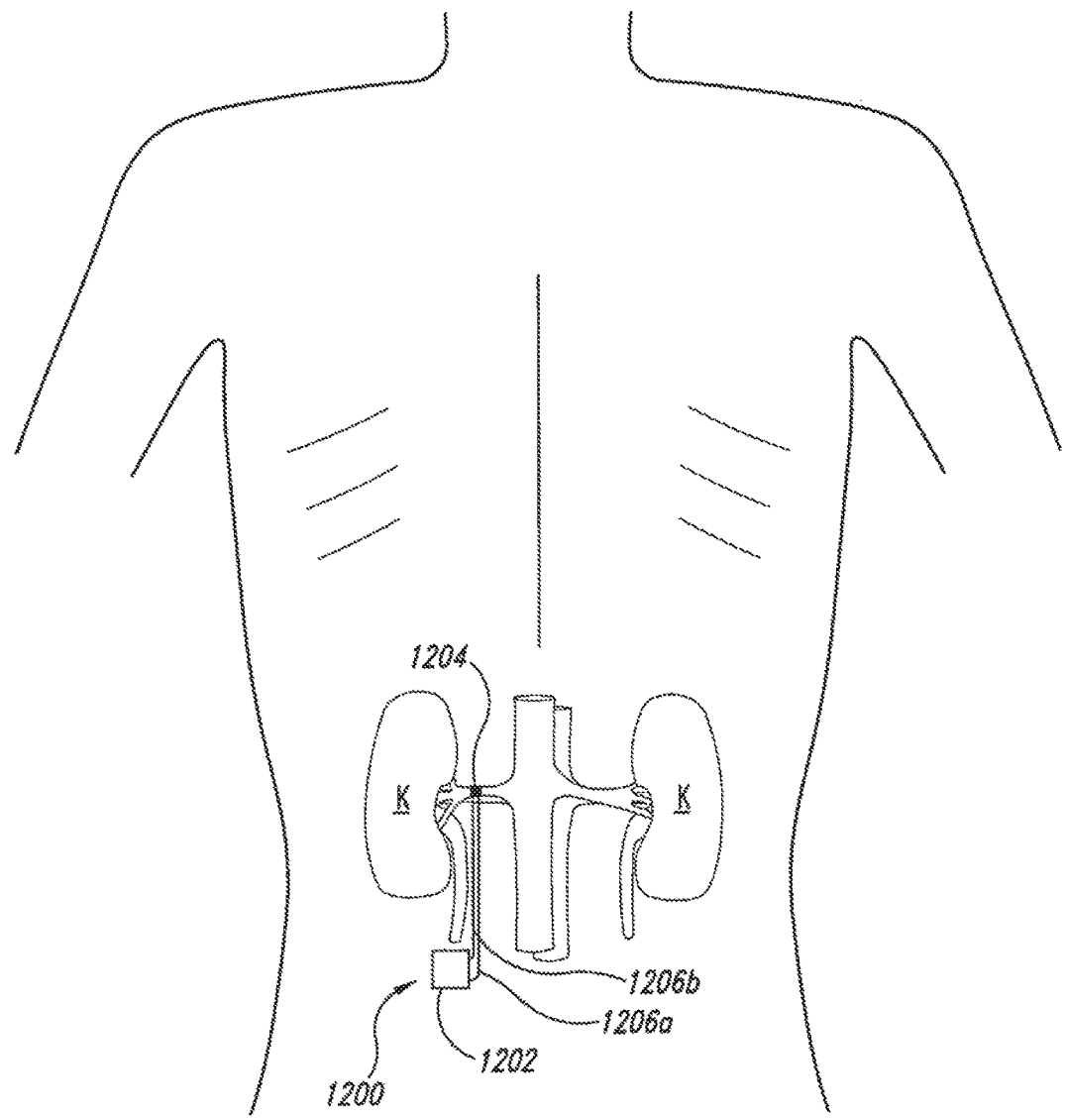
FIG. 13 is a schematic side view, partially in section, illustrating another embodiment of an apparatus for thermally-induced renal neuromodulation comprising a thermoelectric element.

FIG. 13 illustrates yet another embodiment of an apparatus 1200 utilizing the Peltier effect. The apparatus 1200 includes an implanted or external pump 1202 connected to a renal artery cuff 1204 via an inlet fluid conduit 1206a and an outlet fluid conduit 1206b. The inlet fluid conduit 1206a transfers fluid from the pump 1202 to the cuff 1204, while the outlet fluid conduit 1206b transfers fluid from the cuff 1204 to the pump 1202 to circulate the fluid through the cuff 1204. A reservoir of fluid may be located in the cuff 1204, the pump 1202, and/or in the fluid conduits 1206a and 1206b.

The pump 1202 can further include one or more thermoelectric or other thermal elements in heat exchange contact with the fluid reservoir for cooling or heating the fluid that is transferred to the cuff 1204 to thermally modulate the target neural fibers. The apparatus 1200 optionally may have controls for automatic or manual control of fluid heating or cooling, as well as fluid circulation within the cuff 1204. Furthermore, the apparatus 1200 may include a temperature and/or renal sympathetic neural activity monitoring or feedback control. Although the apparatus 1200 of FIG. 13 is shown unilaterally treating neural fibers innervating a single kidney, it should be understood that bilateral treatment of neural fibers innervating both kidneys alternatively may be provided.

Thermal renal neuromodulation alternatively may be achieved via pulsed or continuous high-intensity focused ultrasound. Furthermore, the ultrasound may be delivered over a full 360° (e.g. when delivered intravascularly) or over a radial segment of less than 360° (e.g., when delivered intravascularly, extravascularly, intra-to-extravascularly, or a combination thereof).

Figure 14A:
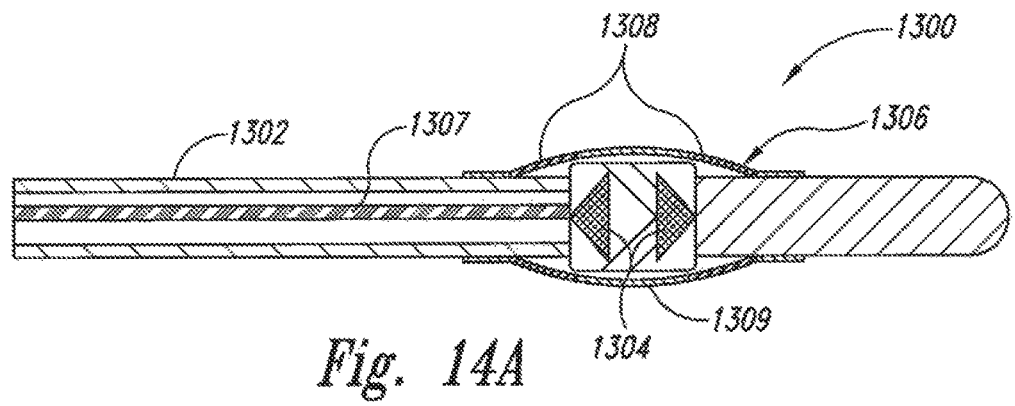
FIGS. 14A and 14B are schematic side views, partially in section, illustrating an embodiment of an apparatus for thermally-induced renal neuromodulation via high-intensity focused ultrasound.
Figure 14B:
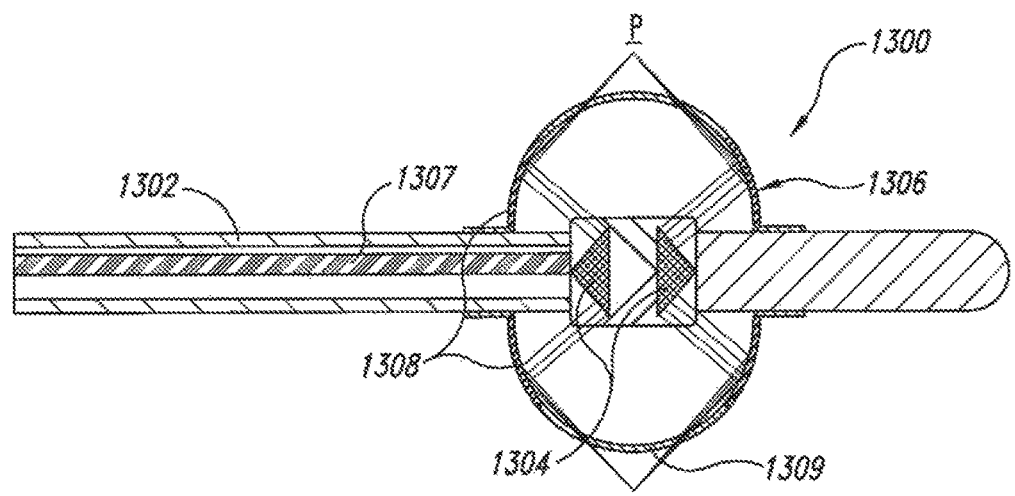

FIGS. 14A and 14B, for example, are schematic side views illustrating an embodiment of an ultrasonic apparatus 1300 including a catheter 1302, one or more ultrasound transducers 1304 positioned along the shaft of the catheter 1302, and an inflatable balloon 1306 around the transducers 1304. FIG. 14A illustrates the apparatus 1300 in a reduced delivery and retrieval configuration, and FIG. 14B illustrates the apparatus 1300 in an expanded deployed configuration. The ultrasound transducers 1304 are coupled to an ultrasound signal generator (not shown) via conductors 1307. The balloon 1306 can have an acoustically reflective portion 1308 for reflecting an ultrasound wave and an acoustically transmissive portion 1309 through which the ultrasonic energy can pass. In this manner, the wave may be focused as shown at a focal point or radius P positioned a desired focal distance from the catheter shaft. In an alternative embodiment, the transducers 1304 may be attached directly to the balloon 1306.

The focal distance may be specified or dynamically variable such that the ultrasonic wave is focused at a desired depth on target neural fibers outside of the vessel. For example, a family of catheter sizes may be provided to allow for a range of specified focal distances. A dynamically variable focal distance may be achieved, for example, via calibrated expansion of the balloon 1306.

Focusing the ultrasound wave may produce a reverse thermal gradient that protects the non-target tissues and selectively affect the target neural fibers to achieve thermal renal neuromodulation via heating. As a result, the temperature at the vessel wall may be less than the temperature at the target tissue.

Figure 15:
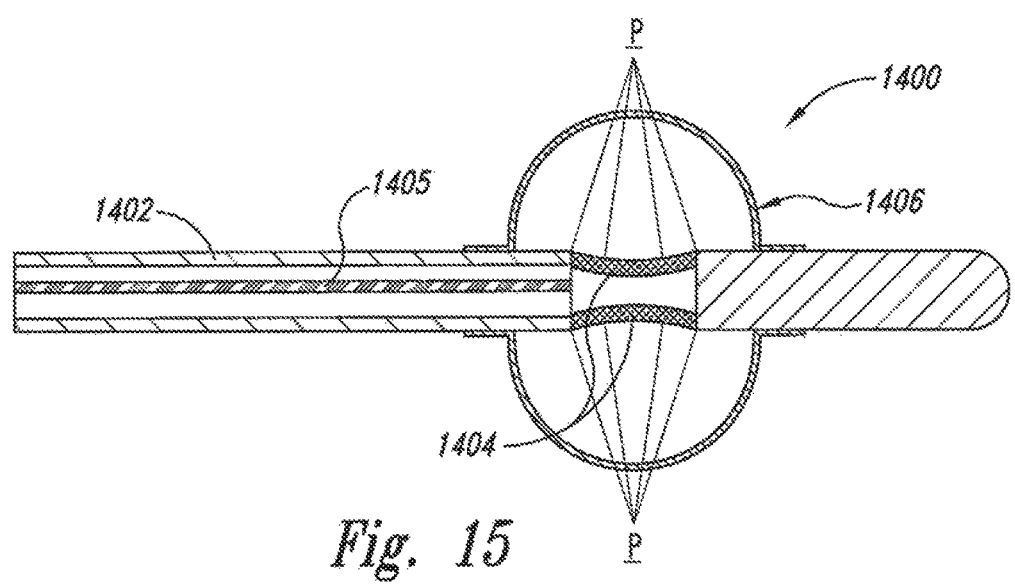
FIG. 15 is a schematic side view, partially in section, illustrating an alternative embodiment of the apparatus of FIGS. 14A and 14B.

FIG. 15 illustrates still another embodiment of an ultrasonic apparatus 1400 having a catheter 1402, a conductor 1403, and concave ultrasound transducers 1404. The concave ultrasound transducers 1404 direct the energy to a specific focal point P. As such, the concave transducers 1404 are self-focusing and eliminate the need for reflective portions on the balloon 1406 (e.g., the balloon may be acoustically transmissive at all points).

The systems described above with respect to FIGS. 3A-15 optionally may be used to quantify the efficacy, extent, or cell selectivity of thermally-induced renal neuromodulation in order to monitor and/or control the neuromodulation. As discussed previously, the systems can further include one or more sensors, such as thermocouples or imaging transducers, for measuring and monitoring one or more parameters of (a) the system, (b) target neural fibers, and/or (c) non-target tissues. For example, a temperature rise or drop above or below certain thresholds is expected to thermally ablate, non-ablatively alter, freeze, or otherwise alter the target neural fibers to thereby modulate the target neural fibers.

It should be understood that any of the methods, apparatuses, and systems disclosed herein can be modified or configured for cooling or freezing treatments which modulate neural fibers. For example, any of the probes disclosed herein can be modified to deliver cryotherapy to the target neural fibers with either an intravascular, extravascular or ITEV approach.

D. Modules and Methods for Controlling Thermally-Induced Renal Neuromodulation With the treatments disclosed herein for delivering therapy to target tissue, it may be beneficial for energy to be delivered to the target neural structures in a controlled manner. The controlled delivery of energy will allow the zone of thermal treatment to extend into the renal fascia while minimizing undesirable energy delivery or thermal effects to the vessel wall. A controlled delivery of energy may also result in a more consistent, predictable and efficient overall treatment. Accordingly, it may be beneficial to incorporate a controller or computer system having programmed instructions for delivering energy to tissue into the energy delivery system. Additionally, these programmed instructions may comprise an algorithm for automating the controlled delivery of energy. Alternatively, the delivery of energy to target tissue can be controlled manually by an operator or the physician administering treatment.

Figure 16:
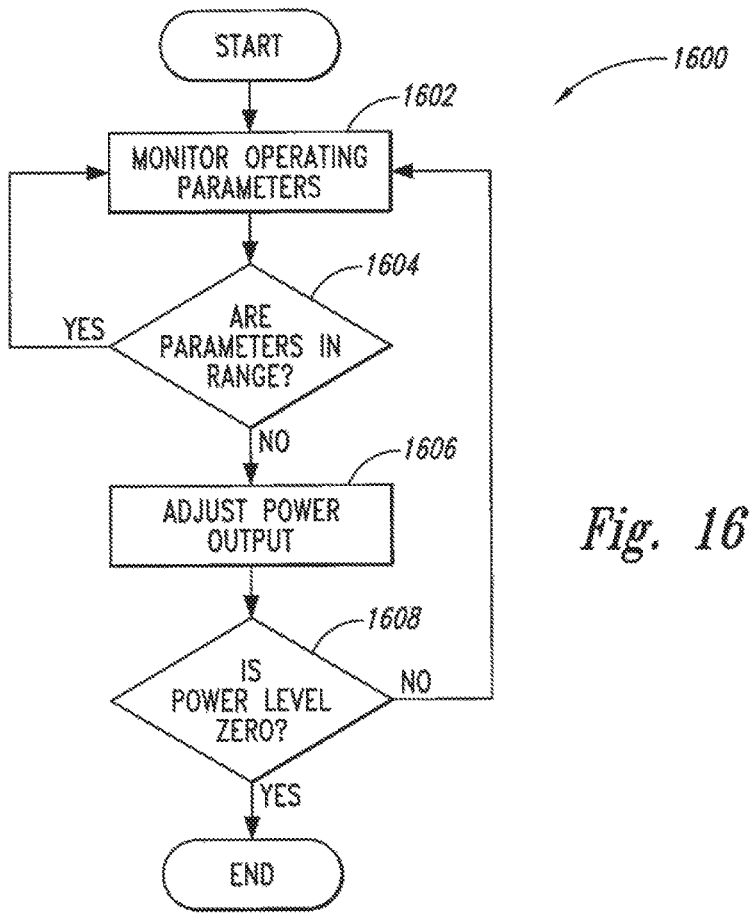
FIG. 16 is a flow diagram illustrating a method for controlling an energy delivery process for thermally-induced renal neuromodulation.

In one embodiment, for example, a controller can command a power generator (e.g., the field generator 110 of FIGS. 3A and 3B) in accordance with an algorithm comprising various power delivery profiles. FIG. 16, for example, is a flow chart illustrating a method 1600 of controlling such power delivery processes. The method 1600 can be implemented as a conventional computer program for execution by the processor 114 of FIG. 3A or another suitable device (e.g., the field generator 110). The method 1600 can also be implemented manually by an operator.

As illustrated in FIG. 16, after treatment is initiated, the first stage 1602 of the method 1600 includes monitoring certain operating parameters (e.g., temperature, time, impedance, power, etc.). While it is preferred that these operating parameters are monitored continuously, they can alternatively be monitored periodically. At stage 1604, the method 1600 includes checking the monitored parameters against predetermined parameter profiles to determine whether the parameters individually or in combination fall within the ranges set by the predetermined parameter profiles. For example, temperature can be monitored and compared to a predetermined temperature value. Alternatively, both temperature and impedance can be monitored and compared to a predetermined parameter profile of both temperature and impedance. If the monitored parameters fall within the ranges set by the predetermined parameter profiles, then treatment is continued at the same settings and the operating parameters continue to be monitored.

When it is determined that one or more parameters or multiple parameters in combination fall outside a predetermined parameter profile, then the method 1600 calls for an adjustment to the system's power output at stage 1606. The direction (i.e., increase or decrease) and degree of the power output adjustment can be determined by a routine utilizing the monitored parameters and how they compare against other predetermined parameter profiles. For example, if temperature and time are monitored and it is determined that the monitored temperature and time exceed a predetermined parameter profile of temperature and time, then power delivery may be reduced. Alternatively, if one or more monitored parameters or multiple monitored parameters in combination falls short of a predetermined parameter profile, then power delivery may be increased. As shown in FIG. 16, treatment will continue until power delivery has been adjusted to a level of zero (stage 1608).

The operating parameters monitored in accordance with the algorithm may include temperature, time, impedance, and power. Discrete values in temperature may be used to trigger changes in energy delivery. For example, high values in temperature (e.g. 85° C.) could indicate tissue desiccation in which case the algorithm may decrease or stop the energy delivery to prevent undesirable thermal effects to target or non-target tissue. Time may also be used to prevent undesirable thermal alteration to non-target tissue. For each treatment, a set time (e.g., 2 minutes) is checked to prevent indefinite delivery of energy. Impedance may be used to measure tissue changes. Impedance indicates the electrical property of the treatment site. If a thermal inductive, electric field is applied to the treatment site the impedance will decrease as the tissue cells become less resistive to current flow. If too much energy is applied, tissue desiccation or coagulation may occur near the electrode which would increase the impedance as the cells lose water retention and/or the electrode surface area decreases (e.g., via the accumulation of coagulum). Thus, an increase in tissue impedance may be indicative or predictive of undesirable thermal alteration to target or non-target tissue. Additionally, power is an effective parameter to monitor in controlling the delivery of therapy. Power is a function of voltage and current. The algorithm may tailor the voltage and/or current to achieve a desired power. Derivatives of the aforementioned parameters (e.g., rates of change) can also be used to trigger change in energy delivery. For example, the rate of change in temperature could be monitored such that power output is reduced in the event that a sudden rise in temperature is detected.

Figure 17:
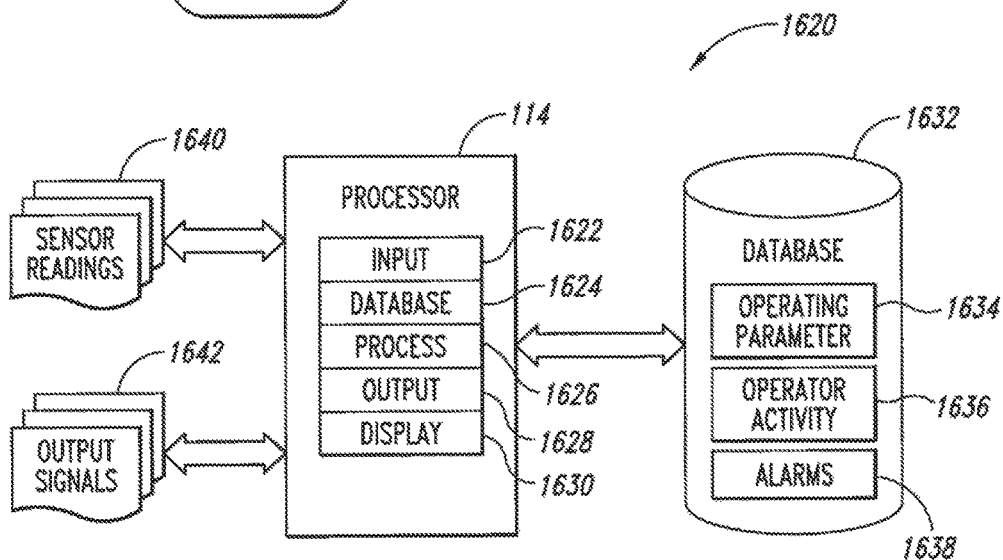
FIG. 17 is a block diagram illustrating computing system software modules for controlling thermally-induced renal neuromodulation.

To implement the aforementioned control algorithm, the system may include one or more computing system hardware and/or software modules. Alternatively, computer hardware and software can be utilized to facilitate any energy delivery process or system. FIG. 17, for example, illustrates a functional diagram showing software modules 1620 suitable for use in the processor 114 of FIG. 3A or another suitable device (e.g., the field generator 110) to perform methods for modulating renal nerves. Each component can be a computer program, procedure, or process written as source code in a conventional programming language, such as the C++ programming language, and can be presented for execution by the CPU of processor 114. The various implementations of the source code and object and byte codes can be stored on a computer-readable storage medium or embodied on a transmission medium in a carrier wave. The modules of the processor 114 can include an input module 1622, a database module 1624, a process module 1626, an output module 1628, and a display module 1630. In another embodiment, the software modules 1620 can be presented for execution by the CPU of a network server in a distributed computing scheme.

In operation, the input module 1622 accepts operator input, such as process setpoint and control selections, and communicates the accepted information or selections to other components for further processing. The database module 1624 organizes records, including an operating parameter 1634, an operator activity 1636, and one or more alarms 1638, and the database module 1624 facilitates storing and retrieving of these records to and from a database 1632. Any type of database organization can be utilized, including a flat file system, hierarchical database, relational database, or distributed database, such as those provided by Oracle Corporation of Redwood Shores, Calif.

The process module 1626 can process the sensor readings 1640 (e.g., from the sensors 310 in FIG. 5A), check for alarms and interlocks, and generate control variables for controlling an energy delivery process of the field generator 110 (FIG. 3A) based on the sensor readings 1640. The output module 1628 can generate output signals 1642 based on the control variables. For example, the output module 1628 can convert the generated control variables from the process module 1626 into output signals 1642 suitable for an energy output modulator. The display module 1630 can display, print, or download the sensor readings 1640 and the output signals 1642 via devices such as the output device 120 (FIG. 3A) or a visual display on the face of the field generator 110. A suitable display module 1630 can be a video driver that enables the processor 114 to display the sensor readings 1640 on the output device 120.

Figure 18:
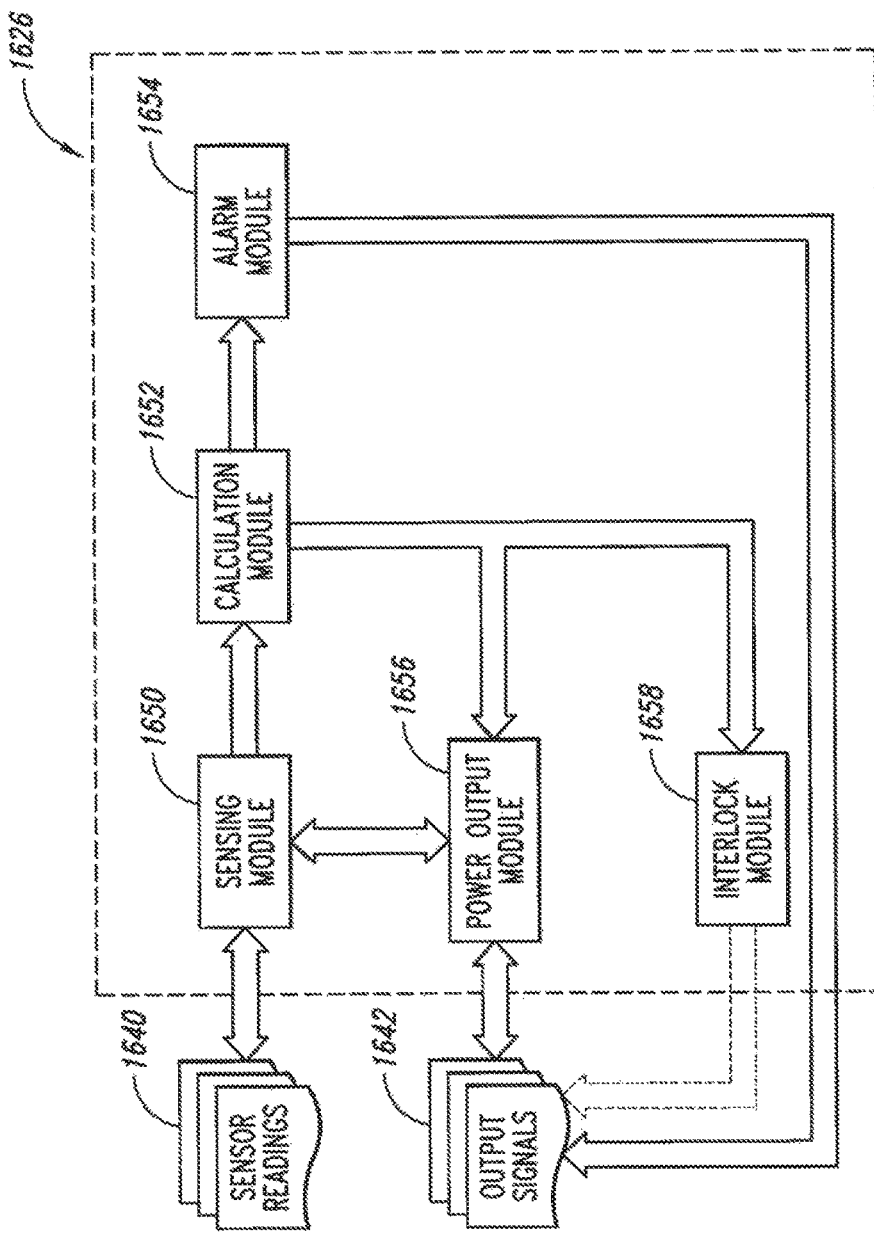
FIG. 18 is a block diagram illustrating a process module suitable to be used in the computer system of FIG. 17.

FIG. 18 is a block diagram showing an embodiment of the process module 1626 of FIG. 17. The process module 1626 can further include a sensing module 1650, a calculation module 1652, an alarm module 1654, a power output module 1656, and an interlock module 1658 interconnected with each other. Each module can be a computer program, procedure, or routine written as source code in a conventional programming language, or one or more modules can be hardware modules.

The sensing module 1650 can receive and convert the sensor readings 1640 into parameters in desired units. For example, the sensing module 1650 can receive the sensor readings 1640 as electrical signals and convert the electrical signals into instant temperatures in Celsius. The sensing module 1650 can have routines including, for example, linear interpolation, logarithmic interpolation, data mapping, or other routines to associate the sensor readings 1640 to parameters in desired units.

The calculation module 1652 can perform various types of calculation to facilitate operation of other modules. For example, the calculation module 1652 can derive an average temperature based on the measured temperatures over a period of time according to the following formula:

$$T_{avg} = \frac{\sum T_i}{N}$$

where $T_i$ is a measured temperature, $T_{avg}$ is the average temperature, and N is the number of temperature records. Other averaging techniques, such as an exponential moving average can also be used. The calculation module 466 can also derive a rate of change for the measured temperature according to the following formula:

$$\frac{dT}{dt} \approx \frac{T_{i+1} - T_i}{\Delta t}$$

where $T_{i+1}$ is the temperature record number i+1, $T_i$ is the previous temperature record, and $\Delta t$ is the time difference between the two temperature records.

The alarm module 1654 can generate alarms based on output from the calculation module 1652 and/or the sensing module 1650. For example, the alarm module 1654 can compare the average or instantaneous temperature calculated in the calculation module 1652 to a preset threshold value (i.e., predetermined parameter profile). If the average or instantaneous temperature exceeds the threshold value, the alarm module 1654 can issue an alarm by raising an alarm flag or another type of response. In response to the alarm flag, the output device 120 (FIG. 3A) can issue a notification by displaying a flashing message, sounding a horn, turning on a warning light, and/or providing another indicator. In certain embodiments, the alarm module 1654 can also include routines for implementing hysteresis. For example, the alarm module 1654 can latch the alarm flag when the average or instantaneous temperature exceeds the threshold and deactivate the alarm only when the average or instantaneous temperature drops below the threshold by a certain amount.

The power output module 1656 can generate the output signals 1642 to the field generator 110 (FIGS. 3A and 3B) for modulating power output of the field generator 110. In one embodiment, the power output module 1656 can generate the output signals 1642 according to a preset power delivery profile. For example, the power delivery profile can include a maximum power level, a minimum power level, and a rate of increase over a certain period of time to ramp from the minimum power level to the maximum power level. In other embodiments, the power output module 1656 can generate the output signals 1642 based on monitored operating parameter data or other output from the sensing module 1650 and/or the calculation module 1652. For example, the power output module 1656 can modify the rate of increase based on the average temperature calculated in the calculation module 1652, or the instant temperature from the sensing module 1650, as described below.

The interlock module 1658 continuously monitors operating parameters received from the sensing module 1650 and/or the calculation module 1652, and the interlock module 1658 can control operation of the power output module 1656 when the monitored operating parameters exceed certain interlock threshold values. Depending on the interlock condition, the power output module 1656 can set a power setpoint above or below the current setpoint (i.e., increase or decrease power) or it can set a power setpoint of zero (i.e., terminate power delivery). For example, the interlock module 1658 can cause the power output module 1656 to reduce the power output when the average temperature from the calculation module 1652 exceeds a preset value. Additionally or alternatively, the interlock module can cause the power output module 1656 to terminate its operation (i.e., having a zero output value) when the instant temperature from the sensing module 1650 exceeds another preset value. In several embodiments, the interlock module 1658 can optionally be configured to directly generate output signals 1642 to the other system components.

In certain embodiments, the process module 1626 can include additional modules. For example, the process module 1626 can include a configuration module for configuring any one of the sensing module 1650, the calculation module 1652, the alarm module 1654, the power output module 1656, and/or the interlock module 1658.

The process module 1626 can also include control modules for controlling selected process parameters. For example, the process module 1626 can include proportional-integral-derivative (PID) modules for maintaining a process parameter (e.g., the measured temperature) at a desired value. The process module 1626 can also include one or more PID modules that attempt to maintain one process parameter (e.g., temperature) unless limited by other process parameters (e.g., maximum power or impedance values). The process module 1626 can also include feed-forward modules in addition to the PID modules for improved control. For example, the feed-forward modules can calculate an expected power level based on the measured temperature, the heat conductance, and/or other parameters of the wall of the body lumen. The expected power level can then be combined with the output of the PID modules to compensate for any delayed response.

Figure 19:
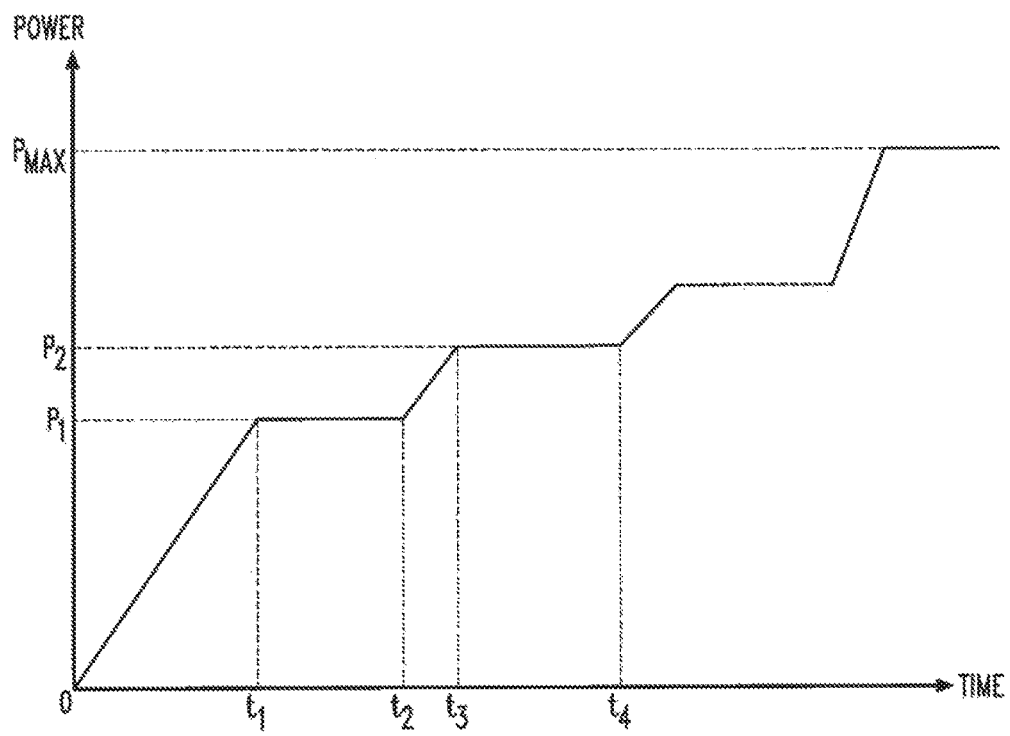
FIG. 19 is a power vs. time diagram showing an example of a response to performing the method of FIG. 16.

To better understand the methods described above with reference to FIG. 16, it may be helpful to discuss the method 1600 in view of a power delivery profile. FIG. 19, for example, is a graph of power versus time showing a typical response of performing an embodiment of the method 1600. Referring to FIGS. 16-19 together, one embodiment of the method 1600 includes a function in which the interlock module 1658 checks for interlock conditions (i.e., monitored operating parameters vs. predetermined parameter profiles), which corresponds to stages 1602 and 1604 of FIG. 16. If any interlock condition exists, then at stage 1606 the interlock module 1658 adjusts power output or delivery (e.g., increase/decrease power level or force output to zero). If it is determined that the power level is adjusted to zero at stage 1608, the therapy is terminated. The interlock conditions can include those indicating an unsafe or undesired operating state, or those indicating incomplete energy delivery. For example, the following is a non-exhaustive list of events that can be the interlock conditions:

(1) The measured temperature exceeds a maximum temperature threshold (e.g., about 70° to about 85° C.).
(2) The average temperature derived from the measured temperature exceeds an average temperature threshold (e.g., about 65° C.).
(3) The rate of change of the measured temperature exceeds a rate of change threshold.
(4) The temperature rise over a period of time is below a minimum temperature change threshold while the field generator 110 (FIG. 3A) has non-zero output. Poor contact between the electrode 108 and the wall can cause such a condition.
(5) A measured impedance exceeds an impedance threshold (e.g., <20 Ohms, or >500 Ohms).
(6) A measured impedance exceeds a relative threshold (e.g., impedance decreases from a starting or baseline value and then rises above this baseline value).

As illustrated in FIG. 19, the first interlock condition occurs at time 0 (i.e., the time at which the operator has initiated treatment and the timer begins counting up from zero). In this case, the method 1600 continues at stage 1606 with the power output module 1656 commanding the field generator 110 to gradually adjust its power output to a first power level $P_1$ (e.g., 5 watts) over a first time period $(0-t_1)$ (e.g., 15 seconds). The power output module 470 can generate and transmit a power setpoint to the field generator 110 as the output signals 1642. In one embodiment, as illustrated in FIG. 19, the power increase during the first time period is generally linear. As a result, the field generator 110 increases its power output at a generally constant rate of $P_1/t_1$. In other embodiments, the power increase can be non-linear (e.g., exponential or parabolic) with a variable rate of increase.

After the first time period expires (or after the power level at $P_1$ has been achieved), the power output module 1656 can command the field generator 110 to maintain its current output power level at $P_1$, i.e., pause for a second time period $(t_1-t_2)$. An operator or preprogrammed routine can adjust the time period $(t_1-t_2)$ based on the patient's physiological characteristics. For example, if the patient's body lumen is slow in responding to temperature changes, then the operator or preprogrammed routine can increase the time period $(t_1-t_2)$ to compensate for the additional response delay. In other embodiments, the power output module 1656 may cause the field generator 110 to reduce the output level to less than $P_1$ or momentarily terminate its output level during the second time period $(t_1-t_2)$ or any other time period (e.g., the first time period or subsequent time periods).

After the second time period expires, the calculation module 1652 can derive an average temperature at the end of the second time period, i.e., $t_2$, based on the temperature from the sensing module 1650. The method 1600 can continue with a test to determine whether the calculated average temperature at $t_2$ exceeds a preset threshold (e.g., 65° C.). If the average temperature exceeds the preset threshold, then the power output module 1656 can command the field generator 110 to maintain its current output power level for a desired total treatment time.

If the average temperature does not exceed the preset threshold, then the method 1600 can continue at stage 1606 with the power level $P_i$ being increased by an amount $\Delta P$ from $P_i$. In one embodiment, $\Delta P$ can be a predetermined fixed amount (e.g., 0.5 watts). In other embodiments, $\Delta P$ can be a variable amount. For example, the difference between the average temperature and a maximum temperature threshold can determine $\Delta P$ according to the following formula:

$$\Delta P = k \times (T_{max} - T_{avg})$$

where k is a user-selected or predetermined constant, $T_{max}$ is the maximum temperature threshold, and $T_{avg}$ is the average temperature.

The method 1600 can continue with another test to determine whether the increased power level $(P_i+\Delta P)$ exceeds a maximum power level (e.g., 10 watts) for the field generator 110. An operator or preprogrammed routine can select the maximum power level to represent a safe or preferred operating mode and adjust the selected power level based on treatment conditions. If the maximum power level is exceeded, then power output module 1656 commands the field generator 110 to maintain its current output power level until a desired total treatment time is reached. If the maximum power level is not exceeded, then the process returns to pausing, and the subsequent stages are repeated. Although the specific example of the method 1600 described above uses the measured temperature as a process parameter, other physiological parameters (e.g., impedance, resistivity, and/or capacitance) and non-physiological parameters (e.g., time, power, etc.) can be used instead of or in addition to the measured temperature.

Optionally, the calculation module 1652 can calculate the number of cycles before the maximum power level is reached. For example, when a fixed $\Delta P$ is used, the calculation module 1652 can calculate the number of cycles according to the following formula:

$$n = \frac{P_{max} - P_1}{\Delta P}$$

where $P_{max}$ is the maximum power level, and n is the number of cycles.

After the ramp up process terminates, the power output module 1656 can still command the field generator 110 to modify its power output level based on the calculated average temperature, the rate of change of the measured temperature, the rate of change in impedance, and/or other parameters. For example, as discussed below, the power output module 1656 can command the field generator 110 to discretely or continuously decrease its power output level when the measured temperature is increasing at a rate exceeding a rate of change threshold or when the measured instant temperature exceeds another preset threshold.

The method 1600 can also optionally include a ramping process that allows the power level to be increased at a faster rate. For example, the method 1600 can include a test to check the average temperature and determine if it is below a preselected threshold (e.g., 50 C). If the average temperature is below the threshold, then the power output module 1656 can command the field generator 110 to increase the power level $P_i$ by an amount equal to $\Delta P \times F$ where F is a step factor (e.g., 2). The test can be repeated at the start of each ramp stage or at other selected points in the ramping process. The rapid ramping process is expected to allow the power output level to reach its desired treatment level more quickly. In another embodiment where a PID module is used to control power output, the PID module can be tuned to rapidly ramp up power when the measured temperature is far below a specified level (e.g., 65 C) but slow down the power ramping as the measured temperature approaches the specified level.

The method 1600 can also optionally include a power reduction process to incrementally step down or ramp down the power level during treatment. The example described above specifically tailors the power output process to reduce the risk of overheating the walls of the patient's body lumen via temperature monitoring. In the case where the maximum power level is reached, the temperature and/or the measured impedance may continue to rise beyond a certain threshold. In many cases, exceeding such thresholds could be an indicator that an alarm threshold could be reached where power output would be terminated. The method described below, however, can be used to decrease power to prevent a premature termination of power delivery due to temperature and/or impedance reaching an alarm threshold.

During power delivery, the interlock module 1658 can continuously monitor one or more operating parameters received from the sensing module 1650 and/or the calculation module 1652. For example, this method can include a test to determine whether the calculated average temperature is greater than or equal to a preset threshold $T_t$ (e.g., 70° C.). If the average temperature does not exceed the preset threshold $T_t$, then the interlock module 1658 does not interrupt operation of the power output module 1656 and the current power output level is maintained for treatment.

On the other hand, if the average temperature (from the calculation module 1652) exceeds the preset threshold $T_t$, then the method can continue with stage 1606 in which the power level is reduced. During this power reduction stage, the power output module 1656 can command the field generator to immediately decrease power by $P_s$ (e.g., 1 watt). After decreasing the power, the method can pause the power output module 1656 for a time period $T_w$ (e.g., 3 seconds). After the time period $T_w$ expires, the calculation module 1652 can again derive an average temperature based on the temperature from the sensing module 1650. The method can continue with another test at to determine whether the calculated average temperature still exceeds the preset threshold $T_t$. In some cases, this power reduction process may need to be repeated several times, decreasing power by $P_s$ each time, until the average temperature does not exceed the preset threshold. If the average temperature does not exceed the threshold, the method can continue with a sustained power stage for the duration of the treatment time.

In another aspect of this embodiment, the method can include a test to determine whether an increase or rate of increase in impedance is too large. More specifically, the interlock module 1658 can measure the slope of the impedance over a fixed period of time. If the measured slope does not exceed a preset threshold, then the interlock module 1658 does not adjust operation of the power output module 1656, and the method can continue with a sustained power level. However, if the measured slope is greater than a preset threshold $Z_s$ (e.g., 3 ohms per second), then the method can proceed to the power reduction described above. As mentioned above, the power reduction process may need to be repeated several times until the measured slope does not exceed the preset threshold $Z_s$. An operator or preprogrammed routine can adjust the preset thresholds $T_t$ and $Z_s$ or the power reduction rate based on the patient's physiological characteristics and/or one or more desired treatment parameters.

In yet another aspect of this embodiment, the interlock module 1658 can continuously monitor the impedance and, if at any point during treatment the impedance rises above a minimum impedance plus a preselected threshold, the power output can be decreased until the impedance value is within the desired range. If the impedance value does not change to be within the desired range or continues to rise above an alarm threshold, then power delivery can be terminated.

In further detail, this method can include a test to compare the measured impedance value with a preselected minimum impedance value. If the measured impedance value is less than the preselected minimum impedance value, the minimum value is updated to be equal to the measured value. These stages can be repeated any number of times as necessary during treatment. In effect, the method keeps track of the lowest impedance value measured by the system.

If the measured impedance is greater than the minimum impedance value plus a preselected threshold value $Z_d$ (e.g., 20 ohms), then the method can continue to the power reduction process as described above. After decreasing the power, the method can pause the power output module 1656 for a time period $T_{w2}$ (e.g., 3 seconds). After the time period $T_{w2}$ expires, the interlock module 1658 can again monitor impedance and, if the measured impedance value is still greater than the minimum impedance value plus the threshold value, the method can repeat the power reduction process any number of times as necessary until the impedance condition does not occur, and then return to the sustained power stage.

One expected advantage of the methods 1600 and the various embodiments described above is the reduced risk of undesirable treatment effects to target and non-target tissue (e.g., excessively damaging the wall of the body lumen). As described above with reference to FIGS. 3A and 3B, the field generator 110 can deliver an electric field to the probe 104 to apply energy to the wall of the body lumen and surrounding areas for effectuating neural modulation. However, many factors can contribute to a delayed response of the body lumen to the applied energy (as indicated by the measured temperature and/or impedance). For example, the latent heat of the body lumen, circulation around or within the body lumen, contact between a sensor and the wall of the body lumen, and other factors can cause the delayed temperature and/or impedance response to the applied energy. To compensate for this delay in response, the method 1600 may incorporate a delay period in which some parameters are not monitored for the duration of the delay period. As a result, adverse overheating of the body lumen can be mitigated or even eliminated. Furthermore, a power reduction process further helps reduce the risk of excessively damaging the body lumen wall, while also preventing premature termination of power delivery due to a parameter reaching an alarm threshold.

It is expected that thermally-induced renal neuromodulation, whether delivered extravascularly, intravascularly, intra-to-extravascularly or a combination thereof, may alleviate clinical symptoms of CHF, hypertension, renal disease, myocardial infarction, atrial fibrillation, contrast nephropathy and/or other renal or cardio-renal diseases for a period of months (potentially up to six months or more). This time period may be sufficient to allow the body to heal; for example, this period may reduce the risk of CHF onset after an acute myocardial infarction to thereby alleviate a need for subsequent re-treatment. Alternatively, as symptoms reoccur, or at regularly scheduled intervals, the patient may receive repeat therapy. Thermally-induced renal neuromodulation also may systemically reduce sympathetic tone.

While the therapies disclosed herein relate to modulating nerves that contribute to renal function via denervation, it should be understood that the methods, apparatuses, and systems disclosed herein can be configured and/or modified for therapeutic energy transfer with other locations within the body. For example, these inventions can be modified for the purposes of energy delivery within a body lumen (e.g., a peripheral blood vessel) to achieve denervation or some other therapeutic result.

From the foregoing, it will be appreciated that specific embodiments of the invention have been described herein for purposes of illustration, but well-known structures and functions have not been shown or described in detail to avoid unnecessarily obscuring the description of the embodiments of the invention. Where the context permits, singular or plural terms may also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the invention. Accordingly, the invention is not limited except as by the appended claims.

We claim:

1. A field generator comprising:
a processor configured to:
increase energy delivery, from the field generator to an electrode of an intravascular catheter intravascularly positioned at a target intravascular site within a renal artery of a patient, at a generally constant rate to a predetermined first power level over a first period of time;
maintain energy delivery to the electrode at the predetermined first power level for a second period of time; and
increase energy delivery to the electrode in variable increments after the second period of time and based on a difference between an average temperature at the target intravascular site and a maximum temperature threshold when a measured temperature is less than a preset temperature threshold and a measured impedance value is less than a predetermined impedance threshold, the increase in energy delivery after the second period of time continuing until the power level has reached a target maximum power threshold.

2. The field generator of claim 1 wherein the processor is further configured to maintain energy delivery to the electrode at the predetermined first power level if the measured temperature is greater than or equal to the preset temperature threshold.

3. The field generator of claim 1 wherein the preset temperature threshold is from 45 degrees Celsius to 90 degrees Celsius.

4. The field generator of claim 1 wherein the preset temperature threshold is from 60 degrees Celsius to 75 degrees Celsius.

5. The field generator of claim 1 wherein the preset temperature threshold is 65 degrees Celsius.

6. The field generator of claim 1 wherein the predetermined first power level is 5 watts.

7. The field generator of claim 1 wherein the first period of time is 15 seconds.

8. The field generator of claim 1 wherein the second period of time is 3 seconds.

9. The field generator of claim 1 wherein the target maximum power threshold is a second power level, and wherein the processor is configured to reduce energy delivery to the electrode positioned at the target intravascular site to a third power level less than the second power level if the measured temperature reaches a second temperature threshold.

10. The field generator of claim 9 the second power level is 6 watts.

11. The field generator of claim 9 wherein the second power level is 8 watts.

12. The field generator of claim 9 wherein the reduction in power occurs in increments.

13. The field generator of claim 9 wherein the second temperature threshold is 70 degrees Celsius.

14. The field generator of claim 1 wherein the processor is configured to terminate energy delivery if an interlock condition is satisfied.

15. The field generator of claim 14 wherein the interlock condition is satisfied when the measured temperature value reaches the maximum temperature threshold.

16. The field generator of claim 15 wherein the maximum temperature threshold is an average temperature or real time temperature from 70 degrees Celsius to 85 degrees Celsius.

17. The field generator of claim 15 wherein the maximum temperature threshold is an average temperature or real time temperature of 85 degrees Celsius.

18. The field generator of claim 15 wherein the maximum temperature threshold is a rate of change threshold.

19. The field generator of claim 14 wherein the interlock condition is satisfied when the measured impedance reaches the predetermined impedance threshold.

20. The field generator of claim 19 wherein the predetermined impedance threshold is a measured impedance below 20 Ohms or above 500 Ohms.

21. The field generator of claim 20 wherein the predetermined impedance threshold is a relative threshold.

22. The field generator of claim 1 wherein the processor is configured to prevent power from exceeding the target maximum power threshold.

23. The field generator of claim 22 wherein the target maximum power threshold is from 8 watts to 10 watts.

24. The field generator of claim 22 wherein the target maximum power threshold is 10 watts.

\* \* \* \* \*